US008417459B2

(12) United States Patent
Reese et al.

(10) Patent No.: US 8,417,459 B2
(45) Date of Patent: Apr. 9, 2013

(54) METHODS OF SELECTION, REPORTING AND ANALYSIS OF GENETIC MARKERS USING BROAD-BASED GENETIC PROFILING APPLICATIONS

(75) Inventors: Martin G. Reese, Oakland, CA (US); Charles White, Oakland, CA (US)

(73) Assignee: Omicia, Inc., Emeryville, CA (US)

( * ) Notice: Subject to any disclaimer, the term of this patent is extended or adjusted under 35 U.S.C. 154(b) by 0 days.

(21) Appl. No.: 10/552,665

(22) PCT Filed: Apr. 9, 2004

(86) PCT No.: PCT/US2004/010905
§ 371 (c)(1),
(2), (4) Date: Oct. 11, 2005

(87) PCT Pub. No.: WO2004/092333
PCT Pub. Date: Oct. 28, 2004

(65) Prior Publication Data
US 2007/0042369 A1 Feb. 22, 2007

Related U.S. Application Data

(60) Provisional application No. 60/461,740, filed on Apr. 9, 2003, provisional application No. 60/492,707, filed on Aug. 4, 2003.

(51) Int. Cl.
*G06F 19/00* (2011.01)
*C12Q 1/68* (2006.01)
(52) U.S. Cl.
USPC .............................................. 702/19; 435/6.1
(58) Field of Classification Search .................. None
See application file for complete search history.

(56) References Cited

U.S. PATENT DOCUMENTS

| 6,528,260 | B1 * | 3/2003 | Blumenfeld et al. ............. 435/6 |
|---|---|---|---|
| 2002/0049772 | A1 | 4/2002 | Rienhoff, Jr. |
| 2002/0052761 | A1 | 5/2002 | Fey |
| 2002/0183934 | A1 | 12/2002 | Selifonov et al. |
| 2003/0022223 | A1 | 1/2003 | Rone |

OTHER PUBLICATIONS

Ashburner et al., "Gene Ontology: Tool for the Unification of Biology," *Nat Genet*, 25:25-29 (2000).
Fodor et al., "Light-Directed, Spatially Addressable Parallel Chemical Synthesis," *Science*, 251:767-773 (1991).
Guttmacher et al., "Genomic Medicine—A Primer," *N Engl J Med*, 347:1512-1520 (2002).
Hamosh et al., "Online Mendelian Inheritance in Man (OMIM), a Knowledgebase of Human Genes and Genetic Disorders," *Nucleic Acids Research*, 30:52-55 (2002).
Hizawa et al., "A Functional Polymorphism in the RANTES Gene Promoter is Associated with the Development of Late-Onset Asthma," *Am J Respir Crit Care Med*, 166:686-690 (2002).
Jimenez-Sanchez et al., "Human Disease Genes," *Nature*, 409:853-855 (2001).
Krawczak et al., "Human Gene Mutation Database—A Biomedical Information and Research Resource," *Human Mutation*, 15:45-51 (2000).
Miki et al., "A Strong Candidate for the Breast and Ovarian Cancer Susceptibility Gene BRCA1," *Science*, 266:66-71 (1994).
Oliphant et al., "BeadArrayTM Technology: Enabling an Accurate, Cost-Effective Approach to High-Throughput Genotyping," *BioTechniques Supplement*, 32:S56-S61 (2002).
Schulman et al., "What's New for 2001 MeSH," *NLM Tech Bull* 317 (2001).
Stajich et al., "The Bioperl Toolkit: Perl Modules for the Life Sciences," *Genome Res*, 12:1611-1618 (2002).
Trager, R., "Venter's Next Goal: 1000 Human Genomes," *Science*, 298:947 (2002).
Varmus, H., "Getting Ready for Gene-Based Medicine," *N Engl J Med*, 347:1526-1527 (2002).
Yandell et al., "Genomics and Natural Language Processing," *Nat Rev Genet*, 3:601-610 (2002).
U.S. Appl. No. 13/170,088, filed Jun. 27, 2011, Reese et al.
European search report dated Dec. 6, 2011 for EP Application No. 04759307.4.
International search report and written opinion dated Feb. 13, 2007 for PCT/US2004/010905.
European office action dated May 7, 2012 for EP Application No. 04759307.4.

\* cited by examiner

*Primary Examiner* — John S Brusca
(74) *Attorney, Agent, or Firm* — Wilson, Sonsini, Goodrich & Rosati

(57) ABSTRACT

Disclosed are a method for determining whether an individual has an enhanced, diminished, or average probability of exhibiting one or more phenotypic attributes and related methods of selecting a set of genetic markers; for providing relevant genetic information to an individual; of evaluating the probability that progeny of two individuals of the opposite sex will exhibit one or more phenotypic attributes; and for determining the genomic ethnicity of an individual.

28 Claims, 14 Drawing Sheets

| Lexicon of 'BMPs' | Thesaurus of 'BMP' synonyms | Hierarchical Ontology |
|---|---|---|
| BMP4<br>BMP2<br>DPP<br>60A<br>BMP5<br>DBL-1 | BMP<br>Bone morphogenetic protein<br>DVR<br>Decapentaplegic-vg-1-related | growth factor<br>↗ ↑ ↖<br>TGF-β  EGF  FGF<br>↗ ↖<br>BMP  Activin |
| a. | b. | c. |

FIGURE 1

Foot Deformities;
    GENE:FGFR2
  Foot Deformities, Congenital;
    GENE:tp63; GENE:HOXA13; GENE:FGFR2
Hand Deformities ;
    GENE:FGFR2; GENE:SOX9
  Hand Deformities, Congenital ;
    GENE:GDF5; GENE:tp63; GENE:HOXA13;
    GENE:ROR2; GENE:FGFR2; GENE:GNAS;
    GENE:TBX5; GENE:PAX3; GENE:TFAP2B
Jaw Diseases ;
  Cherubism ;
    GENE:SH3BP2
  Jaw Abnormalities ;
    Cleft Palate;
      GENE:GAA; GENE:COMT; GENE:FOXC2;
      GENE:FOXE1; GENE:RDS; GENE:PVRL1;
      GENE:MSX1; GENE:tp63

FIGURE 7

A2M; AACT; AADC; AASS; ABAT; ABCA1; ABCA4; ABCB1; ABCB11; ABCB4; ABCB7; ABCC1; ABCC2; ABCC5; ABCC6; ABCC8; ABCD1; ABCG2; ABCG5; ABL1; ABO; ACADL; ACADM; ACADS; ACADVL; ACAT1; ACAT2; ACCN2; ACE; ACE2; ACHE; ACLY; ACTA1; ACTC; ACTN4; ACTSA; ACVR1B; ACVRL1; AD7C-NTP; ADA; ADAM10; ADAM17; ADAM23; ADAM33; ADAMTS2; ADAMTS4; ADAMTS5; ADCY7; ADCYAP1; ADD1; ADD2; ADM; ADMR; ADORA2A; ADORA3; ADPRT; ADRA1B; ADRA2C; ADRB1; ADRB2; ADRB3; ADRBK1; ADSL; AF1Q; AFP; AGA; AGL; AGPS; AGRP; AGT; AGTR1; AGTR2; AGXT; AHC?; AICDA; AIPL1; AIRE; AK1; AKR1C1; AKR1C2; AKR1C3; AKR1C4; AKT1; ALAD; ALAS2; ALB; ALCAM; ALDH1B1; ALDH2; ALDH4A1; ALDH5A1; ALDOA; ALDOB; ALDR1; ALOX5; ALPL; AMACR; AMBP; AMH; AMHR2; AMPD1; AMPD3; AMPH; ANGPT1; ANGPT2; ANGPT4; ANK1; ANXA3; AP3B1; APBA1; APBB1; APC; APLP1; APLP2; APOA1; APOA2; APOA4; APOB; APOC1; APOC2; APOC3; APOC4; APOD; APOE; APOH; APOL1; APOL2; APOL3; APOL4; APP; APPBP1; APRT; AQP1; AQP2; AQP7; AR; ARG1; ARHC; ARHGEF11; ARHGEF12; ARHGEF6; ARNT; ARSA; ARSB; ARSE; ASAH; ASL; ASNS; ASPA; ASPH; ASS; ATF1; ATF2; ATF3; ATM; ATP1A3; ATP1B2; ATP2A1; ATP2A2; ATP2C1; ATP5A1; ATP5G1; ATP6B1; ATP6V1B2; ATP6V1C1; ATP7A; ATP7B; ATP8B1; ATPSK2; ATRN; ATRX; ATX2; AVP; AVPR2; AXIN1; AXIN2; AXL; AZGP1; B4GALT7; BACE; BACE2; BACH1; BAP1; BARD1; BAX; BBS4; BCHE; BCKDHA; BCKDHB; BCL10; BCL2; BCL2A1; BCL6; BDKRB2; BDNF; BECN1; BF; BFSP2; BGLAP; BGN; BIRC5; BIRC6; BLM; BLMH; BLNK; BMP15; BMP2; BMP3; BMP4; BMP6; BMP7; BMPR1A; BMPR1B; BMPR2; BRCA1; BRCA2; BRF2; BRS3; BSG; BTD; BTK; BUB1; BZRP; C12orf8; C1QA; C1QB; C1QG; C1S; C2; C21ORF33; C3; C3AR1; C4B; C5ORF13; C8B; C9; CA11; CA2; CACNA1A; CACNA1D; CACNA1F; CACNA1S; CACNB4; CALB1; CALCA; CALCR; CALD1; CALM1; CALM3; CANX; CAPN10; CAPN3; CARD15; CARM1; CASP1; CASP6; CASP8; CASQ1; CASQ2; CASR; CAT; CAV1; CAV2; CAV3; CBL; CBLC; CBS; CBX1; CCK; CCKBR; CCM1; CCNA2; CCNB1; CCND1; CCND2; CCND3; CCNE1; CCNF; CCR1; CCR2; CCR3; CCR4; CCR5; CCR7; CCR8; CCR9; CD14; CD151; CD1A; CD2; CD23; CD28; CD34; CD36; CD36L1; CD37; CD38; CD3D; CD3E; CD3G; CD4; CD44; CD53; CD59; CD63; CD68; CD69; CD72; CD79A; CD81; CD8A; CD8B1; CD9; CDC2; CDC20; CDC25A; CDC25B; CDC25C; CDC27; CDH1; CDH11; CDH13; CDH3; CDK4; CDK5; CDK5R1; CDK7; CDKN1A; CDKN1B; CDKN1C; CDKN2A; CDKN2B; CDW52; CDX1; CEACAM5; CEBPB; CENPA; CENPF; CETP; CFTR; CGA; CHAT; CHGA; CHGB; CHK2; CHM; CHRNA1; CHRNA3; CHRNA4; CHRNB1; CHRNB2; CHRNE; CHS1; CHUK; CHX10; CKN1; CKS1; CLCN1; CLCN5; CLCNKB; CLDN11; CLDN16; CLN2; CLN3; CLN5; CLTB; CLU; CMA1; CNGA1; CNGA3; CNGB3; CNP; CNR1; CNTF; COCH; COL10A1; COL11A1; COL11A2; COL15A1; COL17A1; COL1A1; COL1A2; COL2A1; COL3A1; COL4A3; COL4A4; COL4A5; COL4A6; COL5A1; COL5A2; COL6A1; COL6A2; COL6A3; COL7A1; COL9A2; COL9A3; COLQ; COMP; COMT; CORT; COX10; CP; CPLX1; CPLX2; CPO; CPS1; CPT1A; CPT2; CRB1; CREB1; CREBBP; CREBL2; CRH; CRHBP; CRHR2; CRIP1; CRK; CRMP1; CRP; CRX; CRYAA; CRYAB; CRYBA1; CRYBB2; CRYGC; CRYGD; CRYM; CSE1L; CSEN; CSF1; CSF1R; CSF2; CSF2RB; CSF3; CSF3R; CSL; CSNK2B; CSRP1; CST3; CST6; CSTB; CSX; CTLA4; CTNNB1; CTNS; CTSC; CTSK; CUBN; CX3CR1; CXCR4; CYB5; CYBA; CYBB; CYLD; CYP11A; CYP11B1; CYP11B2; CYP17; CYP19; CYP1A1; CYP1A2; CYP1B1; CYP21A2; CYP24; CYP26A1; CYP27A1; CYP27B1; CYP2A13; CYP2A6; CYP2A7; CYP2B6; CYP2C18; CYP2C19; CYP2C8; CYP2C9; CYP2E; CYP2F1; CYP2J2; CYP2S1; CYP39A1; CYP3A4; CYP3A43; CYP3A5; CYP3A7; CYP46; CYP4A11; CYP4B1; CYP4F11; CYP4F12; CYP4F2; CYP4F3; CYP4F8; CYP51; CYP7A1; CYP7B1; CYP8B1; ChM-I; DAB1; DAD1; DAG1; DAO; DAPK1; DBCCR1; DBH; DBI; DBP; DBT; DCC; DCN; DCX; DDB2; DDIT3; DDX5; DECR1; DES; DFNA5; DGKA; DHCR7; DIA1; DIAPH1; DIAPH2; DISC1; DKC1; DKK3; DLD; DLG4; DLL1; DLL3; DLX3; DMBT1; DMD; DMP1; DMPK; DNAI1; DNAJB9; DNCL1; DNM1; DNM1L; DNM2; DNMT1; DNMT3A; DNMT3B; DPT; DPYD; DPYS; DPYSL2; DRAP1; DRD1; DRD2; DRD3; DRD4; DRD5; DRPLA; DSG1; DSP; DTNBP1; DVL1; DVL2;

Figure 9A

DVL3; DYRK1A; DYSF; DYT1; E2F1; E2F4; EBAF; EBP; ECE1; ECGF1; ED1; EDAR; EDN1; EDN3;
EDNRA; EDNRB; EFEMP1; EFNA1; EFNB1; EFNB2; EGFR; EGR1; EGR2; EGR4; EIF2AK3; ELA2;
ELAC2; ELAVL4; ELK1; ELN; EMD; EMX2; ENC1; ENG; ENO2; ENPP1; ENPP2; EP300; EPB41;
EPB42; EPHA1; EPHA2; EPHA3; EPHA4; EPHB2; EPHB3; EPHB4; EPHB6; EPHX1; EPHX2; EPM2A;
EPOR; ERAF; ERBB2; ERBB3; ERBB4; ERCC2; ERCC3; ERCC4; ERCC5; ERCC6; ESR1; ESR2; ETFB;
ETFDH; ETS1; ETV5; ETV6; EVC; EXT1; EXT2; EXTL1; EXTL2; EXTL3; EYA1; EZH2; F10; F11; F12;
F13A1; F13B; F2; F2R; F2RL1; F2RL2; F2RL3; F3; F5; F7; F8; F9; FAAH; FACL6; FAH; FALDH?;
FANCA; FANCC; FANCF; FANCG; FAP; FASN; FAT; FBN1; FBN2; FCGR2A; FCGR3A; FCGRT;
FCMD; FDFT1; FECH; FEN1; FEZ2; FGA; FGB; FGD1; FGF3; FGF4; FGFR1; FGFR2; FGFR3; FGG;
FGL2; FH; FHL1; FHL2; FIGF; FKHL16; FKHR; FLJ10900; FLJ20359; FLNA; FLT1; FLT4; FMO3;
FMOD; FMR1; FMR2; FN1; FOG1; FOLH1; FOS; FOXC1; FOXE1; FOXL2; FOXP3?; FRDA; FREQ;
FSBP; FSHB; FSHR; FTL; FUR; FYN; G6PC; G6PD; G6PT1; G72; GAA; GABARAP; GABARAPL2;
GABBR1; GABRA1; GABRA5; GABRB1; GABRG2; GAD1; GAD2; GADD45A; GAL; GALC; GALE;
GALK1; GALNS; GALR1; GALR2; GALR3; GALT; GAMT; GAN; GAP43; GAPD; GATA1; GATA3;
GBA; GBE1; GCCR; GCDH; GCG; GCGR; GCH1; GCK; GCS1; GDF10; GDF5; GDF9; GDI1; GDNF;
GFRA1; GGCX; GH1; GH2; GHR; GHRHR; GHSR; GIF; GIPR; GJA3; GJA8; GJB1; GJB2; GJB3; GJB4;
GJB6; GK; GLA; GLB1; GLDC; GLI3; GLRA1; GLRB; GLTSCR1; GLUD1; GM2A; GNAI2; GNAL;
GNAS; GNAT1; GNB3; GNE; GNL1; GNLY; GNPAT; GNRHR; GOT1; GOT2; GP1BA; GP1BB; GP5;
GP9; GPC3; GPHN; GPI; GPR10; GPR102; GPR37; GPR58; GPR9; GPS1; GPX1; GRAP2; GRHPR;
GRIA1; GRIA2; GRIA3; GRIK2; GRIK3; GRIK4; GRIK5; GRIN1; GRIN2B; GRO1; GRO2; GSK3A;
GSK3B; GSN; GSS; GSTP1; GTF2H1; GTRAP3-18; GUCA1A; GUCY2D; GUSB; GYS1; GYS2; GZMA;
GZMK; GZMM; H19; H1F1; H2AX; H2AZ; H3F3B; HADHA; HADHB; HAS2; HAVCR1; HBA1; HBA2;
HBB; HBD; HBG1; HBG2; HCF2; HCN1?; HCN2; HCN4; HCR; HD; HDAC1; HDAC2; HEMB; HEPH;
HER2; HESX1; HEXA; HEXB; HEY1; HEY2; HF1; HFE; HGD; HIC1; HK1; HLA-DNA; HLA-DPB1;
HLA-DQA1; HLA-F; HLA-G; HLCS; HLXB9; HMBS; HMG17; HMG2; HMGCL; HMGCR; HMGCS1;
HMGCS2; HMOX1; HNF4A; HOX11L1; HOXA11; HOXA13; HOXA5; HOXA9; HOXB5; HOXD13;
HOXD8; HP; HPCAL1; HPGD; HPN; HPRT1; HPS1; HPSE; HR; HRAS; HRG; HRH3; HRH4; HSD11B1;
HSD11B2; HSD17B3; HSD17B4; HSD3B1; HSD3B2; HSPA1A; HSPA1B; HSPA2; HSPA5; HSPB1;
HSPCA; HTATIP; HTR1A; HTR1B; HTR1D; HTR1E; HTR1F; HTR2A; HTR2B; HTR2C; HTR5A; HTR6;
HTR7; HUS1; HYAL1; IAPP; ICAM1; ICAM2; ICAM5; ID1; ID2; ID3; ID4; IDE; IDH3A; IDUA; IF;
IFI30; IFNG; IFNGR1; IFNGR2; IGF1; IGF2; IGF2R; IGFBP3; IGFBP5; IGFBP6; IGFBP7; IGHM; IGSF6;
IKBKB; IKBKG; IL10; IL10RA; IL10RB; IL11; IL12A; IL12B; IL12RB1; IL13; IL13RA1; IL15RA; IL17;
IL17B; IL18; IL19; IL1A; IL1B; IL1R1; IL1R2; IL1RAPL; IL1RN; IL2; IL20; IL21R; IL22; IL24; IL2RA;
IL2RB; IL2RG; IL3; IL4; IL4R; IL5; IL6; IL7R; IL8; IL8RA; IL8RB; IL9; IL9R; IMMP2L; INA; INHBA;
INS; INSR; IPF1; IRAK4; IRF1; IRF7; IRS1; ISGF3G; ITGA2; ITGA2B; ITGA3; ITGA5; ITGA6; ITGA7;
ITGA8; ITGAV; ITGB1; ITGB2; ITGB3; ITGB4; ITK; ITM2B; ITPR1; IVD; JAG1; JAG2; JAK3; JK; JUN;
JUP; KAI1; KAL1; KCNA1; KCNC1; KCNE1; KCNE2; KCNG1; KCNH2; KCNJ1; KCNJ11; KCNJ13;
KCNK10; KCNK2; KCNK3; KCNK5; KCNMB3; KCNN3; KCNQ1; KCNQ2; KCNQ3; KCNQ4; KCNS1;
KDR; KEL; KERA; KIF5B; KISS1; KIT; KLK1; KLK10; KLK2; KLK3; KLK6; KLK8; KLKB1; KLRD1;
KNG; KNS2; KNS2B; KNSL1; KNSL5; KNSL6; KPNB1; KRAS2; KRT1; KRT12; KRT13; KRT14;
KRT16; KRT17; KRT2A; KRT3; KRT4; KRT5; KRT6A; KRT6B; KRT9; KRTHB1; KRTHB6; L1CAM;
LAD1; LAMA2; LAMA3; LAMB3; LAMC1; LAMC2; LAMP1; LAMR1; LCAT; LCK; LDHA; LDLR;
LEP; LEPR; LFNG; LHB; LHCGR; LHX3; LIG1; LIG4; LILRB2; LILRB4; LIM2; LIPA; LIPC; LIPE;
LMAN1; LMNA; LMO4; LMX1B; LOR; LPA; LPL; LRP1; LRP2; LRP5; LRP6; LRP8; LTA; LTB;
LTBP1; LTBP2; LTBR; LYZ; MAD2L1; MADD; MADH4; MAG; MAGEA2; MAGEA3; MAGEA4; MAL;
MAN2B1; MANBA; MAOA; MAOB; MAP2; MAP2K4; MAP3K1; MAP3K14; MAP3K5; MAP3K8;
MAPK8; MAPK8IP1; MAPT; MAT1A; MBD1; MBL2; MBP; MBTPS1; MC1R; MC2R; MC3R; MC4R;

FIGURE 9B

MCL1; MCOLN1; MD-2; MDH1; MDM2; MECP2; MEF2B; MEF2C; MEFV; MEN1; MET; MFNG;
MGAT2; MGMT; MGP; MHC2TA; MHY6; MID1; MIF; MIG; MIP; MITF; MJD; MKKS; MLH1; MLP;
MLP?; MLYCD; MMD; MMP1; MMP10; MMP12; MMP2; MMP3; MMP7; MMP8; MMP9; MN1; MNDA;
MOCS1; MOCS2; MOG; MOS; MPI; MPL; MPO; MPP1; MPS2; MPZ; MPZL1; MRE11A; MRP3;
MS4A2; MSH2; MSH6; MSLN; MSX1; MSX2; MT1A?; MT2A; MT3; MTA1; MTHFR; MTM1; MTMR2;
MTNR1A; MTNR1B; MTP; MTR; MTRR; MUT; MVK; MVP; MYB; MYBL2; MYBPC3; MYC; MYCN;
MYH7; MYH9; MYL2; MYL3; MYO15A; MYO5A; MYO6; MYO7A; MYOC; MYOCARDIN?; MYOD1;
MYT1; N33; NAGA; NAGLU; NARS; NASP; NAT2; NBS1; NCAM1; NCF1; NCF2; NCL; NCOA1;
NCOA2; NCOA3; NCOA4; NCOR1; NCOR2; NCSTN; NDN; NDP; NDRG1; NDUFA5; NDUFS4;
NDUFS7; NDUFS8; NDUFV1; NDUFV2; NEB; NEF3; NEFH; NEFL; NELL1; NELL2; NEU1;
NEUROD1; NEUROG1; NF1; NF2; NFKB1; NFKB2; NFKBIA; NFKBIB; NGFB; NKG7; NKX3A; NME1;
NME2; NME3; NME4; NNAT; NODAL?; NOG; NOS1; NOS2A; NOS3; NOTCH1; NOTCH2; NOTCH3;
NOTCH4; NOV; NOVA1; NOVA2; NP; NPC1; NPFF; NPHP1; NPHS1; NPHS2; NPM1; NPPA?; NPPB;
NPPC; NPTX1; NPY; NPY1R; NQO1; NR0B2; NR1H4; NR1I2; NR3C1; NR3C2; NR5A1; NRAS; NRG1;
NRIP1; NRL; NRTN; NSF; NTF3; NTN1; NTRK1; NTRK2; NTRK3; NUMA1; NUP88; OA1; OAT; OAZIN; OCA2; OCRL; OGG1; OLFM1; OLIG2; OPHN1; OPN1LW;
OPN1MW; OPN1SW; OPRD1; OPRK1; OPRM1; OTC; OTOF; OXCT; PABPN1; PAFAH1B1; PAH;
PAI1; PAI2; PAI2?; PAK3; PARK2; PAX2; PAX3; PAX6; PAX7; PAX8; PAX9; PC; PCAF; PCBD; PCCA;
PCCB; PCI; PCK1; PCMT1; PCNA; PCP4; PCQAP; PCSK1; PDCD8; PDE6A; PDE6B; PDGFB; PDGFRA;
PDGFRL; PDHA1; PDK2; PDX1; PDYN; PEA15; PEG3?; PENK; PEPD; PEX1; PEX10; PEX13; PEX6;
PEX7; PFC; PFKM; PFN1; PFN2; PGAM2; PGD; PGK1; PGLYRP; PGR; PHB; PHEX; PHKA1; PHKA2;
PHKB; PHKG2; PHYH; PI12; PI3K; PI8; PICALM; PIGA; PIGF; PIK3CA; PIK3CD; PIK4CA; PIM1;
PIN1; PITX2; PITX3; PKD1; PKD2; PKLR; PKP1; PLA2G1B; PLA2G2A; PLA2G7; PLAT; PLAU;
PLAUR; PLEC1; PLG; PLK; PLN; PLOD; PLP1; PML; PMM2; PMP22; PMS1; PMS2; PNMT; PNOC;
PNR; POLH; POLR2A; POLR2F; POLR2J; POMC; PON1; PON2; POR; POU1F1; POU3F4; POU4F3;
POU5F1; PPARA; PPARBP; PPARG; PPARGC1; PPGB; PPOX; PPP1CC; PPP2R2B; PPP3CB; PPP3CC;
PPT1; PR48; PRCC; PRDM2; PRF1; PRG4; PRKAB1; PRKAB2; PRKACA; PRKACB; PRKAG2;
PRKAR1A; PRKAR1B; PRKAR1B?; PRKAR2A; PRKAR2B; PRKCA; PRKCB1; PRKX; PRL; PRNP;
PROC; PROCR; PROK1; PROML1; PROP1; PROS1; PROZ; PRPS1; PRSS1; PRSS11; PRSS8; PSAP;
PSEN1; PSEN2; PSMA1; PSMA2; PSMA3; PSMA5; PSMC2; PSMC6; PSMD11; PSMD12; PSMD4;
PTAFR; PTCH; PTCH2; PTEN; PTGDS; PTGER3; PTGIS; PTGS1; PTGS2; PTH; PTHLH; PTHR1;
PTK2B; PTP4A3; PTPN12; PTPRC; PTS; PVALB; PVRL1; PVT1; PXMP3; PXR1; PYGL; PYGM; QDPR;
RAB27A; RAB3A; RAB5A; RAC1; RAC2; RAC3; RAD51; RAD54B; RAD54L; RAG1; RAG2; RAI1;
RANBP1; RAP1GDS1; RARA2?; RARB; RASA1; RASGRF1; RASSF1; RB1; RB1CC1; RBBP4; RBBP7;
RBBP8; RBL1; RBL2; RBP4; RDBP; RDH5; RDS; RECQL4; REL; RELA; RELB; RELN; REN; REQ;
RET; RFC1; RFX5; RFXANK; RFXAP; RGR; RGS4; RGS7; RHAG; RHO; RHOK; RLBP1; RNASE1;
RNASEL; ROM1; ROR2; RP1; RPE65; RPGR; RPL10; RPL12; RPL15; RPL17; RPL18; RPL18A; RPL19;
RPL21; RPL22; RPL23; RPL23A; RPL24; RPL26; RPL27A; RPL3; RPL30; RPL36AL; RPL37; RPL39;
RPL4; RPL41; RPL5; RPL6; RPL7A; RPL8; RPL9; RPS10; RPS11; RPS12; RPS13; RPS14; RPS15;
RPS15A; RPS16; RPS17; RPS18; RPS19; RPS2; RPS20; RPS21; RPS23; RPS24; RPS25; RPS26; RPS27;
RPS27A; RPS28; RPS29; RPS3; RPS3A; RPS4X; RPS4Y; RPS6; RPS6KA3; RPS7; RPS8; RPS9; RS1;
RTN1; RTN4; RUNX1; RUNX2; RXRA; RXRB2?; RXRG2?; RYR1; RYR2; RYR3; S100A2; S100B;
SACM2L; SACS; SAFB; SAG; SAH; SALL1; SAP18; SCA1; SCA7; SCG2; SCGB3A1; SCN1A; SCN1B;
SCN2B; SCN3B; SCN4A; SCN5A; SCNN1A; SCNN1B; SCNN1G; SCO1; SCO2; SCYA2; SCYA21;
SCYA5; SCYA7; SCYA8; SCYB10; SCYD1; SDC1; SDF1; SDHA; SDHD; SEDL; SELE; SELL; SELP;
SELPLG; SEMA3A; SEMA4D; SEPP1; SERPINA1; SERPINA4; SERPINA5; SERPINB5; SERPINC1;
SERPINE1; SERPINF2; SERPINI1; SF1; SFN; SFRS8; SFTPA1; SFTPA2; SFTPB; SFTPC; SFTPD;

FIGURE 9C

SGCA; SGCB; SGCD; SGCG; SGNE1; SGSH; SH2D1A; SHBG; SHH; SHMT1; SHMT2; SHOX; SI;
SIM1; SIX3; SLC10A1; SLC10A2; SLC11A1; SLC12A1; SLC12A3; SLC12A5; SLC17A5; SLC19A2;
SLC1A1; SLC1A2; SLC1A3; SLC1A6; SLC1A7; SLC21A6; SLC22A1L; SLC22A5; SLC25A13;
SLC25A15; SLC25A16; SLC25A20; SLC25A4; SLC25A6; SLC26A2; SLC26A3; SLC26A4; SLC2A1;
SLC2A2; SLC2A4; SLC2A5; SLC31A2; SLC3A1; SLC4A1; SLC4A4; SLC5A1; SLC5A5; SLC6A1;
SLC6A2; SLC6A3; SLC6A4; SLC7A7; SLC7A9; SLC8A1; SLC9A1; SLC9A2; SLC9A3; SLC9A3R1;
SLC9A3R2; SLC9A5; SLC9A6; SMARCA1; SMARCA2; SMARCB1; SMARCC1; SMN1; SMP1;
SNAP25; SNCA; SNCAIP; SNCB; SNRPN; SOD1; SOST; SOX10; SOX4; SOX9; SP4; SPARCL1;
SPG20?; SPG4; SPG7; SPI1; SPINK1; SPINK2; SPINK5; SPINT2; SPN; SPOCK; SPP1; SPTA1; SPTB;
SPTLC1; SRC; SRD5A2; SRF; SRR; SRY; SST; SSTR2; ST14; ST7; STAR; STAT4; STAT6; STC1; STC2;
STK11; STK38; STMN2; STS; STXBP2; SULT1A1; SURF1; SYN1; SYN2; SYNGR1; SYNJ1; SYP;
SYT5; TAC1; TAC3; TACR1; TACSTD2; TAL1; TAT; TAZ; TBP; TBX3; TBX5; TBXA2R; TBXAS1;
TCAP; TCF1; TCF2; TCF7L2; TCIRG1; TCN1; TCN2; TECTA; TEK; TEM8?; TERT; TES; TF; TFAM;
TFAP2B; TFCP2; TFDP2; TFPI; TFR2; TG; TGFA; TGFB1; TGFB3; TGFBI; TGFBR2; TGIF; TGM1; TH;
THBD; THBS1; THBS2; THBS4; THPO; THRB; THY1; TIE; TIM3; TIMM17A; TIMM8A; TIMP3;
TIRAP; TLR4; TM4SF1; TM4SF2; TMSB10; TMSB4X; TNF; TNFAIP1; TNFAIP2; TNFRSF10A;
TNFRSF10B; TNFRSF11A; TNFRSF11B; TNFRSF1A; TNFRSF1B; TNFRSF5; TNFRSF6; TNFSF11;
TNFSF5; TNFSF6; TNIP3; TNNI3; TNNT1; TNNT2; TP53; TP63; TP73; TPD52; TPI1; TPM1; TPM3?;
TPMT; TPO; TRAF6; TRC8; TRDN; TRH; TRHR; TRIM37; TRIP15; TRPS1; TRPV5; TRPV6; TSC1;
TSC2; TSHB; TSHR; TTN; TTPA; TTR; TULP1; TWIST; TXNIP; TYMS; TYR; TYROBP; TYRP1;
U2AF65; UBA52; UBB; UBCH10; UBE2N; UBE2V2; UBE3A; UBL1; UCHL1; UFD1L; UGCG; UGDH;
UGT1A1; UMPS; UNG; UROD; UROS; USH2A; USP14; USP9X; USP9Y; UTRN; VCAM1; VCL; VCX?;
VDAC1; VDR; VEGF; VEGFB; VEGFC; VELI1; VHL; VLDLR; VMD2; VSNL1; VTN; VWF; WAS;
WASF1; WFS1; WHN; WISP3; WKL1; WRN; WT1; XDH; XK; XPA; XPC; XRCC2; XRCC3; YWHAG;
YWHAH; ZAKI4; ZAP70; ZIC2; ZIC3; ZNF145; ZNF161; ZNF193; ZNF217; ZNF74; ZP3A

FIGURE 9D

FIGURE 10

METHODS OF SELECTION, REPORTING AND ANALYSIS OF GENETIC MARKERS USING BROAD-BASED GENETIC PROFILING APPLICATIONS

CROSS REFERENCE TO RELATED APPLICATIONS

This application is a National Stage filing under 35 U.S.C. §371 of International Application No. PCT/US04/10905, filed Apr. 9, 2004, and claims priority under 35 U.S.C. §119 (e) of U.S. Provisional application Ser. No. 60/461,740, filed Apr. 9, 2003; and U.S. Provisional application Ser. No. 60/492,707, filed Aug. 4, 2003, each of which is hereby incorporated by reference in its entirety.

BACKGROUND OF INVENTION

Personalized human health care products and services that enable individuals to more actively manage their health based on their genetic profiles have been increasingly heralded following the publication of a draft human genome sequence in June 2000 (Venter, J C, Funct Integr Genomics. 2000 November; 1(3):154-5) and a substantially complete sequence of the human genome in February 2001. (Venter, J C et al., Science 291(5507):1304-51 [2001]; Lander E S et al., Nature 409 (6822):860-921 [2001]). To date, however, the commercial availability of personalized genetic profile products and services has been extremely limited and costly.

The "genome" of an individual member of a species comprises that individual's complete set of genes. Particular locations within the genome of a species are referred to as "loci" or "sites". "Alleles" are varying forms of the genomic DNA located at a given site. In the case of a site where there are two distinct alleles in a species, referred to as "A" and "B", each individual member of the species can have one of four possible combinations: AA; AB; BA; and BB. The first allele of each pair is inherited from one parent, and the second from the other.

The "genotype" of an individual at a specific site in the individual's genome refers to the specific combination of alleles that the individual has inherited. A "genetic profile" for an individual includes information about the individual's genotype at a collection of sites in the individual's genome. As such, a genetic profile is comprised of a set of data points, where each data point is the genotype of the individual at a particular site.

Genotype combinations with identical alleles (e.g., AA and BB) at a given site are referred to as "homozygous"; genotype combinations with different alleles (e.g., AB and BA) at that site are referred to as "heterozygous." It has to be noted that in determining the allele in a genome using standard techniques AB and BA cannot be differentiated, meaning it is impossible to determine from which parent a certain allele was inherited, given solely the genomic information of the individual tested. Moreover, variant AB parents can pass either variant A or variant B to their children. While such parents may not have a predisposition to develop a disease, their children may. For example, two variant AB parents can have children who are variant AA, variant AB, or variant BB. For example, one of the two homozygotic combinations in this set of three variant combinations may be associated with a disease. Having advance knowledge of this possibility allows potential parents to make the best possible decisions about their children's health.

Diseases are often associated with the collection of atoms, molecules, macromolecules, cells, tissues, organs, structures, fluids, metabolic, respiratory, pulmonary, neurological, reproductive or other physiological function, reflexes, behaviors and other physical characteristics observable in the individual through various means. The "phenotype" of an individual refers to one or more of these observable physical characteristics. An individual's phenotype is driven in large part by constituent proteins in the individual's proteome, the collection of all proteins produced by the cells comprising the individual and coded for in the individual's genome.

In many cases, a given phenotype can be associated with a specific genotype. For example, an individual with a certain pair of alleles for the gene that encodes for a particular lipoprotein associated with lipid transport may exhibit a phenotype characterized by a susceptibility to a hyperlipidemous disorder that leads to heart disease.

While efforts have been undertaken to create new personalized active health management products and services based on genetic profiles, several shortcomings characterize the existing art. Among these shortcomings are the following:

First, the mix of existing products and services are in the aggregate narrowly focused on a small set of disease phenotypes, making them inefficient in enabling health management practices that encompass a broad set of phenotypes;

Second, existing genetic testing products and services are each focused on a genetic indication for one or a small set of diseases;

Third, until the high cost of sequencing the genome of an individual human declines by several orders of magnitude, an alternative to genome sequencing technology must be used as the basis for genetic profile products and services, and currently available alternatives require substantial modification in order to be integrated into the array of technologies and logistics necessary to provide genetic profile products and services encompassing a comprehensive set of diseases;

Fourth, existing informatics and database management tools do not scale efficiently or effectively to the dynamic and exponential growth of reported scientific research and clinical findings underlying genetic profile products and services, resulting in a high degree of information obsolescence;

Fifth, existing genetic profile products and services are designed to be used at key life events, such as disease onset, family disease onset, preconception and prenatal events, and typically by one or more members of a family with an already-known history a particular disease among its generations, rather than as part of a comprehensive personalized health management program; and Sixth, genetic counseling practices, focused on point tests assessed at key life events must be significantly altered to support the increase in information volume and complexity arising from broad-based genetic profiling.

The objective of personalized genetic profile health management products and services is to provide individuals with information about their predisposition to diseases. Armed with this information, individuals can, in many instances, make decisions about their dietary practices, pharmaceutical use, exercise, and other lifestyle habits that are designed to better manage their predisposition to diseases.

From individual to individual within any species, genes are characterized by a very high degree of conservation in the sequence of nucleotide base pairs comprising them. At certain locations in many sites, however, the specific nucleotides that comprise a gene can undergo alteration, or mutation. Mutations can be inherited from a parent or acquired during a person's life. A hereditary mutation will be present in all of a person's cells and will be passed on to future generations, because the person's reproductive cells (sperm or egg) will contain the mutation. An acquired mutation can arise in the DNA of individual cells as a result of many possible factors. For example, mutations in the DNA of skin cells can be caused by exposure to the sun's UV radiation Genetic mutations in other cells can arise from errors that occur just prior to cell division, during which a cell makes a copy of its DNA before dividing into two. Genetic profile products and services tend to focus on hereditary mutations.

The situation in which two or more sequence variants of an allele exist at a site across different members of a population is called a "polymorphism," typically defined as having an occurrence frequency of larger than 1% within that population. Several different types of polymorphisms are known in the art. By far the most common form of polymorphisms are those involving single nucleotide variations between individuals of the same species; such polymorphisms are called "single nucleotide polymorphisms", or "SNPs". To date, at least 1.42 million SNPs have been identified in the human genome. (Sachidanandam R et al., Nature 409(6822):928-33 [2001]). While it is believed that the great preponderance of these SNPs are harmless, there is a substantial number that have been associated with various diseases.

SNPs that occur in the protein coding regions of genes that give rise to the expression of variant or defective proteins are potentially the cause of a genetic-based disease. Even SNPs that occur in non-coding regions can result in altered mRNA and/or protein expression. Examples are SNPs that defective splicing at exon/intron junctions. Exons are the regions in genes that contain three-nucleotide codons that are ultimately translated into the amino acids that form proteins. Introns are regions in genes that can be transcribed into pre-messenger RNA but do not code for amino acids. In the process by which genomic DNA is transcribed into messenger RNA, introns are often spliced out of pre-messenger RNA transcripts to yield messenger RNA.

For example, in the "healthy" form of the protein hemoglobin, the amino acid at the sixth position in the protein's beta chain is glutamic acid. This amino acid is encoded in the hemoglobin gene by the DNA codon guanine-adenine-guanine (GAG). In some individuals, however, the adenine nucleotide in this codon is replaced with the thymine nucleotide, resulting in a GTG codon which codes for the amino acid valine. This substitution of valine for glutamic acid alters the normal shape of the hemoglobin protein. Red blood cells that contain these abnormally shaped hemoglobin proteins exhibit a sickle shape and are unable to perform the oxygen-transport function normally associated with red blood cells. Individuals who are GTG homozygous (i.e., have inherited a GTG variant from each parent) suffer from sickle cell anemia.

In addition to sickle cell anemia, SNPs have been associated with diseases such as cystic fibrosis, Huntington's chorea, beta-thalassemia, muscular dystrophy, fibro muscular displasia, pheny ketonuria, Type II diabetes, a hyperlipidemous disorder associated with Apolipoprotein E2, at least one form of hypertension, and some forms of migraine headaches. These disease-associated SNPs are inherited through classic Mendelian mechanisms. This type of SNP, however, is not believed to be the predominant form of SNPs associated with the most common diseases. This view is supported by the theory that common mutations in the protein coding regions would entirely dysfunction protein structures and therefore completely shutdown a specific pathway or parts of such pathways, a result which is not supported by observation. Nevertheless, it is believed that functional variants associated with phenotypes further associated with diseases should be clustered around non-coding sites that play an important role in the functioning of the genome.

An example of such functional, non-coding sites are the "splice sites" at which pre-messenger RNA transcripts are spliced into messenger RNA (mRNA). The need for splicing arises from the fact that within the pre-messenger RNA transcripts are RNA base pairs that correspond to introns in the genomic DNA from which the pre-messenger RNA transcript derives. The complex of proteins and RNA at which splicing occurs is called the "spliceosome". (See, e.g., Fairbrother et al. 2002).

A few different methods are commonly used to analyze DNA for polymorphisms and genotype. The most definitive method is to sequence the DNA to determine the actual base sequence (see, A. M. Maxam and W. Gilbert, Proc. Natl. Acad. Sci. USA 74:560 (1977); Sanger et al., Proc. Natl. Acad. Sci. USA 74:5463 (1977)). Patent application 20020082869, "Method and system for providing and updating customized health care information based on an individual's genome", Anderson, Glen J., describes a system for delivering personalized genetic profiling information based on sequencing. Although such a method is the most definitive it is also the most expensive and time-consuming method. Accordingly, the sequencing of the human genome has only been performed for research purposes such as the Human Genome Project on samples from a very small number of individual humans, and at a cost of millions of dollars per individual. While the cost of sequencing the genome of an individual human has been following a steeply declining price/performance curve, where performance is measured in terms of accuracy and time, the substantial cost that still stands today prohibits its use on a broad commercial scale. Until the cost of sequencing technologies declines substantially further, the delivery of genetic profiles to a significantly large number of individuals cannot be cost effectively based on genome sequencing. Moreover, as described below, simply being able to sequence an individual's genome is not sufficient to generate and provide a comprehensive genetic profile product or service to the individual.

Another method of analyzing DNA for polymorphisms and genotype is restriction mapping analysis. With this method genomic DNA is digested with a restriction enzyme and the resulting fragments are analyzed on an electrophoresis gel or with a Southern blot to determine the presence or absence of a polymorphism that changes the recognition site for the restriction enzyme. This method can also be used to determine the presence or absence of gross insertions or deletions in genomic DNA by observing the lengths of the resulting DNA fragments. In this respect, restriction mapping analysis has limited use in the type of genome-wide search for polymorphisms and genotyping analysis required for providing genetic profile products and services of the type contemplated by the present invention.

Another method of determining the genotype of an individual at a given site is to detect the presence of one or more nucleotide sequences at that site known to be associated with a predisposition, disease or other phenotypic abnormality. These sites, also called "genetic markers," can be detected using various tagged oligonucleotide hybridization technologies that are significantly less costly than genomic sequencing and allele-specific hybridization. Means now exist for constructing and performing large-scale, multiplexed genetic marker hybridization tests on biological samples from individuals, such as samples of blood, saliva and urine. These means, such as very dense chip and bead arrays, can enable a sample from an individual to be tested simultaneously for the presence of thousands of genetic markers. (Oliphant A et al., Biotechniques Suppl:56-8, 60-1 [2002]; and Fodor S P, Science 251(4995):767-73 [1991]).

Splice junctions in pre-messenger RNA, 5-prime (exon to intron transition) and 3-prime (intron to exon transitions), are the sequence regions that are used as recognition sites for the spliceosome and contain certain sequence motifs which typically are conserved between related species. Nucleotide changes in these binding sites can have a substantial effect on the spliced mRNA product, depending on the effect of the mutation on the overall binding affinity of the spliceosome components with the mRNA sequence. Known mis-splicing behavior arises from exon skipping, alternative splicing, protein coding truncation through the introduction of a frame shift, and the disruption of the entire mRNA production process. These changes have significant effects in the mRNA and protein processing step and can totally change their production. In addition, smaller changes can partially regulate and influence quantitatively the splicing behavior of certain genes. Additional sites known to be involved and sometimes even known to regulate splicing, are the branch-point, enhancer and silencer sequences (Fairbrother et al. 2002). Splice sites constitute locations in the genome for evolutionary pressure to function through nucleotide mutations.

Similarly, promoter regions in genes constitute locations in the genome where the presence of a SNP can be used for determining an individual's genotype. As gene-expression regulatory mechanisms, promoter regions include the transcription start site and various transcription factor-binding sites, including all the regions that are involved in gene regulation.

The determination of the presence of polymorphisms or, less frequently, mutations, in DNA has become a very important tool for a variety of purposes. Detecting mutations that are known to cause or to predispose persons to disease is one of the more important uses of determining the possible presence of a mutation. One example is the analysis of the gene named BRCA1 that may result in breast cancer if it is mutated (see, Mild et al., Science, 266:66-71, 1994). Several known mutations in the BRCA1 gene have been causally linked with breast cancer. It is now possible to screen women for these known mutations to determine whether they are predisposed to develop breast cancer. Some other uses for determining polymorphisms or mutations are for genotyping and for mutational analysis for positional cloning experiments.

In some cases, as illustrated in the case of the hemoglobin SNP and sickle cell anemia, the association of a SNP with a disease is direct and well-established and can be simply diagnosed. In many other cases, however, the association of a SNP with a phenotype that gives rise to disease or other adverse medical condition is not well-established and different diseases, disorders have different associations with different genotypes and SNPs. In these cases, the association between genotype and phenotype can vary from individual to individual in a complex manner that depends on the individual's genome, age, family history, life style habits, and other personal health and demographic factors. Consequently, direct testing of the individual's DNA is not accurate 100% of the time in predicting the onset of a genetically-based disease or other adverse medical condition. In these more complex cases, there is a probabilistic relationship between genotype (as characterized by different variants and SNPs) and phenotype (as characterized by the association of phenotypes with different diseases). In these cases, the presence of a SNP at a given genetic site is not sufficient by itself for the development of a pathological condition In addition, not all persons possessing a given SNP in a given variant will develop a disease associated with that SNP. The onset of a genetically-based disease may also depend on exposure to certain conditions in a person's environment. Moreover, the same disease, disorder, or other adverse medical condition associated with a given SNP in a given variant may result from a different SNP at another site. Consequently, comprehensive analysis of the relationship between an individual's genotype and phenotype requires a scoring matrix of variables along various dimensions and a method of using this matrix to determine the probability that a given genotype in a given individual win result in a given phenotype.

To further illustrate the complexity of associating genotypes with phenotypes, it is currently believed that the human genome comprises approximately 30,000 genes while the human proteome comprises potentially millions of proteins. The process by which the information contained in the DNA comprising 30,000 distinct genes is transcribed into messenger RNA, which is in turn translated into the sequence of amino acids comprising potentially millions of distinct proteins, therefore adds significant complexity to associations of genotypes with phenotypes. In addition, in the search for unknown disease-causing variants, whole-genome association scans using hundreds of thousands of genetic markers simultaneously are likely to face serious theoretical-statistical challenges, as well as practical difficulties associated with the management of data sets of enormous size and complexity. One obvious problem is the fact that, the more genetic markers are used, the higher the expected number of apparent, spurious associations that are the result of statistical chance as opposed to true association stemming from shared genealogy between genetic marker and causative allele.

Beyond this complexity of associating genotypes with phenotypes, there has been rapid growth of data on the existence of SNPs, their locations in the human genome, and associations of SNPs with phenotypes that are further associated with various diseases. This data arises from research on genomics, proteomics, preclinical and clinical studies of pharmaceuticals and related research gathered from laboratories, hospitals and medical clinics around the world.

Genomics has the potential to change the way medicine is practiced and impact the health of individuals. (E.g., Guttmacher A E, Collins F S, *Genomic medicine—a primer*, N Engl J Med 347: 1512-20. and Collins [2002]; Varmus, *Getting ready for gene-based medicine*, N Engl J Med 347: 1526-7 [2002]). Through sequencing and genotyping, extensive personal genetic information is expected to continue to be generated in large quantities in coming years. (Trager R S, *DNA sequencing. Venter's next goal:* 1000 *human genomes*, Science 298: 947 [2002]). The rapid growth in volume of available genomic and proteomic data has been characterized by substantial disorder and information obsolescence. For example, currently, the Gene Ontology (GO) consortium (Ashburner, M et al., *Gene ontology: tool for the unification of biology*. The Gene Ontology Consortium. Nat Genet 25: 25-9 [2000]) and the National Library of Medicine's MESH (Schulman J-L, *What's New for* 2001 *MeSH*, NLM Tech Bull. 317 [2001]) are two of the best-known ontologies in the bioinformatics domain Neither of these ontologies, however, currently contains the necessary information to support research about the relationships between genes and disease in the context of the human genome. While GO is well suited to classify a gene product in terms of its function, process and location, it has no terms to describe human diseases and the relations between them, whereas MESH, while rich in descriptions and classifications of human disease, contains no information about sequences, little information about genes, and no information about disease causing mutations and SNPs. This is an unfortunate situation, especially in light of the recent completion of the human genome sequence, and its annotation.

A key aspect of research in genetics is the association of sequence variation with disease genes and phenotypes. Sequence variation data are currently available, for example, from OMIM, HGMD (Hamosh A, et al., Online Mendelian Inheritance in Man (OMIM), a Knowledge base of human genes and genetic disorders, Nucleic Acids Res 30: 52-5 [2002]; Krawczak, M et al., *Human gene mutation database—a biomedical information and research resource*, Hum Mutat 15: 45-51 [2000]; McKusick V A, *Online Mendelian Inheritance in Man, OMIM (TM)*, McKusick-Nathans Institute for Genetic Medicine, Johns Hopkins [2000]) and others, both of which provide phenotypic information and describe amino acid variation. Unfortunately, in most cases these variation references do not provide sufficient information to support their direct mapping onto current genomic sequences and the associated annotated genes. Single nucleotide polymorphism (SNP) data are held in dbSNP and other publicly accessible databases. (E.g., Sachidanandam, R et al., *A map of human genome sequence variation containing 1.42 million single nucleotide polymorphisms*, Nature 409: 928-33 [2001]; Sherry, S T et al., *dbSNP: the NCBI database of genetic variation*, Nucleic Acids Res 29: 308-11.2001). While these databases contain millions of entries each including the position of the SNIP on the genome, they do not provide significant phenotypic information about the SNPs at the levels which need to be reached, namely from the genome to the phenotype and the clinic.

Moreover, as the volume of genomic and proteomic data grows there are requirements to synthesize vast amounts of information to enable clearer understanding of an individual's genetic profile. Patent application 20020052761 ("Method and system for genetic screening data collection, analysis, report generation and access", Fey, Christopher T.; et al.) describes a system for generating highly complex personal health reports to individuals concerning their genetic test results, based on an aggregate set of genetic markers and phenotypes.

Over the years most genomic and clinical advances have been published in scientific journals. Molecular biology advances and finding have been published predominantly in molecular biology journals (e.g., Cell, Nat Genetics, Am J. Hum. Genetics, etc.), and clinical phenotype related findings have been published predominantly in medical journals (e.g., N Eng J Medicine, Lancet, etc.). Because of these different journals are directed to different communities, large communication gaps have been created. Thus, there now exists in the public domain two distinct information resources, and neither is as valuable as it potentially could be because current research efforts require their integration. One part includes all large public genomic databases and the other is the vast amount of clinical research data, mostly held in publication, but increasingly accessible electronically. There is a clear tendency in the community for a computer-based classification of disease through ontologies and relating medical diagnostic classification schemes such as the ICD-9 with gene diseases (e.g., the NuGene project; Chisholm, R et al., *The Nugene Project* [2003]).

There are currently various standardization efforts occurring within molecular biology, most notably the gene ontology (GO) consortium efforts. (Ashburner, M et al., *Gene ontology: tool for the unification of biology. The Gene Ontology Consortium*. Nat Genet 25: 25-9 [2000]). Additional ontologies such as the sequence ontology, the mutation ontology and others are in work in process (for an overview of ontology development please see the "global open biological ontologies" (GOBO) web site (www.geneontology.org/doc/gobo.html).

Databases containing information on polymorphisms are also expected to have an important impact in the field of pharmacogenomics. Pharmacogenomics is an area of research focused on how variations in a patient's DNA can cause pharmaceuticals to respond differently. The importance of understanding these variations is underscored by the number of hospitalizations and deaths that occur each year that are caused by adverse drug reactions. One method of characterizing the genetic basis of drug response is by cataloging variations in drug response as a function of SNPs. The more SNPs cataloged, the more robust and effective the database. However, collecting and sorting the SNPs becomes a huge undertaking. In U.S. Patent application 20020049772, Reinhoff, et al, provides a broad overview of polymorphisms, pharmacogenomics, and classifying populations based upon sets of polymorphisms.

In addition to the scientific, technological and medical complexities that characterize the development and commercialization of genetic profile products and services, there are growing legal and regulatory complexities. For example, patient privacy has been a growing concern in multiple jurisdictions. In Europe, the European Union Directive 95/46/EC is designed to protect individuals with regard to the processing and movement of their personal data. In the United States, under the Health Insurance Portability and Accountability Act of 1996, commonly referred to as "HIPAA", regulations have been adopted that set forth "Standards for Privacy of Individually Identifiable Health Information". The purpose of these regulations is to help guarantee privacy and confidentiality of patient medical records. These Standard are quite extensive and apply to health care providers, insurers, payors and employers.

The confluence of all of the factors discussed above leads to the conclusion that what has been lacking from the art, but necessary for viable broad-based commercial provision of personalized health management products and services based on genetic profiling, is a method that satisfies the following requisites:
(1) the genotype of the individual to whom such products and services are being provided must be accurately and economically determinable at a large number of sites in that individual's genome relevant to a broad selection of different diseases;
(2) a large, dynamic, well-curated, database containing the associations between diverse genotypes and phenotypes must be maintained, easily accessed, and updated at very frequent intervals;
(3) for each individual to whom such products and services are being provided, the individual's genotype at each such site must be easily analyzed and filtered through such database to determine the individual's phenotype and construct the individual's genetic profile;
(4) the genetic profile so constructed for each individual and its implications must be easily communicated to the individual and the individual's physicians and medical/health care counselors in an effective manner that complies with health care, privacy and other laws and regulations.

Various means exist for practicing each of these separately. Each such means, however, suffers from various deficiencies, and a method of collectively optimizing their combined practice is required in order to provide health care management products and services on a broad commercial scale at prices that are economically attractive to both provider and customer. The present invention provides these and other benefits.

SUMMARY OF INVENTION

The present invention relates to a method for determining an individual's probability, whether enhanced, diminished, or average probability, of exhibiting one or more phenotypic attributes through evaluating genomic markers from that individual for zygosity for the members of a preselected set of genetic markers. In accordance with the method, the markers are compared to a multivariate scoring matrix to obtain a marker score, from which it is determined whether an enhanced, diminished, or average probability of exhibiting one or more phenotypic attributes is indicated. The multivariate scoring matrix correlates patterns of marker zygosity with probabilities of exhibiting phenotypic attributes.

The present invention is further directed to a method of selecting a set of genetic markers. The method involves filtering markers for inclusion in the set, based on a determination of measures of phenotypic value and/or prioritization, such as but not limited to, penetrance of the marker in a population or subpopulation of interest; the degree of linkage of the marker to a particular phenotype; the relative contribution of the marker to communicating the phenotype; and the degree of statistical or scientific confidence to be placed in any data associated with any of the measures of phenotypic value or priority used.

The present invention further relates to a method for providing relevant genetic information to an individual, or about an individual to another interested party (e.g., a physician, veterinarian, researcher, breeder, or owner). The method involves identifying genotypic characteristics of the individual that correlate with a relative probability of exhibiting one or more phenotypic characteristics. The method also involves determining for each of the one or more phenotypic characteristics whether the individual has an enhanced, diminished, or average probability, of exhibiting the characteristic by evaluating genomic markers for zygosity (for example, but not limited to heterozygosity or homozygosity) at each member of a preselected set of markers and comparing the zygosity of the markers to a multivariate matrix that correlates patterns of marker zygosity with probabilities of exhibiting phenotypic attributes, determining whether the marker score resulting from this comparison indicates an enhanced, diminished, or average probability of exhibiting the one or more phenotypic attributes. Then one or more selection criteria is applied for each of the one or more phenotypic characteristics. Each selection criterion applied imposes a total, a partial, or no limitation on the information communicated to the individual. Subsequently, information is identified that is relevant to the individual's probabilities of exhibiting the one or more phenotypic characteristics and is consistent with the limitations imposed by the selection criteria, and the information is communicated to the individual.

The present invention is further directed to a method of evaluating the genetic profile combination (i.e., "compatibility") of two individuals of the opposite sex (i.e., male and female) of the same species, whether human or a non-human species, in other words, a method of evaluating the probability that progeny of two individuals of the opposite sex will exhibit one or more phenotypic attributes. The method involves evaluating genomic markers from each of the two individuals for zygosity (for example, but not limited to marker heterozygosity or homozygosity) at each member of a preselected set of markers, determining a probability distribution for the zygosity for each member of the preselected set of markers in the genomes of the progeny of the two individuals, and comparing the probability distributions to a multivariate matrix to obtain a probability distribution score, wherein the matrix correlates patterns of marker zygosity with probabilities of exhibiting phenotypic attributes, and determining whether the probability distribution score indicates that the progeny of the two individuals have an enhanced, diminished, or average probability of exhibiting one or more phenotypic attributes.

The present invention further provides a method for determining the genomic ethnicity of an individual comprising evaluating genomic markers from an individual at each member of a preselected set of genetic markers, comparing the genotype for each of the markers to a multivariate matrix, wherein the matrix correlates patterns of genotypes with probabilities of examining phenotypic attributes, and determining the genomic ethnicity of individual as a pattern of the probabilities of exhibiting the phenotypic attributes.

The inventive methods can be used to provide individualized health management products and services based on an individual's genetic profile as well as for pharmacogenomic studies in human or other populations or subpopulations of varying sizes and compositions (e.g., members of defined ethnicity, gender, age, or disease or other physiologically abnormal condition, etc.). They can also be applied to the analysis and reporting of genetic profiles of various human populations and subpopulations, as well as populations and subpopulations of other non-human species.

Thus, the present invention provides the benefits of economical and effective genetic profiling that involves (i) genotyping each individual who seeks such products and services for a broad set of genetic variants, (ii) scoring these variants for their association with the individual's phenotypic susceptibility to the later onset of various diseases, (iii) providing information on such genotype and phenotype information in a manner that can be understood by the individual and the individual's physicians and medical/health care counselors so that appropriate health management steps can be taken prior to onset, (iv) tracking on-going advances in research tailored specifically for individuals based on the their genotypes and other personal information, and (v) providing information on these on-going advances to the individuals and their physicians and medical/health care counselors. The practice of the present invention is applicable to the provision of genetic profile-based health management products and services characterized by logistical efficiencies and economies of scale as well accuracy of analysis, interpretation and reports, and the effectiveness of such tracking of related scientific research and medical advances, and which can be offered in accordance with applicable health care, privacy and related laws and regulations. Moreover, the practice of the present invention is a valuable tool for pharmacogenomics.

These and other advantages and features of the present invention will be described more fully in a detailed description of the preferred embodiments which follows.

BRIEF DESCRIPTION OF THE DRAWINGS

FIG. 1 illustrates the way lexica, thesauri, and ontologies are used to semantically classify and define genomics data. (Modified from Ashburner M et al., *Gene ontology: tool for the unification of biology. The Gene Ontology Consortium*, Nat Genet 25: 25-29 [2000]).

FIG. 7 represents a portion of a MESH disease ontology ("C04"), which has been populated with human disease genes.

FIG. 9 shows an exemplary list of 2236 genes that can be included, in any combination of subsets, in a preselected set of markers in accordance with the invention.

DETAILED DESCRIPTION OF THE PREFERRED EMBODIMENTS

Figure 2:
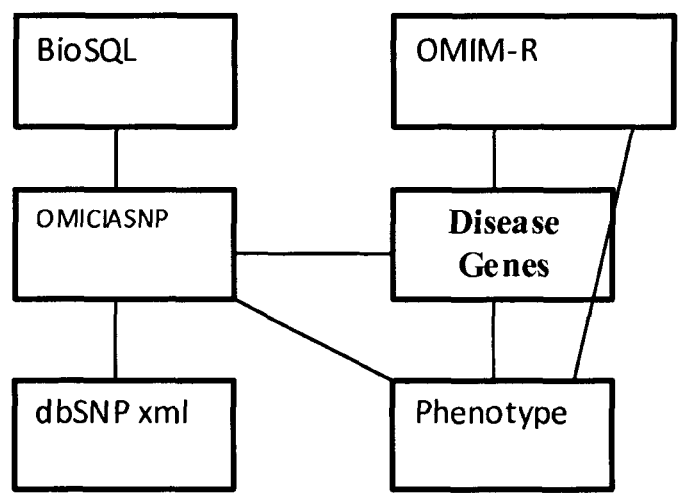
FIG. 2 illustrates database schematic of the invention.

The present invention relates to a method for determining whether an individual has an enhanced, diminished, or average probability of exhibiting one or more phenotypic attributes. In accordance with the method, genomic markers from an individual are evaluated for their zygosity at each member of a preselected set of markers.

For purposes of the present invention, an "individual" can be of any species of interest, including a human or a non-human species.

For purposes of the present invention, an enhanced, diminished, or average probability of exhibiting one or more phenotypic attributes, or a "relative probability," is with respect to the general population in a particular geographical area or areas, or with respect to a defined subpopulation thereof, for example, but not limited to, a particular gender, age grouping, or ethnicity, or some other identifying feature.

"Zygosity" of a marker is its genotype with respect to any combination of heterozygosity or homozygosity for one or more possible alleles at a locus, including, but not limited to, a condition of heterozygosity or homozygosity for a particular allele or alleles between chromosomes, or allele heterozygosity among several possible alleles at a locus on one chromosome.

In accordance with the present invention, the preselection of the set of markers is based on genotype/phenotype associations with disease conditions or predispositions for disease conditions. The association of genotypes with phenotypes and further associating such phenotypes with diseases and predisipositions includes utilization of existing data in the relevant literature and can also include data acquired from additional studies incorporating the practice of the present invention FIG. 9 shows an exemplary set of 2236 genes that can be included (in its entirety or in any combination of subsets) in a preselected set of marker in accordance with the invention. The skilled practitioner is aware of other markers that can be included in the preselected set of markers.

In one embodiment, preselecting the set of markers can be achieved using haplotype mapping to capture the majority of historic recombination events that have occurred since the most recent common ancestor of the sample group or population analyzed. An example of such a haplotype map is by the National Institute for Genome Research, which comprises a set of a few hundred thousand polymorphic markers covering the entire human genome with sufficient density along each chromosome to measure the diversity of common haplotypes prevailing in each local region. Nevertheless, haplotypes also can be defined as a block or region of DNA that has been inherited as a unit. SNPs within that block of DNA will also have been inherited together. These SNPs can then be used to identify the presence of a particular block. This block can have any size from a few base pairs to large hundreds of kilobases of nucleotides. (Stephens J C, Mol Diagn. 4(4):309-17 [1999]). In one embodiment of the present invention these markers are used to find common alleles or variants associated with complex diseases and are used to interpret local variation patterns and provide information on the evolutionary origin of known polymorphisms that are the cause of functional differences between alleles or variants. The markers are prioritized in order to construct or "preselect" a reduced marker set to avoid the data management and statistical problems that attend whole genome scans using hundreds of thousands of genetic markers simultaneously. In a preferred embodiment of the present invention, certain genotypes are associated with certain phenotypes.

In another embodiment, the predicted and/or measured effect of different genetic markers on the DNA/RNA sequence changes that occur in the splicing process at exon/intron junctions is used to classify and preselect the set of genetic markers. Such classification can be accomplished by scoring each genetic marker candidate through the application of one or more predictive models applied to the data in a multivariate scoring matrix for that candidate. In this embodiment, all splice sites relevant to a variant are first identified by mRNA identification and alignments to the genomic DNA either through existing annotations or new annotations, thereby enabling both information and chemical retrieval of 5' and 3' splice site sequence regions. Second, variants with SNPs within these splice site regions and the associated sites are identified by the integrating and mapping of public and private mutations within these splicing associated sites. Third, the wild-type or original sequences and the mutated sequences are scored with one or more predictive models selected from the universe of: statistical models, such as weight matrix, Bayesian, hidden Markov models, semi- or general hidden Markov models; artificial intelligence models; and discriminative and predictive models related to binding affinity. This process results in splicing strength scores for the original variant and the variant with the SNP. The difference of these scores of any other metric applied to these scores can then be used to preselect markers for genotyping analysis and to score, rank, and prioritize factors in the construction of a multivariate scoring matrix.

In one embodiment of the present invention, the preselected set of genetic markers comprises a plurality of exon/intron junction sequences. In another embodiment of the present invention at least about 20% of the genetic markers in the preselected set of genetic markers are exon/intron junction sequences. In another embodiment of the present invention at least about 40% of the genetic markers in the preselected set of genetic markers are exon/intron junction sequences. In another embodiment of the present invention at least about 60% of the genetic markers in the preselected set of genetic markers are exon/intron junction sequences. In another embodiment of the present invention at least about 80% of the genetic markers in the preselected set of genetic markers are exon/intron junction sequences.

In addition to applying predictive models to such splice sites for purposes of preselecting genetic markers and for constructing genotyping assays, such predictive models can also be applied for such purposes to large-scale promoter regions of genomic DNA that can contain one or more SNPs, functional binding sites within the 5' or 3'untranslated regions ("UTRs"), RNAi-genes, and mRNAs. In a preferred embodiment of the present invention, a method is provided of subjecting genetic markers within promoter regions to the same analytic selection process as specified above for splice sites. In one preferred embodiment of the present invention, the preselected set of genetic markers comprises a plurality of promoter sequences. In another preferred embodiment of the present invention, at least about 20% of the markers in the preselected set are promoter sequences. In another preferred embodiment of the present invention, at least about 40% of the markers in the preselected set are promoter sequences. In another preferred embodiment of the present invention, at least about 60% of the markers in the preselected set are promoter sequences. In another preferred embodiment of the present invention, at least about 80% of the markers in the preselected set are promoter sequences.

In another embodiment of the present invention, genetic markers of interest are identified and selected for inclusion in a preselected set, based upon a matrix with dimensions comprising genotypic and phenotypic criteria. These criteria can include, among others: base pair sequence homology to another known genetic marker sequence of interest; the presence of two or more regions of DNA on the same chromosome or genetic marker (synteny); relevance to the description of the molecular function, biological process and cellular component of the protein coded by the gene under investigation (ontology) and ontological classification; conservation of mutated sequence sites at conserved or less conserved sequence homology sites in the genome; quality of research on the genotype, genetic marker and phenotype under investigation; biological significance of the genetic marker (for example, whether the marker specifies a protein coding change); and regulatory value and classifications of the amino acid(s) specified by the genetic marker.

"Lexica", "thesauri", and "ontologies" are used to semantically classify and define genomics data. A "lexicon" is a list of terms belonging to the same semantic class: BMP4 and DPP, for example, both belong to the semantic class of "BMP" (i.e., bone morphogenetic factor). A "thesaurus" provides a listing of the synonyms for a term, or semantic class, and hierarchical "ontologies" are used to "define" the terms contained in a lexicon and a thesaurus. Long a cornerstone of computer science, ontologies have recently become a major focus of research in bioinformatics. Like controlled vocabularies, ontologies also enable data sharing but, because they contain hierarchical relationships between their terms, ontologies enable logical inference and deduction (see FIG. 1) on the data they contain, making them powerful tools for hypothesis generation. The definition of a term is produced by tracing the path from a term to the root of the ontology (FIG. 1, panel c, path starting from "BMP"). The simple ontology shown in panel c of FIG. 1, for example, defines "BMP" as "a TGF-β growth factor". Definitions apply to all members of a semantic class and their synonyms, and can be used as a basis for logical inference: e.g., "DPP is a DVR, a DVR is a BMP, a BMP is a TGF-β, and a TGF-β is a growth factor"; therefore it can be inferred that "DPP is a growth factor" even if no document explicitly states this fact. Note that the ontology shown in panel c of FIG. 1 is a particular type known as an 'isa-hierarchy'; other types of ontologies exist, not all of which are suitable for definition.

In one embodiment the selection of markers is based on microsatellite markers. Microsatellite include simple sequence repeats, short tandem repeats and simple sequence length polymorphisms that are characterized as relatively short tandem repeat nucleotide sequences, e.g. (TG)n or (AAT)n, generally less than 5 base pairs in length. Microsatellite markers have adequate physical densities for family-based (linkage) studies where the number of recombination events between closely related family members is small, hence markers even as distant as mega bases apart are likely to be co-inherited. In addition, microsatellite markers are generally useful in genetic studies because of their hypervariability, co-dominance and reproducibility of microsatellite markers.

The present invention is also directed to a method of selecting a set of genetic markers which can be employed, for example, in preselecting the set of genetic markers in accordance with the method for determining whether an individual has an enhanced, diminished, or average probability of exhibiting one or more phenotypic attributes. Selection of a set of genetic markers according to the present invention results in large set of genetic markers that map to splice site regulation loci and promoter loci for gene clusters and gene families associated with specific phenotypes as well as complete genome-wide splice site and promoter site genetic marker profiles.

Selecting the set of genetic markers is optimized by a meaningful marker prioritization which requires the incorporation of additional facets of information to characterize the local genome context. One useful approach is to employ existing lists of candidate genes thought to be involved in a given disease. By computational mining of the disease literature, identifying sets of genes already implicated in related clinical phenotypes (or homologous genes involved in related phenotypes in model organisms), and by locating disease loci and disease-causing mutations within the common frame of reference of the genome sequence one can hope to extend these lists. Although extended, such lists still drastically limit the number of loci one needs to scan for disease association, while they are, hopefully, still inclusive enough to reduce the risk of omission of true causative loci. Within the targeted regions, typically a gene locus, one has the choice of either including all known polymorphic markers, or trying to make further reductions.

Some other useful considerations include marker location relative to the functional units of the gene (coding, UTR, splice site, regulatory, intron, etc.), marker zygosity (related to population frequency), or ease of assay development (local repeat structure, sequence composition for oligo design). Typically, focusing on extended candidate lists reduces the DNA search space from the entire genome to about one thousand to a few thousand loci, or roughly 5% of the genome. Additional pruning can introduce an additional 5-fold reduction. The result is a scenario where, at the cost of genotyping 1% of all the markers available for a genome-wide scan, one types all candidate loci, with the reasonable expectation that at least half of the causative loci are investigated. In addition to the reduction in genotyping cost, an advantageous reduction of false positive associations results, which false positive associations have been known to plague even very large clinical association studies and have been cited as an important cause of irreproducible reports of disease association.

In a preferred embodiment of the present invention, the preselected set of markers comprises genetic markers that map to at least about 1,000 discrete loci. In another preferred embodiment of the present invention, the preselected set of markers comprises genetic markers that map to at least about 2,000 discrete loci. In another preferred embodiment of the present invention, the preselected set of markers comprises genetic markers that map to at least about 3,000 to about 5,000 discrete loci. In another preferred embodiment of the present invention, the preselected set of markers comprises genetic markers that map to at least about 5,000 to about 10,000 discrete loci. In another preferred embodiment of the present invention, the preselected set of markers comprises genetic markers that map to at least about 10,000 to about 15,000 discrete loci. In another preferred embodiment of the present invention, the preselected set of markers comprises genetic markers that map to least about 15,000 to about 30,000 discrete loci.

In accordance with the invention and the method for determining whether an individual has an enhanced, diminished, or average probability of exhibiting one or more phenotypic attributes genomic markers corresponding to at least the preselected set of genetic markers from an individual are evaluated for zygosity. For purposes of the present invention, zygosity for a marker is detected in a biological sample collected from the individual that contains the individual's genomic DNA (such as, but not limited to, a blood, saliva, or tissue biopsy sample, which biological sample can be freshly collected or suitably stored to preserve the DNA) by employing suitable biochemical genotyping analytical assay means. Analytical hybridization or polynucleotide sequencing means are typically employed, optionally after amplification of DNA in the biological sample, for example, by using PCR-based amplification means. High throughput analyses can optionally be achieved by multiplexing techniques known in the art. The genotyping analytical assay means can optionally be performed with commonly available robotic apparati and/or very dense array detection apparati.

The determined zygosity of the markers for the individual is compared to the multivariate scoring matrix to obtain a marker score, wherein the multivariate scoring matrix correlates patterns of marker zygosity with probabilities of exhibiting phenotypic attributes. In accordance with the invention, the multivariate scoring matrix correlates patterns of marker zygosity with probabilities of exhibiting phenotypic attributes, based on scoring matrix vectors that can include descriptors of: family history, general medical physiological measures or values (such as, but not limited to, cholesterol levels, triglyceride levels, blood pressure, heart rate, HGH or other hormone levels, red blood cells, bone density, CD scan results, etc.), mRNA expression profiles, methylation profiles, protein expression profiles, enzyme activity, antibody load, and the like. The comparison with the multivariate scoring matrix can be done manually or, preferably, by employing a suitable computer software instantiation in which the multivariate scoring matrix is algorithmically constructed and manipulated via a programming language, for example, but not limited to, Java, Perl, or c++.

Based on this comparison it is determined whether the marker score indicates an enhanced, diminished, or average probability of exhibiting one or more phenotypic attributes, relative to a reference population, e.g., the general population of a chosen geographical area, or another chosen subpopulation thereof in terms of ethnicity, gender, age, or other identifying feature of interest.

The present invention further provides a means for providing relevant genetic information to an individual whose genetic profile has been determined in accordance with the present invention.

The method for providing relevant genetic information to an individual, and for generating information reports to be communicated, includes identifying the individual's genotypic characteristics by correlating those genotypic characteristics with a relative probability of exhibiting one or more phenotypic characteristics and determining for each of the one or more phenotypic characteristics whether the individual has an enhanced, diminished, or average probability of exhibiting the phenotypic characteristic, in accordance with the present invention as described hereinabove.

The method for providing relevant genetic information to an individual then includes applying one or more selection criteria for each such phenotypic characteristic, wherein each selection criterion imposes total, partial, or no limitation on the information communicated to the individual, identifying information that is relevant to the individual's probabilities of exhibiting such phenotypic characteristics and consistent with the limitations imposed by the selection criteria, and communicating the information to the individual in a report as described above.

In one embodiment of the present invention, the same or different selection criteria are applied one or more additional times to the determined probabilities of exhibiting each of the phenotypic characteristics, information is identified that is relevant to the individual's probabilities of exhibiting the one or more phenotypic characteristics and consistent with the limitations imposed by the selection criteria, and the information is communicated to the individual.

In one embodiment of the present invention, at least one of the selection criteria is specified in advance by the individual.

In another embodiment of the present invention, at least one of the selection criteria is a function of the availability of treatments effective to modify the phenotypic characteristic.

In other embodiments, at least one of the selection criteria is a function of the scope and quality of known research relating to the phenotypic characteristic; or at least one of the selection criteria is a function of the probability determination(s) for one or more other phenotypic characteristics.

The information is then communicated to the individual, whether directly, or indirectly via an appropriate intermediary, in a report that generally includes an explanation of relevant terminology; a summary of the genetic profile of such individual subject; an explanation of each genotype assay performed on biological samples from the individual, typically as categorized by types of disease (such as, but not limited to, cancer, cardiovascular disease, and the like), and in relation, where applicable, to specific body organs, tissues and metabolic, reproductive or other bodily functions and systems; a summary and detailed results for each such genotype assay performed; a health risk appraisal for such individual subject; general information about genetics and genomics; and references for further information. Such report can include summary sections of genes and gene families important to individuals based on their specific phenotypic impact and the demographic, ethnic, gender, age, and related characterizations of each individual. For example, the categories for such characterization can include, but are not limited to, aging, women's health, and drug interactions. These summaries can include (i) an assessment of the overall genetic health of the individual in each health category presented and the overall genetic health of the individual and (ii) cross references to the more detailed information within the report.

The information report can be communicated orally, but is preferably communicated in a documentary format, whether written or electronic, and in any suitable order of report presentation. Prior to communicating the information to the individual, the information is preferably, but not necessarily, formatted to present the relevant phenotypic attributes according to an organizational matrix, wherein the organizational matrix determines the grouping and presentation of information to the individual. More preferably the organizational matrix groups the various phenotypic characteristics for which the individual has an enhanced probability together. In some embodiments the organizational matrix groups phenotypic characteristics related to similar physiological systems together. In other embodiments, the organizational matrix ranks the phenotypic characteristics as a function of the potential impact on the individual's lifestyle or quality of life, or the organizational matrix ranks the phenotypic characteristics as a function of the "genomic ethnicity" of the individual, as described herein.

In a preferred embodiment of the present invention, the information report relates to a broad selection of diseases. Such diseases may include, among others, cancer and those relating to the following organs, tissues, and metabolic, reproductive and other bodily functions and systems involved in human health, including, but not limited to, cardiovascular, respiratory, kidney and urinary tract; immune system, gastrointestinal, neurological, psychoneurological, and hematological functions and systems.

In a preferred embodiment of the present invention, the report for each such disease, disorder and other adverse medical condition comprises information about the relevant genes, the sites assayed in such gene, the clinical association of variants at such sites with relevant disease, the genotype of the individual subject at each such site, information about the association of such genotype with the phenotype associated with such disease, and information about drug interactions for the individual subject based on such genotype.

Prior to communicating the information to the individual, the identity of the individual need not be associated with the data corresponding to the genotypic characteristics, the relative probabilities of exhibiting the phenotypic characteristics, or the identified relevant information A suitable coding or "blind" system can be employed to shield the identity of the individual, if appropriate.

The present invention provides that the format and substance of the information report can be modified from time to time on an ongoing basis, particularly in response to questions from individuals, physicians and medical counselors about genetic markers, genotypes, genotype assays, the association of genotype with phenotype and diseases, and other aspects of such reports. In a preferred embodiment of the resent invention, such questions are stored in a database and the overall effectiveness of communication of the text and graphics presented in such reports are from time to time assessed. In a preferred embodiment of the present information, the report generator is constructed so that changes to the information report format and substance can be effected efficiently and economically.

The present invention also relates to a method of evaluating the genetic profile combination (i.e., "compatibility") of two individuals of the opposite sex of the same species, in other words, a method of evaluating the probability that progeny of two individuals of the opposite sex will exhibit one or more phenotypic attributes. The method is applicable to providing genetic counseling to pairs of individuals of the opposite sex relating to preselected risks engendered by their respective genotypes, or genetic profiles, to their progeny, whether prospectively or after the birth of the progeny. Alternatively, the method is applicable to providing genetic counseling to a recipient parent (or recipient parents) of progeny resulting from, or intended to result from, the use of donor gametes, e.g., donor sperm and/or ova.

The method involves evaluating genomic markers from each of the two individuals whose gametes are to contribute, or contributed, to the genetic inheritance of the progeny by the formation of a zygote, i.e., the genetic or so-called "biological" parents. Zygosity at each member of a preselected set of markers is evaluated, and a determination is made of a probability distribution for the zygosity for each member of the preselected set of markers in the genomes of the progeny of the two individuals. The probability distributions are compared to a multivariate matrix to obtain a probability distribution score. The multivariate matrix correlates patterns of marker zygosity with probabilities of exhibiting phenotypic attributes, as described hereinabove. Then it is determined whether the probability distribution score indicates that the progeny of the two individuals would have an enhanced, diminished, or average probability of exhibiting one or more phenotypic attributes.

The present invention further provides a method for determining the genomic ethnicity of an individual for the purpose of determining the likely applicability of clinical research results based upon the genetic profile of the individual. Clinical research results are often only found in particular populations or subpopulations, and these results are frequently correlated with the ethnicity of the population or subpopulation. "Genomic ethnicity" means a genetic profile of an individual having a distribution of genetic markers in a preselected set of markers, based on genotype/phenotype associations with disease conditions, that is preponderantly consistent with the distribution of those markers that is determined to be or is known in the art to be characteristic of a particular ethnic population or subpopulation. The determination of genomic ethnicity in accordance with the method can often provide more useful information than an individual's mere self-reporting of ethnicity.

The method involves evaluating genomic markers from an individual at each member of a preselected set of markers, comparing the genotype for each of the markers to a multivariate matrix, wherein the multivariate matrix correlates patterns of genotypes with probabilities of exhibiting particular phenotypic attributes, and determining the genomic ethnicity of the individual as a pattern of the probabilities of exhibiting the phenotypic attributes.

In should be borne in mind that the genotype-phenotype relation requires two axes, the phenotype (e.g., a particular disease) and the mutations. Most known disease-causing mutations are found in single-gene disorders because these have been the easiest to find; Most of the OMIM disease entries are in this class; hence most OMIM mutations cause single-gene disorders. These disorders are usually very rare in the general population (although can be much more prevalent in a given family or population group). For diseases in this group, allele state often predicts disease with an almost certainty. But there are more complex scenarios: (i) with the current state of knowledge, genotype-phenotype association can only be cast in statistical terms (i.e. having the "bad" allele does not necessarily mean the individual will ever develop the disease, but means a heightened chance or predisposition, relative to the general population or a defined subpopulation, of developing it in the future), or (ii) the association is only seen in some studies but not in others, or (iii) the association is only seen in a single family, in a population isolate, or one of the world populations, with no knowledge of relevance for other populations. Also typical in these cases is that the associated marker is almost certainly not itself causative, merely an associated marker for the disease. In accordance with the methods of the present invention, each of these scenarios are taken into account as appropriate in constructing the multivariate matrix, or multivariate scoring matrix, and as the available information improves concerning genotype/haplotype relationships with a given phenotype, the multivariate matrix, or multivariate scoring matrix, can be updated, expanded, thereby enhancing its predictive value when employed within the inventive methods. However, the practice of the inventive methods is not limited by the precise contents of the multivariate matrix at any given time, which will vary as new information is incorporated.

The information about the genetic profiles of individuals for whom genetic profiles have been generated of the type produced in accordance with the present invention can facilitate delivery of appropriate therapies to the individuals, can enable the further identification of novel genotype-phenotype relationships to support the discovery of new therapies, and can provide novel indicators of health. Thus the present invention can be applied to pharmacogenomic analysis and the development of more effectively directed drug therapies.

In another application, the information generated in accordance with the present invention can be maintained in an updatable database. The database can be constructed using widely available database management tools, such as Oracle or open source database tools such as postgres. The information in the database can be used to select individuals for whom investigational therapies or newly commercially available therapies could probably be most effective, based on their genetic profiles. For example, such selection can be made positively on an indication that individuals with a disease or predisposition to disease can benefit from particular therapies, or negatively on an indication that such individuals are at risk with a particular therapy. Such classification schemes can be used to identify subsets of populations with complex disease for purposes of course of therapy decisions.

EXAMPLES

Example 1

Use of a Genetic Marker as an Index to Literature

A genetic marker, and a variant found at that marker, can be characterized by a number of factors. These can include a unique sequence surrounding it, a fixed offset from a known reference sequence point, or a specific amino acid change in a particular protein. The clinical literature refers to markers, mutations, or polymorphisms in a variety of different ways. In accordance with the present invention, individual markers and variants can be characterized using these and other attributes in order to use them to index clinical literature. This index can be constructed of a single marker, or of a set of markers. By indexing literature in this way, a consolidated report can be constructed based upon these markers. If for example, there exists a genotyped, or sequenced database of markers that have been found to be present in an individual, this marker database can be used to create an extract of clinical literature that is particularly relevant to the individual. This use of an individual's markers or variants as a literature index, is a useful component in providing personalized communication of information from literature and other databases, based upon an individual's genetic profile.

Example 2

Association Representation

As genetic disease associations become more complex, interpreting the implications of these associations becomes more complicated. The overall quality of the association, in a number of dimensions, becomes increasingly important. In addition, in order to understand the importance of a particular association to an individual, an association, in all of its texture, needs to be viewed in the overall context of the individual's genetic profile. Characterizing and representing this quality, both independent of the individual and in the context of the individual's genetic profile become fundamental to the appropriate usage of the information.

The factors that shape the implications of a genetic association are diverse. They range from the causal linkage seen with the association (e.g., the percentage of disease cases that are associated with a particular association and the percentage of individuals with a given marker who develop the disease), to factors related to the breadth of the research (e.g., number of studies, number of individuals studied, and number of ethnicities studied). By characterizing and representing the associations in this manner, individuals, their counselors, and their health care providers can better understand, appropriately value, and make use of them.

One method of representing the quality of an association, for the purposes of analyzing, evaluating, determining, identifying, comparing, or formatting the information and/or of communicating or presenting the information to the individual, is to place associations on a two dimensional grid. The axes of this grid would be the percentage of disease cases that are associated with a particular association and the percentage of individuals with a given marker who develop the disease. Each association would be represented, e.g., by a colored circle, on this grid; the color can represent the number of studies of this association, with for example, red representing a low number, yellow representing an intermediate number and green representing a large number of studies. The darkness of the circle can represent the number of ethnicities studied, and the size of the circle can represent the number of individuals. In this way, at a glance, a viewer can understand how a particular association compares to others, and the overall quality of the association itself. For example, a light, red, circle close to the origin is a very weak association. A dark, green circle in the top right of the graph is very significant, well-studied in large populations.

The same graph can be constructed of associations for those markers that have been found in an individual's genetic profile. With this, an individual or his or her counselor or health care provider is immediately focused on those associations that are most significant.

Of course, this multi-dimensional representation can take many graphical forms. An alternative method might use a radar graph. A radar graph is a two dimensional polar graph that enables one to simultaneously display many variables. It does this by plotting each variable along a different radial axis emanating from the origin of the polar plot. If one has ten variables, then there will be ten radial axes thirty six degrees apart Small values are near the center of the polar plot and large values near the outer circumference. An experiment might result in multiple measured variables and the investigator wants to compare the results of this experiment repeated under different conditions. If one connects the variable values on each radial axis with a straight line then a distorted star-like pattern (or "polygon") is created. One can then visually compare the patterns created by the lines representing the different conditions for the experiment. In addition, several polygons can be plotted on the same set of radial arms through the use of one color or line pattern per polygon.

The preceding are illustrative, and not exhaustive examples, of how graphical representation of a number of factors that characterize a genetic association can support an enhanced understanding of the association, both individually and in the context of other associations, as well as independently and in the context of an individual's genetic profile.

Example 3

Characterizing Patterns of Associations Found in an Individual's Genetic Profile Genetic profiles, defined as a set of markers found in an individual's genome ranging from a small set of markers to the entire genetic sequence, are used to generate or predict attributes of individuals that can be used for a variety of applications. These applications can range from identity verification to determining disease predisposition and drug interactions to feature prediction (e.g., height, hair color or eye color). In addition, the attributes can range from being absolutely correlated to the genetic profile, to being shaped by the genetic profile, to being unpredictable from the genetic profile. Understanding and characterizing the degree to which a genetic profile specifies an attribute has great utility. For example, the generation of a profile from DNA of a suspected criminal is much more useful when the degree to which the feature can be predicted is well-understood. If red hair is almost assured, but height much less specified by the profile, searches can be better refined. Capturing and representing this information becomes much more important as the number of attributes to be analyzed grows. The methods that can be used to extract and capture these patterns include statistical models, Bayesian networks, hidden Markov models, and other machine learning techniques.

Example 4

Constructing Multivariate Matrix

A goal of the present invention is to bridge the time gap that currently exists between the latest research advances and the final benefit to the consumers in the health care system. Through genetic testing and the information delivery this gap can be bridged and shortened by a huge factor. For example, individuals can be tested for a newly identified functional polymorphism (e.g., the RANTES gene; Hizawa, N. et al., *A functional polymorphism in tile RANTES gene promoter is associated with the development of late-onset asthma*, Am J Respir Crit Care Med 166: 686-90 [2002]; see Table 1 below), information about which can be added to the multivariate matrix, or multivariate scoring matrix in accordance with the present invention. Suitable genotyping assays can be developed for the newly identified polymorphisms described in the original article in a matter of weeks. After the genetic testing with the genotyping assay, the result can be communicated to the tested individual about her or his genetic profile and the relevant clinical phenotype information like specific risk factors—in the RANTES gene example its relationship with asthma—that are correlated with a specific genetic profile. The complexity of the clinical information for the RANTES gene is not limited to this article but there exist many more articles describing the relationship between genetic markers in the RANTES gene and a clinical phenotype. One useful database to capture more comprehensively genetic literature information concerning a disease can be found in the "Online Mendelian Inheritance of Man" (OMIM) database (Hamosh, A et al., *Online Mendelian Inheritance in Man* (OMIM), *a knowledgebase of human genes and genetic disorders*, Nucleic Acids Res 30: 52-5 [2002]; McKusick V A, *Online Mendelian Inheritance in Man, OMIM* (TM). McKusick-Nathans Institute for Genetic Medicine, Johns Hopkins [2000]). The OMIM database contains textual information and references on inherited diseases and genetic disorders. It also contains copious links to MEDLINE and sequence records in the Entrez system, and links to additional related resources at NCBI and elsewhere. This database is accessible on the internet at the ncbi website with the extention nlm.nih.gov./entrez/query.fcgi?db=OMIM, as well as in a hard copy book. The electronic version is also distributed in XML format under an NIH license from the National Library of Medicine. While the OMIM database is very useful for clinical and academic research it is still far too technical for an individual and her/his healthcare provider (see as an example the OMIM entry for the RANTES gene in Table 2 below).

A prototype system was developed that allows scientists to position alleles described in the Online Mendelian Inheritance in Man (OMIM) database on the build 33 assembly of the Human Genome from the National Center for Biomedical Information (NCBI). Once placed on the assembly, the system automatically classifies the alleles within the context of a gene and its genomic structure; i.e., coding (synonymous/non-synonymous), UTR, etc. The OMIM database is currently the most comprehensive and relevant database for human genetic disease, and we have therefore focused our efforts on mapping the OMIM alleles to the genome. Toward this end we have developed a 'deterministic' algorithm for OMIM allele mapping. Most of the alleles described within OMIM are clinically relevant, and have links to the appropriate scientific publications; in an attempt to better manage the clinical data associated with these alleles, we have also developed a concise and high-level disease ontology.

All five subsystems of the prototype system have been tested with a set of known, well-characterized disease genes. Specific care and focus have been given to the user-friendliness and user interaction of the annotation station, an extendable and flexible design for the database infrastructure and a practical approach for the OMIM allele mutation mapping algorithm, to capture as many OMIM mutations within the genome as possible, by avoiding false positives. During the genetic disease ontology development, we largely made use of existing medical textbook classifications, due to the widespread familiarity of these classifications within the medical community. The following sections detail the software and the science developed.

(a) Prototype Visualization Annotation Station

We built a prototype SNP and mutation oriented genome annotation station, in which we leveraged existing open source genome browser software as developed in the wormbase project (Stein, L. et al., *WormBase: network access to the genome and biology of Caenorhabditis elegans*. Nucleic Acids Res 29: 82-6 [2001]). For additional data manipulation work we have used PERL code from the open source BioPerl project (Stajich, J E et al, *The bioperl toolkit: perl modules for the life sciences*, Genome Res 12: 1611-8 [2002]). The annotation station is centered on genes, and with a gene symbol the genomic region for the specified gene can be viewed.

Figure 8:
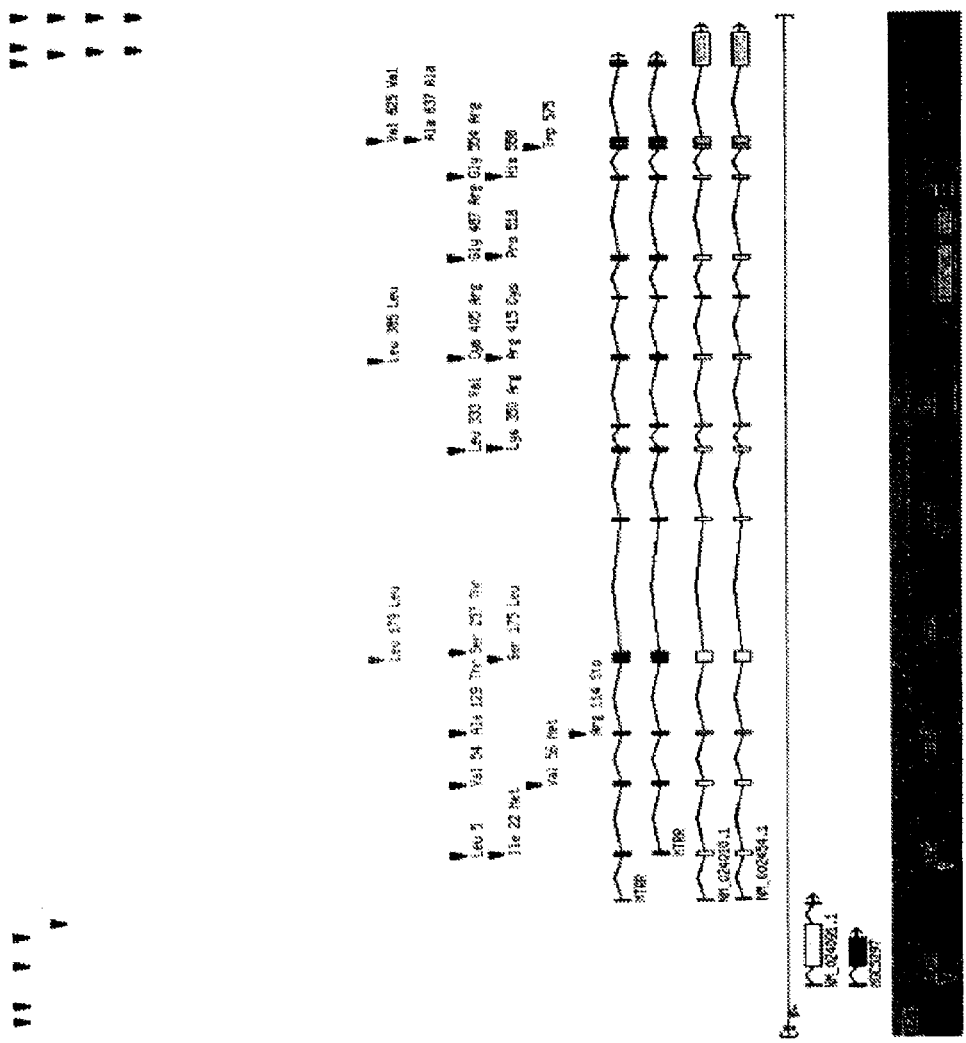
FIG. 8 shows a variation map for the MTRR gene. Nonsense coding mutations are shown in dark arrows (e.g., "Arg114Stp"), missense coding mutations are shown in grey arrows (e.g., "Ile22Met") and silent mutations are shown with light grey arrows (e.g., "Leu179Leu"). Intronic mutations are shown with light grey arrows and upstream and downstream mutations within ±5 kb are shown with black arrows at the top of FIG. 8 (original code from Stein L et al., *WormBase: network access to the genome and biology of Caenorhabditis elegans*, Nucleic Acids Res 29: 82-6 [2001]).
Figure 11:
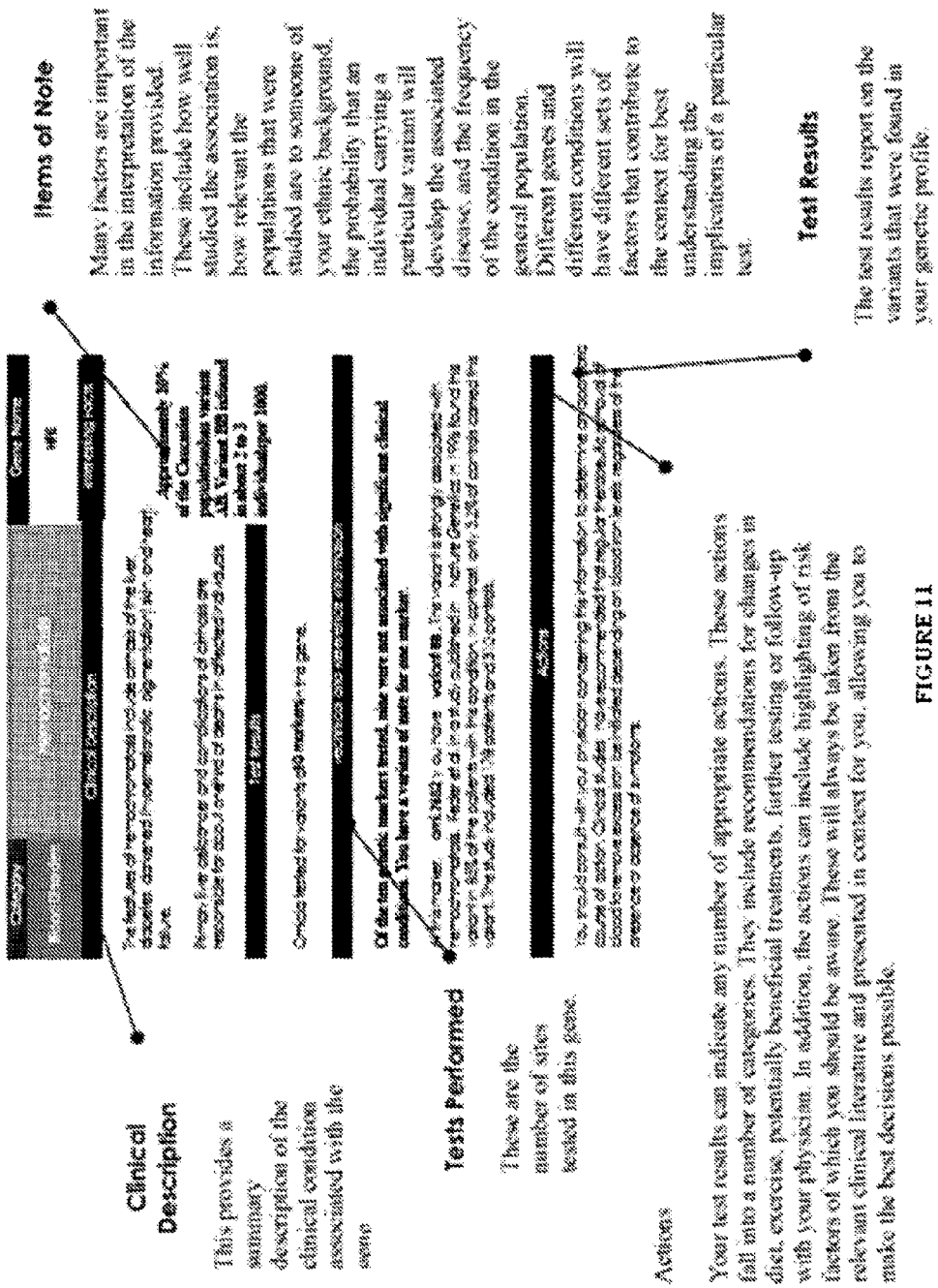

Our "GeneViewer" can display different types of genomic sequence variations within a graphical user interface. The display now shows graphically a genomic gene region with 5 kb sequence upstream and downstream of the start and stop codon of a gene. It also displays neighboring genes that are located within this +/−5 kb window. The gene structure is displayed using the "traditional" exon-intron viewer, in which exons are linked with arcs that span the introns. Currently the display color-codes and groups missense, nonsense, coding and non-coding mutations onto the gene structure. The variation symbols list the nucleotide and/or protein amino acid change in a small text glyph. A variation map screen shot of this GeneViewer can be seen in FIG. 8, which shows the MTRR gene.

Following the GeneViewer is a short "Gene Summary", which tabulates all the general information about a gene, such as NCBI's LocusLink identifier(s), genomic Genbank records, RefSeq links, full textual gene names as well as internal disease classifications from our Ontology (see below) that are assigned by the annotators.

Following the Gene Summary is the "Variation Summary", which seeks to list in table format all known genetic markers within this gene from different mutation databases. This table currently lists OMIM alleles and dbSNP entries including there sequence position within the genomic sequence as well as the protein sequence; Furthermore, codon position, codon changes, and a short functional characterization (missense, non-sense, exonic, intronic, 5'UTR, 3'UTR, upstream or downstream) are included. A snapshot for the MTRR gene can be seen in FIG. 8.

In the next two sections, the "mRNA Summary" and the "CDS Summary", raw mRNA and coding sequences (CDS) including the Genbank annotations. On demand, the genomic sequence can also be displayed.

The "Protein Summary" follows, which besides the translated coding region lists under the wild type sequence the protein mutations caused by the sequence variation lists in the Variation Summary table. This is very useful, because for each occurring nucleotide change the resulting protein mutation can be seen.

At the end of each gene page, the corresponding OMIM entry is listed from a local OMIM copy from our database to avoid the reloading of every OMIM entry from the NCBI site through the internet ("OMIM Summary"). This allows the annotators to review the verbal gene annotation within the same display.

The data required for effective and accurate annotation are diverse. To address this diversity, the visual annotation station is split into these different views. The prototype also allows to add other information sources and even to generate new summary views if necessary. Improvements can be added, including various hyperlinks with the interface, that can link to external (NCBI: dbSNP, RefSeq, Genbank) as well as internal sources (OMIM, filtered version of PUBMED; see text mining algorithms below). For example, this can be addressed by downloading the OMIM database from the NIH and incorporating the OMIM locus entries within the genome annotation station. This allows to cross-link mutations within a gene document and get fast access to the allele variation description in OMIM on the same page.

(b) Prototype Annotation Pipeline Software

We have built a selection of PERL scripts to download the latest human genome assembly as well as annotations from Genbank and RefSeq. The current prototype system has loaded the build 33 assembly, but is easily updated. Furthermore, dbSNP and the OMIM databases have been licensed and downloaded from the NCBI ftp site.

To capture and identify all known human genes predisposing to disease, we have begun with a widely accepted, recently published paper tabulating and summarizing all known human disease genes (Jimenez-Sanchez, G et al., *Human disease genes*, Nature 409: 853-5 [2001]). This set consisted of the non-somatic genetic associations contained in the OMIM database. This set of 923 human disease genes was expanded with a collection of genes derived from an in-house analysis of hundreds of current clinical research papers, selecting those associations that were most significant and "actionable" by the clients of our service. Any hint of an association between a novel disease gene and a clinical phenotype within an abstract triggered the collection of the paper from the library or online databases. The original papers were then reviewed and if significant, the gene was manually added to our collection of disease genes. Additional papers that justify the selection of a certain gene into our disease gene set were noted as additional evidence. A broad disease classification scheme (see "high-level disease ontology section") was developed during this process as well. The total number of genes in our system is currently 1,732. Given that the current estimate of the total number of human genes is between 25,000 and 30,000, this would mean that between 5.5% and 7.0% of human genes can be classified to be disease related. Of course, this is only a snapshot of the current clinical research and we expect the percentage to increase over time. 98% of these genes already had OMIM entries.

Of the 1,732 hand-selected genes, only 1,614 could be uniquely located in the latest genome assembly (see Table 3). The remaining 118 genes were either annotated at multiple loci within the human genome or were missing from both RefSeq and Genbank. The location of these 118 genes within the human genome sequence is next to be manually determined, as many belong to small paralogous families that have significant clinical implications.

During the loading process of the flat file OMIM entries, we have parsed out the OMIM allele identifiers. It has been very difficult to develop this PERL parser due to the incredible mixture of formats for allele annotations. The allele identifiers have then been used to locate the protein mutations within the human genome assembly and the Genbank annotations. As can be seen in Table 3, 57.29% of the OMIM alleles could be localized directly within the genome assembly through the Genbank annotations using only the protein variation allele identifiers. This procedure of comparing OMIM alleles with the Genbank annotations is a quality check for the Genbank annotations. The main reason why not all of the OMIM alleles could be easily mapped to the genome has primarily to do with the different protein sequences, in which the first mutations have been described Case studies for some of these genes have shown that the underlying protein sequence has usually been extended on the 5'end of the coding sequence over time. In previous publications only the 3' part of a gene sequence has been known—typically because of the early 3' EST sequencing efforts—and old, incorrect amino acids variation annotations have been propagated through the literature until today. In an attempt to circumvent this problem we have developed a 'deterministic' algorithm for OMIM allele mutation mapping; see below.

The integration of dbSNP polymorphisms has been straight forward, because they are linked to a specific gene sequence within Genbank using the dbSNP identifiers ("rs" and "ss" numbers). Surprisingly only a very small number, 1.87%, of OMIM alleles have a dbSNP entry (see Table 3). We speculate that there are two reasons for this. First, most of the alleles in OMIM are Mendelian-mutations and have a very low minor-allele frequency. Secondly, SNPs have only recently been discovered during the human genome project and the SNP consortium efforts and clinical studies showing clinical correlations are still under way and they therefore have no allele entry within OMIM.

A preliminary study encouraged by the surprising low overlap between OMIM alleles and dbSNP entries performed using HGMD showed that OMIM alleles are represented in HGMD. We could find approximately 40% of the OMIM alleles from our 1,732 disease genes annotated in HGMD. This is a most promising finding and allows us to conclude that a lot of information can be gained by using the annotations from HGMD to link OMIM with the human genome assembly.

(c) Prototype Database Infrastructure

A prototype database infrastructure was built. Existing public domain database schemas were adapted to fulfill specific variation related needs. Furthermore, software was developed to load and update the specific genome and clinical databases. All annotation pipeline software as well as the visualization annotation station are driven by this database system. The detail of the prototype database system is as follows.

The database uses a loosely-coupled modular architecture (FIG. 2). Within each module, tables are tightly-coupled by means of relational foreign keys. Between modules, tables are implicitly linked by means of dbxrefs (database accessions) and gene symbols.

This modular architecture facilitates better software engineering and database management. Modules can be swapped in and out easily. Loading large data bulks or data management can be carried out on any module independent of the others. For example, if NCBI releases a new human genome assembly build, or a new dbSNP build, we can bulkload this without perturbing our marker data.

We used the Postgresql version 7.3 relational database management system (RDBMS). Postgresql has the advantage of being open source, as well as extremely robust, with a large community of users and developers who are eager to provide support for free. It is much simpler to manage and administer than commercial RDBMSs such as Oracle, and has many advantages over the other open source RDBMS like MySQL. We believe MySQL is not suited to a production environment because of its lack of full SQL92 support, such as views, sub-selects and foreign key integrity.

We have taken care not to incorporate any Postgresql specific functionality into the design, which means that a port to a commercial RDBMS such as Oracle should in the future be a relatively uncomplicated task.

(d) BioSQL Module

BioSQL (obda.open-bio.org) is a third party open source database schema and a PERL API (Application Programmer Interface). It is a generic database of sequences and sequence features. It is ideal for representing sequence data such as that from GenBank, the EMBL sequence database, SwissProt and RefSeq. We used it to store the NCBI Human Genome and NCBI human RefSeq. Data, loaded from NCBI flat file format using a PERL script that comes with the BioSQL distribution.

Figure 3:
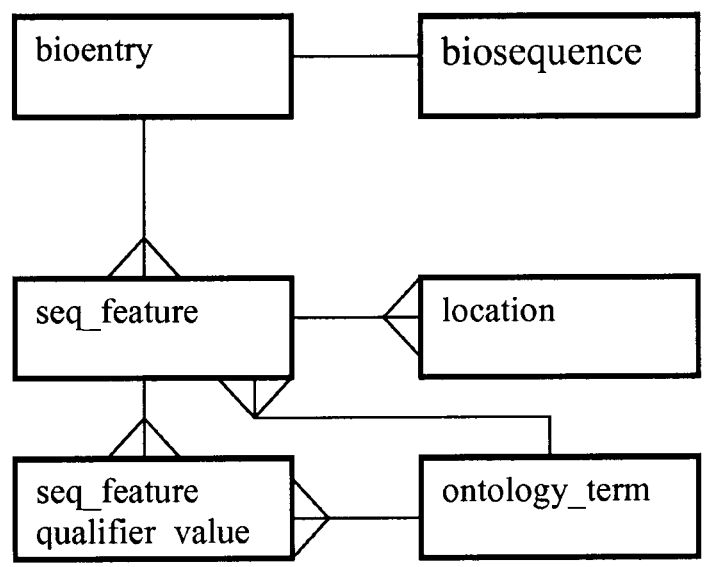
FIG. 3 represents BIOSQL schematic of the invention.

The BioSQL data model is based around the concept of 'bioentries' and 'seq_features'. This is equivalent to a Genbank/RefSeq record and feature table entry, respectively. One of these records typically contains features of type gene, mRNA, CDS and variation. The intersection between these locations tells us where the markers such as SNPs are with respect to exons, introns, untranslated regions (UTRs) and up/downstream regions. This data model is also suitable for housing the locations of the HGMD and OMIM variations mapped onto genomic coordinates. The most relevant part of the BioSQL schema can be seen in FIG. 3.

Figure 4:
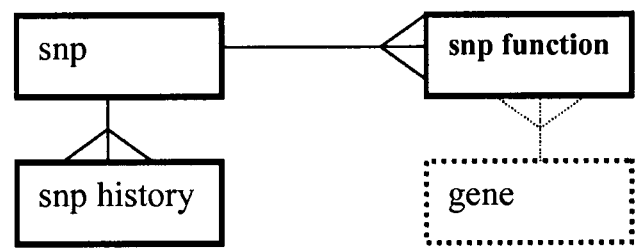
FIG. 4 represents a schematic overview of the SNP table of the invention.

The snp table (FIG. 4) stores single base pair and other variation features. Any none marker can have multiple effects, at the genomic, transcriptional and protein levels—this is what the snp_function table is for. It allows us to easily query for markers that affect a particular genomic area (exon, intron, UTR, protein, intergenic) or for protein-affecting markers what is the amino acid modification. Each of these effects is with respect to a particular gene; we have a weak (a non-foreign key that is not enforced) link to the gene table (in the DiseaseGene module, see below) via the official gene symbol.

(e) DiseaseGene Module

Figure 5:
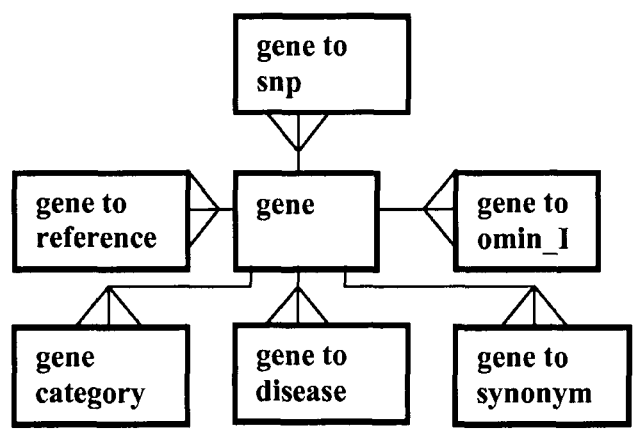
FIG. 5 represents a schematic overview of the DiseaseGene module of the invention

The DiseaseGene module (FIG. 5) is primarily for storing literature based curation of genes implicated in diseases, and associated information such as likely markers. Note that the gene_to_snp table is primarily for storing information on the literature curator's notes on possible markers, and is only weakly linked (implied via locational correspondence) with the snp table in the so-named OMICIASNP module. The gene table uses the official gene symbol; alternate symbols are stored in the gene synonym table. Each gene can have multiple disease categories, associated diseases or OMIM IDs.

Phenotype Module

The characteristics of the Web based graphical user interface (GUI) that support the manual mutation curation and map ping of phenotype information to the current genome assembly, are of a client/server design, with a graphical representation of a gene sequence with the associated mutation data through a Web browser, delivered through an integrated database. Using a web browser, the user interface can be accessed internally and secured externally for annotation and reviewing. From a user's perspective, the diverse analytic tools and algorithms, described below, appear as a single unified application. Users are able to edit the data and add annotations to the gene sequence throughout the process.

(g) OMIM-R

Figure 6:
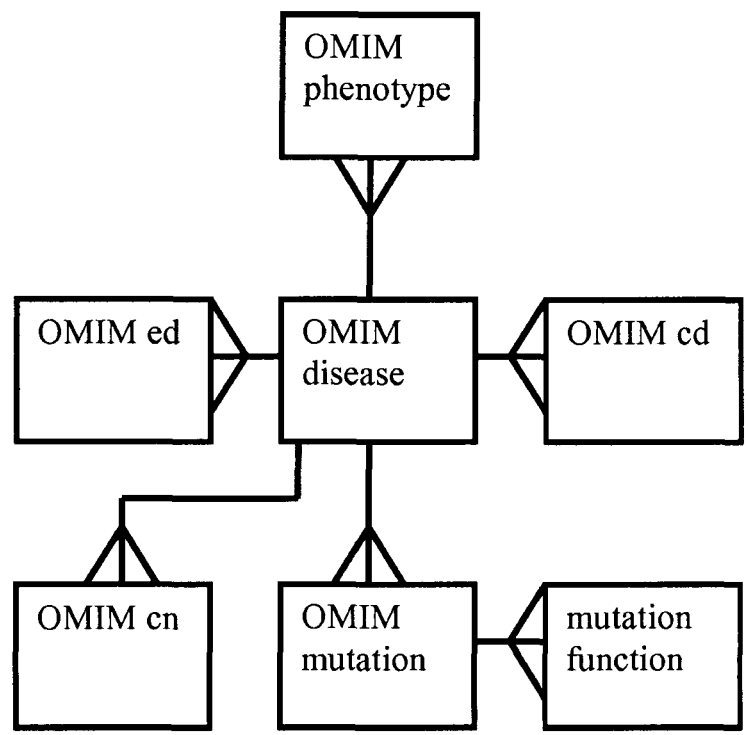
FIG. 6 represents a schematic overview of the OMIM-R module of the invention.

The OMIM-R module (FIG. 6) is a normalized relational model for housing data imported from OMIM. This module is focused around the OMIM disease table, which has an OMIM identifier as a primary key; this also serves as a weak key for integration with other modules in the OMICIADB schema. The cryptically named columns are named after multi-valued OMIM fields of the same name. Each disease can have multiple phenotypes attached. Each disease can also have multiple known mutations, and each of these can have multiple amino acid modifications.

(h) DbSNP-xml Module

This is a fairly simple module, as we opted to store each dbSNP entry as a single denormalised XML 'blob', accessed by a dbSNP identifier. This module is a single table, with a column for the dbSNP identifier, and the XML stored as a text field.

(i) Dataflow and Software Architecture for Database Loading

OMIM records are parsed into XML and then loaded into the OMIM-R module; any mutational information from the OMIM allele entries is mapped from protein coordinate space onto genomic coordinates from Genbank, and the resulting features are stored in the BioSQL module. The NCBI human genome build and RefSeq database are loaded into the BioSQL module. dbSNP is loaded into the dbSNP-xml module. Any disease gene information from the literature curation process is parsed into XML and then stored in the DiseaseGene module.

After any of these steps, which can be carried out independently, all genes in the DiseaseGene module are iterated through. For every gene we look for the corresponding gene annotation in BioSQL and find nearby marker features. We instantiate marker entries for all of these markers within a gene in the so-named OMICIASNP module. We also create a so-named OMICIAGeneSummary XML file, which integrates information from all modules into one XML document. The Annotation Station web interface code accesses this cached data for building the web displays. This is achieved through two Application Programming Interfaces (APIs)—the open source BioSQL PERL API and a PERL API. A proprietary PERL API developed by Omicia (so-named "OMICIA API") provides a unified access layer for all so-named OMICIADB modules and a simplified layer on top of the BioSQL API. However, the skilled artisan is able to construct his or her own API.

(j) Deterministic Algorithm for OMIM Allele Mutation Mapping

Many OMIM alleles could not be mapped directly, usually because some of the literature references were based on outdated versions of the reference sequence, or actually predated the availability of any reference sequence. When less than 50% of OMIM alleles for a gene could not be mapped, a simple codon position shift/deterministic algorithm was applied to get a higher percentage of mapped OMIM alleles. The algorithm is as follows: For a given gene, all OMIM allele codon positions are ordered and stored in a hash. Every neighboring OMIM protein allele is compared to the original protein sequence from Genbank. If any of these pairs match with the Genbank annotation, all other OMIM protein alleles are "shifted" according to the offset into the Genbank annotation as well. By using this deterministic algorithm, an additional 12.11% of OMIM alleles were mapped (see Table 4).

In order to evaluate software system, 97 genes were selected for annotation. The annotation consisted of reviewing the clinical associations for each marker within a gene, assessing it for significance, and then updating the database with a clinical reference and rationale for selection. Biologists supported by computer scientists performed this annotation process. The process was assessed and modified throughout the effort as bottlenecks were identified. More expeditious approaches were developed on the basis of overcoming these obstacles. Table 4 shows a summary of the selected 97 genes. OMIM had annotated a total of 529 alleles for these sequences. This corresponds in average to 5.45 allele annotations per gene. This is significantly higher than for our total set of disease genes, which had in average 3.25 alleles per gene (see Table 3). We believe this bias is due to the selection process, by which we mostly used well-known and therefore well-studied genes, for which many clinical studies have been performed over the years. Typical genes in our set include APOE, CFTR, APC, MTTR and all genes starting with the letter "R". Even with this result, about 30.60% of the OMIM alleles remain unmapped. More sophisticated algorithms can be developed to map a higher percentage of the remaining OMIM alleles.

We found that on average, the annotation of each gene took approximately 2 hours, but this time can be reduced through the use of text mining tools, and the development and refinement of a ranking scheme for the markers, as the integration of the clinical and pharmaceutical information, which is of great value to the individual client, is the most burdensome.

On the average 4.24 markers per gene were selected. The criteria for marker selection were based on the association significance of a marker with a disease. Markers were selected that were believed to be informative and useful for a typical individual. Based on this initial study, it is estimated that a set of approximately 7,344 (1,732 total disease genes× 4.24) informative disease markers is supported by the current clinical literature.

(k) A "High-Level" Genetic Disease Ontology

The genetic associations were placed into high-level categories, based upon a leading medical text, Harrison's Principles of Internal Medicine. The categories used were: Cancer; Cardiovascular; Endocrinology and metabolism; Gastrointestinal system; Hematology/blood disorders; Kidney and urinary tract; Immune system; Neurological and psychiatric disorders; Respiratory; and Others. This effort made clear that a uniform terminology does not exist within the medical literature. Therefore, the associations are preferably categorized using the MESH disease ontology (see Example 5 below).

TABLE 1

A typical disease gene research abstract for the RANTES gene (published in American Journal of Respiratory and Critical Care Medicine citation).
Original Article A Functional Polymorphism in the RANTES Gene Promoter Is Associated with the Development of Late-Onset Asthma
Nobuyuki Hizawa, Etsuro Yamaguchi, Satoshi Konno, Yoko Tanino, Eisei Jinushi and Masaharu Nishimura
First Department of Medicine, Hokkaido University School of Medicine, Sapporo, Japan
Correspondence: Correspondence and requests for reprints should be addressed to Nobuyuki Hizawa, First Department of Medicine, Hokkaido University School of Medicine, Kita-Ku, N-15 N-7, Sapporo, Japan 060-8638. E-mail: nhizawa@med.hokudai.ac.jp
The CC chemokine regulated upon activation, normal T-cell expressed and secreted (RANTES) attracts eosinophils, basophils, and T cells during inflammation and immune response, indicating a possible role for this chemokine in asthma. Both the -403A and -28G alleles of the RANTES promoter region exhibit significantly enhanced promoter activity in reporter constructs in vitro. We therefore investigated the genetic influence of these alleles on the development of asthma using case-control analysis in a Japanese population (298 patients with asthma and 311 control subjects). Given the evidence for heterogeneity of asthma according to age at onset, we divided patients with asthma into three subgroups: 117 late-onset patients with asthma (onset at more than 40 years of age), 83 middle-onset patients with asthma (onset at 20 to 40 years of age), and 98 early-onset patients with asthma (onset at less than 20 years of age). The -28G allele was significantly associated with late-onset asthma (odds ratio = 2.033; 95% confidence interval, 1.379–2.998; corrected p < 0.0025) but was not associated with the other two asthma subgroups. The -403A allele was not associated with any of the asthma subgroups. Further evidence of the importance of the -28G allele was a significant increase in the production of RANTES in vitro in individuals who carried this allele. Our findings suggest that, among Japanese, the -28G allele of the RANTES promoter region confers susceptibility to late-onset asthma.
Key Words: late-onset asthma · RANTES · single nucleotide polymorphism (SNP)

TABLE 2

OMIM entry 18701 for the RANTES gene.
*187011

CHEMOKINE, CC MOTIF, LIGAND 5; CCL5

Alternative titles; symbols
SMALL INDUCIBLE CYTOKINE A5, FORMERLY; SCYA5, FORMERLY
REGULATED UPON ACTIVATION, NORMALLY T-EXPRESSED, AND PRESUMABLY SECRETED; RANTES TABLE 2-continued OMIM entry 18701 for the RANTES gene.
*187011

T CELL-SPECIFIC RANTES
T CELL-SPECIFIC PROTEIN p228; TCP228
Gene map locus 17q11.2–q12
CLONING Using a human cDNA library that was enriched by subtractive hybridization for sequences
expressed by T lymphocytes but not B lymphocytes, Schall et al. (1988) isolated a gene
(D17S136E), which they designated RANTES, that encodes a novel T cell-specific molecule.
(RANTES is an acronym for 'Regulated upon Activation, Normally T-Expressed, and presumably
Secreted.') The gene product was predicted to be a 10-kD protein which, after cleavage of the
signal peptide, could be expected to be approximately 8 kD. Of the 68 residues, 4 are cysteines,
and there are no sites for N-linked glycosylation. Significant homology (30 to 70%) was found
between the RANTES sequence and several other T-cell genes, suggesting that they constitute
a family of small, secreted T-cell molecules.
Schall et al. (1988) found that RANTES, also designated p228 (TCP228) was expressed in 10
functional T-cell lines, but not in 8 hematopoietic tumor lines or in 6 T-cell tumor lines. Its
expression was increased more than 10-fold in peripheral blood lymphocytes 3 to 5 days
following mitogenic or antigenic stimulation.
GENE FUNCTION CD8-positive T lymphocytes are involved in the control of human immunodeficiency virus
(HIV) infection in vivo. Cocchi et al. (1995) demonstrated that the chemokines RANTES, MIP-1-
alpha (182283), and MIP-1-beta (182284) are the major HIV-suppressive factors produced by
CD8-positive T cells. HIV-suppressive factor activity produced by either immortalized or
primary CD8-positive T cells was completely blocked by a combination of neutralizing
antibodies against these 3 cytokines. On the other hand, recombinant forms of the 3 human
cytokines induced a dose-dependent inhibition of different strains of HIV-1, HIV-2, and simian
immunodeficiency virus (SIV). Cocchi et al. (1995) speculated that chemokine-mediated control
of HIV may occur either directly, through their inherent anti-lentiretroviral activity, or indirectly,
through their ability to chemoattract T cells and monocytes to the proximity of the infection foci.
However, this latter mechanism may also have the opposite effect of providing new, uninfected
targets for HIV infection. The authors noted that the findings may be relevant for the prevention
and therapy of AIDS.
Arenzana-Seisdedos et al. (1996) investigated a derivative of RANTES as a possible therapeutic
agent for inhibition of HIV infection. The derivative, called RANTES(9–68), lacks the first 8-N-
terminal amino acids and has no chemotactic or leukocyte-activating properties. RANTES(9–68)
was a potent receptor antagonist and inhibited infection of macrophage-tropic HIV. The anti-HIV
activity was somewhat lower than that of RANTES itself, which correlated with its lower affinity
for CC chemokine receptors. Arenzana-Seisdedos et al. (1996) found that the anti-HIV activity of
RANTES and RANTES(9–68) showed some variability depending on the donor cells. The authors
concluded that structural modification of a chemokine can yield variants lacking activation
properties but retaining both high-affinity for chemokine receptors and the ability to block HIV
infection.
Pritts et al. (2002) investigated the effect of PPAR-gamma ligands upon transcription and
translation of RANTES in human endometrial stromal cells. Three putative PPAR response
elements (PPREs) were found in the human RANTES promoter. In cells transfected both with
RANTES promoter vectors containing 958 bp and 3 PPREs, the addition of 2 PPAR-gamma
ligands inhibited promoter activity by 60% (P less than 0.01) and 48% (P less than 0.02),
respectively. Truncation of the gene promoter to delete all putative PPREs abrogated the ligand-
induced inhibition. Stromal cells showed a 40% decrease in RANTES protein secretion when
treated with a PPAR-gamma ligand (P less than 0.01). The authors concluded that use of PPAR-
gamma ligands to reduce chemokine production and inflammation may be a productive strategy
for future therapy of endometrial disorders, such as endometriosis.
MAPPING By analysis of somatic cell hybrids and by in situ hybridization using the cDNA probe, Donion et
al. (1990) assigned the RANTES locus to 17q11.2–q12. A secondary hybridization peak was
noted in the region 5q31–q34, which may represent the location of other members of the gene
family. The region on chromosome 5 overlaps with the location of an extended linked cluster of
growth factor and receptor genes, some of which may be coregulated with members of the
RANTES gene family.
MOLECULAR GENETICS RANTES is one of the natural ligands for the chemokine receptor CCR5 (CMKBR5; 601373) and
potently suppresses in vitro replication of the R5 strains of HIV-1, which use CCR5 as a
coreceptor. Previous studies showing that peripheral blood mononuclear cells or CD4+
lymphocytes obtained from different individuals have wide variations in their ability to secrete
RANTES prompted Liu et al. (1999) to analyze the upstream noncoding region of the RANTES
gene, which contains cis-acting elements involved in RANTES promoter activity, in 272 HIV-1-
infected and 193 non-HIV-1-infected individuals in Japan. They found 2 polymorphic positions,

TABLE 2-continued

OMIM entry 18701 for the RANTES gene.
*187011

1 of which was associated with reduced CD4+ lymphocyte depletion rates during untreated periods in HIV-1-infected individuals. This -28G mutation of the RANTES gene (187011.0001) occurred at an allele frequency of approximately 17% in the non-HIV-1-infected Japanese population and exerted no influence on the incidence of HIV-1 infection. Functional analyses of RANTES promoter activity indicated that the -28G mutation increases transcription of the RANTES gene. Taken together, these data suggested that the -28G mutation increases RANTES expression in HIV-1-infected individuals and thus delays the progression of the HIV-1 disease.
ALLELIC VARIANTS
(selected examples)

.0001 HUMAN IMMUNODEFICIENCY VIRUS TYPE 1, DELAYED DISEASE PROGRESSION WITH INFECTION BY [SCYA5, -28C-G]
In a large Japanese cohort of HIV-1-infected and non-HIV-1-infected individuals, Liu et al. (1999) identified a C-to-G transversion at position -28 in the promoter of the SCYA5 gene, also referred to as the RANTES gene. The -28G allele had a frequency of approximately 17% in the Japanese population and appeared to have no influence on the incidence of HIV-1 infection. However, functional analyses indicated that the -28G mutation increased transcription of the RANTES gene. Liu et al. (1999) suggested that the -28G mutation increases RANTES expression in HIV-1-infected individuals and thus delays the progression of the HIV-1 disease. They showed that the -28G mutation is associated with reduced rates of depletion of CD4+ lymphocytes in HIV-1-infected individuals, thus confirming that this polymorphism delays HIV-1 disease progression.
.0002 HUMAN IMMUNODEFICIENCY VIRUS TYPE 1, RAPID DISEASE PROGRESSION WITH INFECTION BY [SCYA5, 168923, T/C]. Among 7 SNPs within the RANTES gene investigated by An et al. (2002), one was the intronic RANTES regulatory element, In1.1T/C (168923T/C). They found that In1.1C-bearing genotypes accounted for 37% of the attributable risk for rapid progression to AIDS among African Americans. Because 36% of African Americans carry the In1.1C allele, it is likely that In1.1C may have a significant impact on the AIDS epidemic in sub-Saharan Africa.

REFERENCES
1. An, P.; Nelson, G. W.; Wang, L.; Donfield, S.; Goedert, J. J.; Phair, J.; Vlahov, D.; Buchbinder, S.; Farrar, W. L.; Modi, W.; O'Brien, S. J.; Winkler, C. A.: Modulating influence on HIV/AIDS by interacting RANTES gene variants. Proc. Nat. Acad. Sci. 99: 1002–1007, 2002. PubMed ID: 11792860
2. Arenzana-Seisdedos, F.; Virelizier, J.-L.; Rousset, D.; Clark-Lewis, I.; Loetscher, P.; Moser, B.; Baggiolini, M.: HIV blocked by chemokine antagonist. (Letter) Nature 383: 400 only, 1996. PubMed ID: 8837769
3. Bakhiet, M.; Tjernlund, A.; Mousa, A.; Gad, A.; Stromblad, S.; Kuziel, W. A.; Seiger, A.; Andersson, J.: RANTES promotes growth and survival of human first-trimester forebrain astrocytes. Nature Cell Biol. 3: 150–157, 2001.

TABLE 3

Statistical summary on the initial OMIM mapping efforts.

| Disease genes | | Percentage |
|---|---|---|
| Total "disease genes" | 1,732 | |
| Total "disease genes" mapped to build 30 | 1,614 | 93.19% |
| Non-uniquely mapped "disease genes" | 118 | 6.81% |
| Total OMIM alleles: | 5,624 | |
| OMIM alleles per gene: | 3.25 | |
| OMIM alleles mapped to build30 | 3,222 | 57.29% |
| OMIM alleles mapped to build30 using deterministic algorithm | 681 | 12.11% |
| Total OMIM alleles mapped: | 3,903 | 69.40% |
| OMIM alleles that are in dbSNP (incl. deterministic shift algorithm) | 105 | 1.87% |
| OMIM alleles that are in HGMD (incl. deterministic shift algorithm) | 2,276 | 40.47% |
| Total OMIM alleles either in dbSNP or HGMD | 2,381 | 42.34% |

TABLE 4

Annotated test set of 97 disease genes.

| Annotated Genes | | |
|---|---|---|
| Total # of genes: | 97 | 5.60% |
| Total OMIM alleles: | 529 | |
| OMIM alleles per gene: | 5.45 | |
| Total OMIM alleles either in dbSNP or HGMD | 432 | 81.66% |
| Total markers picked for annotated genes | 411 | |
| Markers picked per gene | 4.24 | |

Example 5

Ontologies for Marker Selection

In one embodiment of selecting one or more of the markers to be included in a preselected set of markers, in accordance with the present invention, an example of applicable techniques that can be applied follows. Briefly, 'porting' the MESH ontology to GO format facilitates the use of various software applications that have been developed for manual curation, editing and maintenance of the Gene Ontology (GO), allowing the rapid addition of human gene and disease information to MESH, and where necessary, allowing the alteration of the MESH ontology itself so as to render it a more suitable container for this information. A further integration of the GO terminology and refinement of the disease ontology for genetic disorders can facilitate the preselection of the set of markers.

We outline a methodology for doing so below, and also propose a text-mining approach (Yandell M D, Majoros W H,

*Genomics and natural language processing*, Nat Rev Genet 3: 601-10 [2002]) that makes use of the HGMD database to jump-start the entire effort by rapidly assigning the 1,037 human disease causing genes contained in HGMD to MESH via an automatic procedure. Preliminary studies indicate that assigning the human disease genes to MESH can bring many, as yet unappreciated relationships, between sequence homology and disease to light. FIG. 7 illustrates that in several cases genes involved in hand deformities are also involved in foot deformities, and that in some cases these genes are homologous to one another, e.g., PAX3, HOXA13, and MSX1 (all are homeodomain proteins); whereas FOXC2 and FOXE1 are paralogous genes of the Fork head class. In other cases, genes involved in related diseases are involved in the interacting signaling pathways and developmental processes, e.g., FGFR2 and GDF5 (for reviews see, Blundell T L et al., *Protein-protein interactions in receptor activation and intracellular signalling*, Biol Chem 381: 955-9 [2000]; Buxton P et al., *Growth/differentiation factor-5 (GDF-5) and skeletal development*, J Bone Joint Surg Am 83-A: S23-30 [2001]; Thiery J P, *Role of growth factor signaling in epithelial cell plasticity during development and in carcinogenesis*, Bull Acad Natl Med 185: 1279-92 [2001]). By systemically assigning all known human disease genes to MESH, previously unnoticed relationships between disease-causing genes. In many cases, genes homologous to a known disease gene—but not yet implicated in that disease—may prove to be involved in causing those same diseases. Tying genes to MESH provides an important resource allowing hypothesis generation for human disease research. Statistically significant associations between SNPs, haplotypes, and complex diseases can be significantly simplified by first assigning genes to MeSH.

In accordance with the invention, the assignment of genes to MESH provides a logical starting point by which to choose sets of genetic markers already implicated in a similar clinical phenotype, thereby revealing significant correlations between these gene marker sets and (related) disease phenotypes using SNP and haplotype data—and thereby, circumventing much of the statistical noise associated with large scale studies that attempt to identify groups of genes (without prior knowledge) using polymorphism data for all or a randomly chosen subset of genes. Placing genes in MESH also provides a means by which to cross-validate more traditional approaches to SNP and haplotype analysis.

The core database system consists of four major database components:

1. Disease marker database including genomic sequence and variation database
2. Individualized genome-profile mutation database
3. Clinical disease information database
4. Genetic profile report database The disease marker database has very many unstructured data points from genome sequence strings to disease ontologies such as MESH (Schulman J-L, *What's New for* 2001 *MeSH*, NLM Tech Bull. 317 [2001]). While loading these databases from public data repositories, various data consistency checks need to be implemented due to the unreliable and error-prone data stored in these databases. Further attention has to be paid to the fact that there is much redundancy in gene databases, which is mostly due to the unstructured gene nomenclature, only recently subject to efforts at unification.

For individualized genome-profiles there is physically separate storage of genetic data and the individual's geographical data due to extremely important privacy concerns. The genetic profile report database is a virtual joint over many entries from all the databases above. Nevertheless, any updates made by hand-editors such as genetic counselors should propagate back to the origin of the information storage. This versioning system is important to reduce redundant hand-editing.

The relationship between genes including their DNA sequences, mRNA sequences and protein sequences, and clinical disease phenotypes is annotated by automatic text mining algorithms to search and pre-filter literature database such as MEDLINE, employing a computer interface for disease marker phenotype annotation using disease ontology and clinical study abstracts (see, e.g., Example 4 above).

Example 6

Sample of Organizational Matrix for Communicating the Genetic Information to the Individual Existing disease ontologies such as MESH (Schulman, J-L, *What's New for* 2001 *MeSH*, NLM Tech Bull. 317 [2001]) are very technical and therefore not generally suited for the communication to individuals. The following example (Table 5) illustrates one embodiment of an organizational matrix for communicating genetic information to the individual in accordance with the invention. Specific focus is given to the most significant markers, most informative markers, markers specifically relevant for the gender, markers related to aging and markers that have a well-described pharmacogenomics application. Here, the individual is a hypothetical "Ms. Smith," to whom the terminology and structure of the report is explained in overview, and then detailed information is provided. Examples of other sections that are not shown in table 5 but which can be included are a glossary, a list of references for further information, a health risk appraisal, and an index. A "Rare Genetic Conditions or Carrier Report" at the end of the sample report lists, in alphabetical order, a panoply of genetic conditions for which testing was done, but is presented here in truncated form for the sake of brevity.

Table 5. <u>Example of organizational matrix</u>.

(a) <u>Report Structure</u>

Dear Ms. Smith,

Your report is structured to provide you with the most valuable information possible in regard to your genetic profile. Rather than overwhelming you with details about all of the sites that we assess, we provide you with summaries of this information in a structured way.

The major sections provide a number of views of your genetic profile.

(b) <u>Summmary</u>

The Summmary section provides a brief overview of the key genetic findings in the report. It lists the genes and sites that should be of most interest to you and points you to where more details can be found in the report. In addition, it provides an overview of key genes and sites that have special significance for women's health, men's health, aging, and drug interactions.

Table 5 cont. Example of organizational matrix.

(c) Health Category Section

To aid your understanding, your report is structured into health *categories*. These categories include standard medical divisions such as Cardiovascular, Respiratory, and Neurological and Psychological, along with categories such as Genetics and Therapeutics, Women's Health, and Aging that consolidate genes and sites into areas of particular importance to our clients. Genes, because they are associated with different conditions, may be reported in multiple categories.

At the beginning of each section, you will find a report of the major genes and sites tested in the area. An example of this report is shown below.

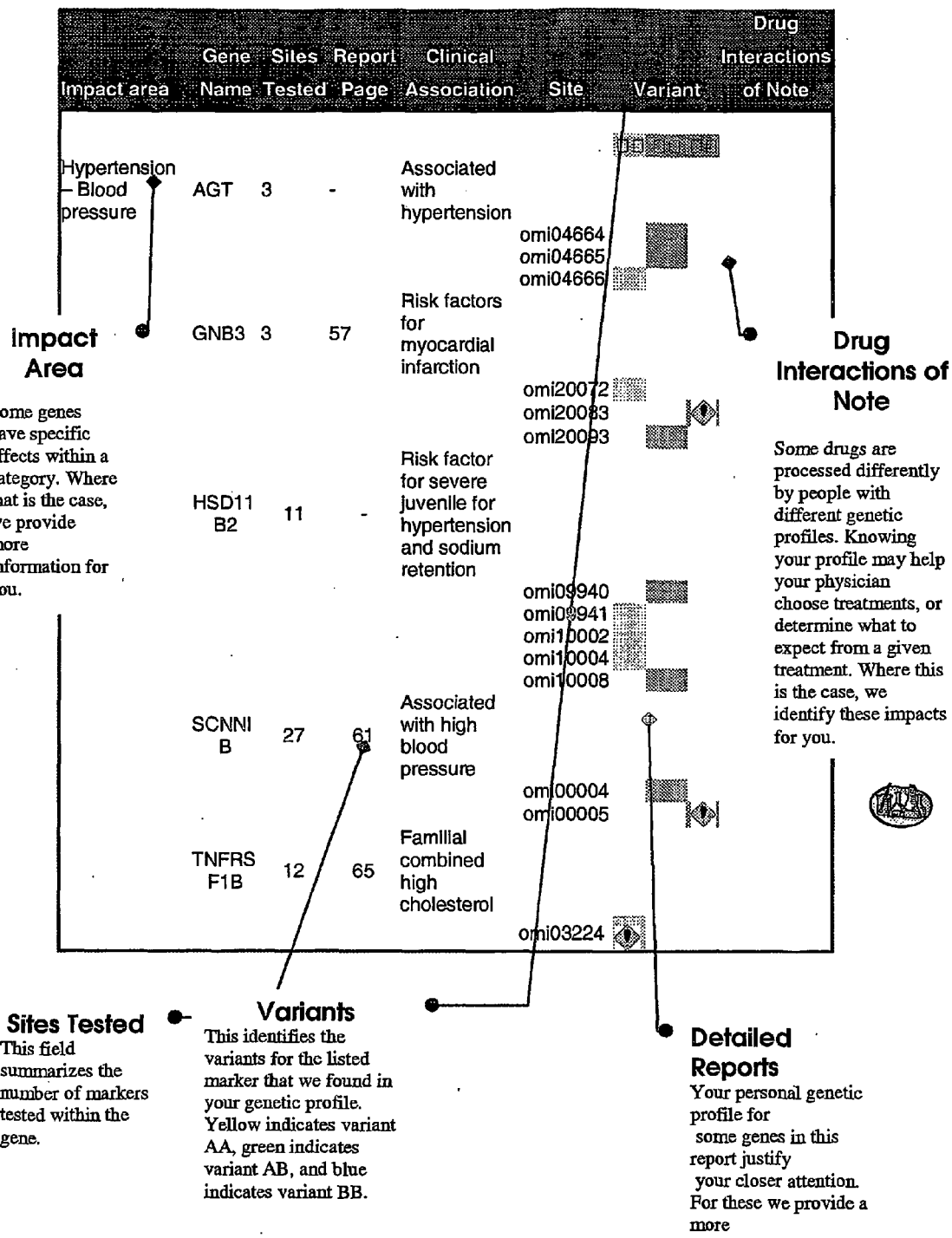

Table 5 cont. Example of organizational matrix.

Detailed Reports

The category summary reports point you to more detailed reports for those genes within each category that have the most relevant information for you. These gene reports provide structured information about the gene, its sites, and the most relevant material out of the clinical and genetic research literature. A form of this report is shown below.

Clinical Description

This provides a summary description of the clinical condition associated with the gene.

Tests Performed

These are the number of sites tested in this gene.

Actions

Your test results can indicate any number of appropriate actions. These actions fall into a number of categories. They include recommendations for changes in diet, exercise, potentially beneficial treatments, further testing or follow-up with your physician. In addition, the actions can include highlighting of risk factors of which you should be aware. These will always be taken from the relevant clinical literature and presented in context for you, allowing you to make the best decisions possible.

Items of Note

Many factors are important in the interpretation of the information provided. These include how well studied the association is, how relevant the populations that were studied are to someone of your ethnic background, the probability that an individual carrying a particular variant will develop the associated disease, and the frequency of the condition in the general population. Different genes and different conditions will have different sets of factors that contribute to the context for best understanding the implications of a particular test.

Test Results

The test results report on the variants that were found in your genetic profile.

Rare Disease Report

Each gene report is structured to provide the critical information that you need without overwhelming you with details. For each key gene tested, you will receive different categories of information that will help you understand the test results and what researchers and clinicians recommend for next steps Table 5 cont.
Finally, we test for hundreds of rare inherited conditions. To avoid overloading each category with conditions that will only be rarely found, we report on these in the Rare Disease Report. In this report, we simply provide the clinical condition name, the gene name and the number of sites tested. If a condition is in the rare condition report, Omicia did not find any significant sites for that condition in its testing.

Example of organizational matrix.

Report Summary for Ms. Smith

We tested your DNA at 10,326 distinct sites. We found that you are not at risk for 987 genetic conditions/diseases. These conditions/diseases are listed in the Rare Genetic Conditions section close to the end of this report. We found 186 sites that have been identified as having associations with medical conditions of note. The most significant of results, genes and sites are outlined below. Many of them recommend that you consult with your physician about the results.

- You have a lower risk of heart attack and ischemic stroke than the general population (for more details see pages 55, 64 and 59) but your profile indicates an increase in your cardiovascular disease risk. (for more details see pages 57 and 61).

- Because you are a *carrier* for the most prevalent, well-known Cystic Fibrosis site, you will not develop the disease. Your children will not develop the disease unless the other parent is a carrier also (for more details see page 67).

- You are at risk for asthma and allergies (for more details see page 69).

- Although you have a site that indicates you are at risk for hemochromatosis, donating blood is a common and effective prevention activity (for more details see page 70).

- Careful monitoring for breast cancer is recommended (for more details see page 75).

- Your genetic profile indicates that you are at low risk for the following:
    - Anemia
    - Bladder cancer
    - Colorectal cancer
    - Deafness
    - Dementia
    - Epilepsy
    - Huntington's disease
    - Leukemia
    - Lung cancer Table 5 cont
- Muscular dystrophy
- Parkinson's disease
- Sickle cell anemia Example of organizational matrix.

A summary of the significant genes and sites including those that have particular importance for women's health and those that are associated with conditions of aging are provided on the following pages.

Health Summary

| Impact area | Gene Name | Page Report | Sites Tested | Clinical Association | Sites of Note |
|---|---|---|---|---|---|
| Cardiovascular | GNB3 | 57 | 27 | Risk factors for heart attack | 3 |
|  | TNFRSF1B | 65 | 12 | Familial high cholesterol | 1 |
|  | THBS2 | 64 | 13 | Risk factor for coronary heart disease | 4 |
| Hematology and Blood disorders | HFE | 70 | 12 | Hemochromatosis | 1 |
| Immune System | PLA2G7 | 69 | 3 | Asthma and allergies | 1 |
| Respiratory | CFTR | 67 | 138 | Cystic Fibrosis | 1 |
| Endocrinology and Metabolism | PPARG | 81 | 11 | Obesity and Diabetes | 1 |

Women's Health

| Impact area | Gene Name | Page Report | Sites Tested | Clinical Association | Sites of Note |
|---|---|---|---|---|---|
| Cancer | TGFB1 | 75 | 13 | Breast cancer in elderly women | 4 |

| | | | | | |
|---|---|---|---|---|---|
| Cardiovascular | EPHX1 | 79 | 7 | Pre-eclampsia and pregnancy | 3 |
| Neurological and Psychiatric | COL9A2 | 88 | 7 | Intervertebral disk disease | 1 |

Table 5 cont. Example of organizational matrix.

Aging

| Impact area | Gene Name | Page Report | Sites Tested | Clinical Association | Sites of Note |
|---|---|---|---|---|---|
| Neurological and Psychiatric | COL9A3 | 89 | 27 | Intervertebral disk disease | 1 |
| | APOE | 84 | 7 | Alzheimer's Disease | 2 |
| | APP | 82 | 30 | Alzheimer's Disease | 0 |
| Other | ACE | 90 | 2 | Macular degeneration and blindness | 1 |
| | MTHFR | 59 | 17 | Osteoporosis | 1 |

You will find more detailed information about these sites in the sections for each health category. In addition, a number of genes had a particular effect on drugs or drug interactions. For your reference, these are outlined in the next table.

Drug Interactions of Note

The table below contains a summary of the genes with the most significant association with differential benefit and risk with different pharmaceuticals.

| Impact area | Gene Name | Page Report | Sites Tested | Clinical Association | Sites of Note |
|---|---|---|---|---|---|
| Cardiovascular | ADD1 | 54 | 21 | Coronary heart disease | 3 |
| | SCNN1B | 61 | 27 | Hypertension | 1 |
| Cancer | CYP3A4 | - | 16 | Prostate cancer and drug uptake | 3 |
| | ABCB1 | 78 | 11 | Multi-drug resistance | 1 |
| Other | DRD2 | 92 | 6 | Addiction to alcohol and nicotine | 1 |

Table 5 cont. Example of organizational matrix.

Cardiovascular Health

Your genetic profile affects your cardiovascular system in a variety of ways. Among those are: shaping your predisposition to high blood pressure, altering your risk of heart attack, and causing malformations of the heart. In addition, your profile can influence how you metabolize drugs that might be used to treat cardiovascular disease. Knowing your profile will arm you with the tools to manage, and potentially improve, your health.

Tests Performed

Explanations of the test results are stated in the detail reports following this list.

| Impact area | Gene Name | Sites Tested | Report Page | Clinical Association | Site | Variant | Drug Interactions of Note |
|---|---|---|---|---|---|---|---|
| Hypertension – Blood pressure | AGT | 3 | - | Associated with hypertension | | | |
| | | | | | omi04664 | | |
| | | | | | omi04665 | | |
| | | | | | omi04666 | | |
| | GNB3 | 3 | 58 | Risk factors for myocardial infarction | | | |
| | | | | | omi20072 | | |
| | | | | | omi20083 | | |
| | | | | | omi20093 | | |
| | HSD11B2 | 11 | - | Risk factor for severe juvenile for hypertension and sodium retention | | | |
| | | | | | omi09940 | | |
| | | | | | omi09941 | | |
| | | | | | omi10002 | | |
| | | | | | omi10004 | | |
| | | | | | omi10008 | | |
| | SCNNIB | 27 | 62 | Associated with high blood pressure | | | |
| | | | | | omi00004 | | |
| | | | | | omi00005 | | |
| | TNFRSF1B | 12 | 66 | Familial combined high cholesterol | | | |

| Impact area | Gene Name | Sites Tested | Report Page | Clinical Association | Site | Variant | Drug Interactions of Note |
|---|---|---|---|---|---|---|---|
| Coronary Heart Disease | TNFRSF 1B | 12 | 66 | Familial combined high cholesterol | | | |
| | | | | | omi03224 | ◆ | |
| | | | | | omi03225 | | |
| | | | | | omi03226 | | |
| | ADD1 | 21 | 54 | Left ventricular hypertrophy | | | |
| | | | | | omi02534 | | |
| | | | | | omi02535 | | |
| | | | | | omi02536 | | ◆ |
| | ADRB2 | 4 | - | Risk factor for congestive heart failure | | | |
| | | | | | omi11037 | | |
| | | | | | omi11039 | | |
| | | | | | omi11041 | | |
| | | | | | omi11029 | | |
| | | | | | omi11031 | | |
| | ADRBK1 | 1 | - | Associated with heart failure | | | |
| | | | | | omi12084 | | |
| | CD44 | 2 | - | Involved in atherosclerosis and risk factor for coronary syndromes and stroke | | | |
| | | | | | omi22057 | | |
| | ESR1 | 7 | 56 | Risk factor for coronary artery disease | | | |
| | | | | | omi00249 | | |
| | | | | | omi00250 | | |
| | | | | | omi00252 | | |
| | | | | | omi00255 | | ◆ |
| | | | | | omi00261 | | |
| | | | | | omi00262 | | |
| | | | | | omi22064 | | |
| | IL1B | 23 | - | Risk factor for myocardial ischemic dysfunction | | | |
| | | | | | omi10031 | | |

| Impact area | Gene Name | Sites Tested | Report Page | Clinical Association | Site | Variant | Drug Interactions of Note |
|---|---|---|---|---|---|---|---|
| | | | | | omi10032 | | |
| | | | | | omi10034 | | |
| | | | | | omi10035 | | |
| | | | | | omi10046 | | |
| | | | | | omi10047 | | |
| | | | | | omi10058 | | |
| | IL18 | 4 | - | Risk factor for myocardial ischemic dysfunction | | | |
| | | | | | omi02002 | | |
| | | | | | omi02004 | | |
| | | | | | omi02005 | | |
| | | | | | omi02007 | | |
| | KCNE1 | 6 | - | Risk factor for cardiac repolarization | | | |
| | | | | | omi02222 | | |
| | | | | | omi02223 | | |
| | | | | | omi02226 | | |
| | PON2 | 2 | - | Risk factor for coronary heart disease | | | |
| | | | | | omi22136 | | |
| | | | | | omi22137 | | |
| | THBS1 | 13 | - | Risk factor for coronary heart disease | | | |
| | | | | | omi22036 | | |
| | | | | | omi22038 | | |
| | THBS2 | 7 | 64 | Protective effect against myocardial infarction | | | |
| | | | | | omi15031 | | |
| | | | | | omi15032 | | |
| | | | | | omi15034 | | ◆ |
| | | | | | omi15035 | | |
| | | | | | omi15036 | | |
| | | | | | omi15037 | | |
| | | | | | omi15038 | | |
| | THBS4 | 2 | - | Risk factor for coronary artery disease | | | |
| | | | | | omi22057 | | |
| | | | | | omi22061 | | |

| Impact area | Gene Name | Sites Tested | Report Page | Clinical Association | Site | Variant | Drug Interactions of Note |
|---|---|---|---|---|---|---|---|
| Stroke | MTHFR | 17 | 60 | Susceptibility to stroke | | | |
| | | | | | omi04421 | | |
| | | | | | omi04422 | | |
| | | | | | omi04423 | | |
| | | | | | omi04424 | ◆ | |
| | | | | | omi04425 | | |
| | | | | | omi04426 | | |
| | | | | | omi04427 | | |
| | | | | | omi04428 | | |
| | | | | | omi04429 | | |
| | | | | | omi04430 | | |
| | TFPI | 3 | - | Protective factor for venous thromboembolism | | | |
| | | | | | omi02534 | | |
| | | | | | omi02535 | | |
| | | | | | omi02536 | | |
| | TLR4 | 7 | - | Protect against heart attack and stroke. | | | |
| | | | | | omi02723 | | |
| | | | | | omi02724 | | |
| Other | FBN1 | 11 | - | Associated with Marfan Syndrome | | | |
| | | | | | omi00053 | | |
| | | | | | omi00054 | | |

Table 5 cont. Example of organizational matrix.

| Category | Gene Name |
|---|---|
| Cardiovascular | Coronary Heart Disease — ADD1 |
| Clinical Description | Items of Note |

The enlargement of the heart's left ventricle (lower left pumping chamber), known as ventricular hypertrophy, is a risk factor for cardiovascular disease.

The adducin gene, ADD1, on chromosome 1 is associated with cardiovascular disease and specifically with the enlargement of the left ventricle of the heart. Hypertrophy of the left ventricle is defined as a wall thickness greater than 1.5 cm with an increased heart weight.

✓ Your variant BB predisposes you to left ventricular hypertrophy, which is a risk factor for cardiovascular disease.

Test Results

We tested for results at 21 sites in this gene. Your profile is associated with a predisposition to develop cardiovascular disease and, more specifically, an enlargement of the left ventricle of the heart.

Technical and Reference Information

At site omi02536, you have variant BB. Clinical studies in September of 2002 were recruiting individuals for the Hypertension and Ambulatory Recording Venetia Study in Italy. In this study they could show that variant BB predisposes certain individuals for left ventricular hypertrophy, LVH, a condition which itself is associated with an increased risk of cardiovascular morbidity and mortality. Carriers of variant BB had a left ventricular mass index significantly higher compared with carriers of at least one variant A. These subjects also had significantly lower plasma renin activity (PRA). 40% of variant BB carriers had left ventricular hypertrophy.

Variant BB at site omi02536 of the adducin gene is independently associated with increased LV mass and low PRA, which is shown to increase cardiovascular morbidity and mortality risk.

At site omi02534 you have variant AA and at site omi02535, you have variant AB. While these sites have been shown to be associated with clinical conditions, your variants have none of these conditions.

According to the published research, these data suggest that genetic considerations may contribute importantly to risk stratification, and perhaps therapeutic interventions can be targeted at LVH and the renin-angiotensin system in patients with high blood pressure.

Actions

We recommend that you discuss this genetic condition and any appropriate actions with your physician. As part of the Active Health Management Service, We will keep you updated as new research is published concerning this site.

Table 5 cont. Example of organizational matrix.

| Category | | Gene Name |
|---|---|---|
| Cardiovascular | Coronary Artery Disease | ESR1 |
| | Clinical Description | Items of Note |

Coronary arteries are the blood vessels that supply your heart with blood. Coronary artery disease occurs when these arteries become clogged with plaque, a build up of cholesterol and calcium. This is called hardening of the arteries or atherosclerosis.

The estrogen receptor gene, ESR1, on chromosome 6 is associated with coronary artery disease for postmenopausal women.

✓ Coronary artery disease is the leading cause of disease and death in the United States in both men and women. 12 million Americans have coronary artery disease.
(Source: WebMD, 2002)

Test Results

We tested for results at 7 sites in this gene. Your profile at one site is associated with an increase in HDL cholesterol levels, which is the good cholesterol, in women that underwent hormone replacement therapy across racial and ethnic groups.

Technical and Reference Information

At this site, omi00255, you have variant BB. Clinical studies by Herrington et al. published in the New England Journal of Medicine in 2002 describing the impact of carrying one or two copies of variant B were conducted at the Departments of Internal Medicine, Pediatrics, and Public Health Sciences, and the Hypertension and Vascular Disease Center, Wake Forest University, Winston-Salem, NC, under the auspices of the Estrogen Replacement and Arteriosclerosis Trial. In these studies women that carry two copies of variant B and underwent hormone replacement therapy (HRT), were shown to have more than twice as high levels of high density-lipoprotein (HDL) cholesterol, (good cholesterol). High levels of HDL are thought to protect against heart disease. The pattern of increased response of HDL cholesterol in women with variant BB was preserved across racial and ethnic groups.

At site omi00248 you have variant AA, at site omi00250 you have variant AA, at site omi00251 you have variant AA, at site omi00261 you have variant AA, at site omi00262 you have variant AB and at site omi00264 you have variant AA. While all these sites have been shown to be associated with clinical conditions, your variants have none of these conditions.

Although the HDL cholesterol level increase for women with HRT was significant, to this date the study could not show that the progression of coronary heart disease was not significantly different between the women on HRT with 2 copies of variant BB at omi00255, and those on HRT with 1 copy or no copy of variant B. Nevertheless, increased levels of HDL cholesterol are shown in other clinical studies (Krauss 2002) in the *New England Journal of Medicine* to have a protective effect as regards to cardiovascular disease.

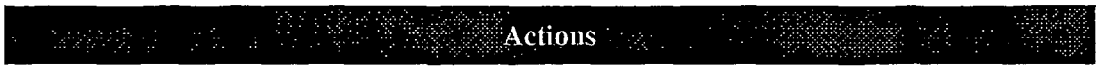

As part of any good health management program, LDL and HDL cholesterol levels should be monitored. Please discuss your cholesterol levels with your physician routinely. Your physician will decide whether you need dietary and lifestyle changes or medicine.

As part of the Active Health Management Service, We will keep you updated as new research is published concerning this site.

Table 5 cont. Example of organizational matrix.

| Category | Gene Name |
|---|---|
| Cardiovascular | High Blood Pressure/Hypertension |
| Clinical Description | Items of Note |

Blood pressure is the force of the flowing blood against the walls of the arteries. It is measured with two numbers, systolic and diastolic blood pressure. Systolic blood pressure measures the force of the blood flow when the heart is contracting. Diastolic blood pressure measures the force of the blood flow when the heart is relaxing.

High blood pressure, also known as hypertension, makes your heart and arteries work harder and can result in negative health effects.

The guanine nucleotide-binding protein gene, GNB3, on chromosome 12 is associated with high blood pressure.

✓ About one in every four American adults has high blood pressure.

(Source: WebMD, 2002)

Test Results

We tested for results at 3 sites in this gene. Your profile is associated with a predisposition for developing increased systolic and diastolic blood pressure.

Technical and Reference Information

The analysis at 2 genetic sites found that, for these sites, you have no variants that are associated with significant clinical conditions. You have a variant of note at the third site.

At this site, omi20083, you have variant BB. A clinical study describing the impact of carrying one or two copies of variant B was conducted. In these studies, variant B, when carried in two copies, is shown to have a significant association with essential hypertension.

This study by Topol et al. was conducted by examining 427 people with normal blood pressure and 426 with high blood pressure. They conclude that carriers of variant BB may identify patients who are more responsive to diuretic therapy.

Clinical studies (Topol *et al.*, 2002) in the journal *Hypertension*, indicate that variant BB carriers at site omi20083 may be more responsive to diuretic therapy. We recommend that you discuss with your physician whether this treatment would be appropriate for you, given this information.

Actions

Everyone should monitor his or her blood pressure carefully. Please routinely check your numbers and discuss the results with your physician. The American Heart Association suggests that you work with your doctor to determine the best plan for you. It may include a low-fat diet, a low-salt diet, and changes in your living habits such as losing weight and getting more exercise, quitting smoking, and reducing your alcohol intake may be recommended. Many medicines also can help reduce and control high blood pressure. Your doctor will decide whether you need medicine in addition to dietary and lifestyle changes.

As part of the Active Health Management Service, We will keep you updated as new research is published as it relates to your profile.

Table 5 cont. Example of organizational matrix.

| Category | Gene Name |
|---|---|
| Cardiovascular | MTH |
| Clinical Description | Items of Note |

An ischemic stroke occurs when a blood clot stops blood flow to one of the brain's arteries.

The Methylene Enzyme gene, MTHFR, on chromosome 1 is associated with susceptibility to ischemic stroke. This gene is also associated with osteoporosis (see Category "Other").

✓ More than 150,000 people die from a stroke each year. That makes stroke the third leading cause of death behind cancer and heart disease.

Test Results

We tested for results at 17 sites in this gene. Your profile suggests conflicting results. The profile may be protective against stroke or may suggest a higher susceptibility to stroke and cardiovascular health issues.

(Source: The American Academy of Neurology's 54th Annual Meeting in Denver, April 13-20, 2002)

Technical and Reference Information

The analysis of 16 genetic sites found that, for these sites, you have no variants that are associated with significant clinical conditions. You have a variant of note for one site.

At this site, omi04424, you have variant AA. Clinical studies describing the impact of site omi04424 were conducted in Dutch, Japanese and most recently Chinese populations (Li et al., 2002). Schneider et al, 1998, in another clinical study, found the frequency for a copy of variant B to be elevated in cardiovascular patients in every population around the world They pointed out that the frequency of variant B was lowest in Africa (6.6%) compared with Europe and Asia.

Li et al. pointed out that variant BB "may have a protective effect against ischemic stroke", while carriers of variant AA "were 4.3 times more susceptible to ischemic stroke than the controls", and the individuals with variant AB "were 1.63 times more susceptible to ischemic stroke than the controls".

Actions

According to the American Stroke Association, high blood pressure increases the risk of stroke up to four-fold. Proper treatment can diminish that risk by 38 percent. Cigarette smoking nearly doubles stroke risk, but quitting can slash the risk in half within one year and decrease it to a level similar to non-smokers after five years. In addition to blood pressure management and quitting smoking, the AHA recommends these lifestyle suggestions for limiting stroke risk:

- a healthy diet with five servings of fruits and vegetables daily;
- avoid illicit drug use;
- weight reductions in overweight persons;
- a minimum of 30 minutes of moderate intensity activity daily;
- avoid secondhand tobacco smoke; and
- limit alcoholic drinks to no more two per day for men and one per day for women As part of the Active Health Management Service, We will keep you updated as new research is published as it applies to your profile for this site.

Table 5 cont. Example of organizational matrix.

| Categories | Gene Name |
|---|---|
| Cardiovascular | High Blood Pressure | SCN |

| Clinical Description | Items of Note |
|---|---|

Blood pressure is the force of the flowing blood against the walls of the arteries. It is measured with two numbers, systolic and diastolic blood pressure. Systolic blood pressure measures the force of the blood flow when the heart is contracting. Diastolic blood pressure measures the force of the blood flow when the heart is relaxing.

High blood pressure, also known as hypertension, makes your heart and arteries work harder and can result in negative health effects.

The sodium channel gene, SCNN1B on chromosome 16 is associated with high blood pressure and Liddle's Syndrome, which is associated with extremely high blood pressure.

✓ Your variant is found in 1% of individuals of European origin, and approximately 5% of individuals of African-American descent.

Test Results

We tested for results at 27 sites in this gene. One of those sites is associated with high blood pressure in people with particular ethnic backgrounds. For example, for those with your profile, high blood pressure occurs in approximately 1% of individuals of European origin and approximately 5% of individuals of African-American descent.

Technical and Reference Information

The analysis at 26 genetic sites found that, at these sites, you have no variants that are associated with significant clinical conditions. You have a variant of note for one site.

At this site, omi00005, you have variant BB. Clinical studies describing the impact of carrying one or two copies of variant B were conducted at St George's Hospital in London, England, and at the Institute of Pharmacology and Toxicology in Lausanne, Switzerland. In these studies, Variant B, when carried in two copies, contributes to the elevation of blood pressure in some ethnic lineages.

Variant BB is associated with high blood pressure and occurs in approximately 1% of individuals of European origin, and approximately 5% of individuals of African-American descent.

Actions

Everyone should monitor his or her blood pressure carefully. Please routinely check your numbers and discuss the results with your physician. The American Heart Association suggests that you work with your doctor to determine the best plan for you. It may include a low-fat diet, a low-salt diet, and changes in your living habits such as losing weight and getting more exercise, quitting smoking, and reducing your alcohol intake may be recommended. Many medicines also can help reduce and control high blood pressure. Your doctor will decide whether you need medicine in addition to dietary and lifestyle changes.

Clinical studies (Baker *et al.*, 2002) in the journal *Hypertension*, indicate that the drug Amiloride is effective in lowering blood pressure in individuals that have this genetic profile. We recommend that you discuss with your physician whether this treatment would be appropriate for you, given this information.

As part of the Active Health Management Service, We will keep you updated as new research is published as it relates to your profile.

Table 5 cont. Example of organizational matrix.

| Category | Gene Name |
|---|---|
| Cardiovascular | THB |
| Heart Attack | |
| Clinical Description | Items of Note |

A heart attack occurs when blood flow to the heart is blocked by a blood clot.

The thrombospondin gene, THBS2, on chromosome 6 is associated with heart attack, also known as myocardial infarction.

✓ 1.1 million Americans suffer a heart attack yearly. About 460,000 of those heart attacks are fatal.

Test Results

We tested for results at 7 sites in this gene. Your profile is associated with a decreased risk of heart attack.

(Source: National Heart, Lung, and Blood Institute of the National Institutes of Health, 2002)

Technical and Reference Information

The analysis at 6 genetic sites found that, for these sites, you have no variants that are associated with significant clinical conditions. You have a variant of note at one site.

At this site, omi25034, you have variant BB. A clinical study describing the impact of carrying one or two copies of variant B was conducted at 15 participating medical centers in the US. In these studies, variant B, when carried in two copies, is shown to have a protective effect (odds ratio of 0.31) against myocardial infarction (heart attack).

This study by Topol et al. was conducted including 398 families of various population origins. Myocardial infarction is one of the highest causes of death in the western world.

Actions

Your profile is found to protect against heart attack. For your information, the National Heart, Lung and Blood Institute, which is part of the National Institutes of Health, states that taking the following steps will reduce your risk of having a heart attack: Stop smoking, lower high blood pressure, reduce high blood cholesterol, aim for a healthy weight, be physicially active each day, and manage diabetes. Please consult your physician to discuss what these recommendations mean to you.

As part of the Active Health Management Service, We will keep you updated as new research is published concerning this site.

Table 5 cont. Example of organizational matrix.

| Category | Gene Name |
|---|---|
| Cardiovascular | T |
| High Blood Pressure | |
| Clinical Description | Items of Note |

Blood pressure is the force of the flowing blood against the walls of the arteries. It is measured with two numbers, systolic and diastolic blood pressure. Systolic blood pressure measures the force of the blood flow when the heart is contracting. Diastolic blood pressure measures the force of the blood flow when the heart is relaxing.

High blood pressure, also known as hypertension, makes your heart and arteries work harder and can result in negative health effects.

The tumor necrosis factor receptor gene, TNFRSF1B, on chromosome 1 is associated with high blood pressure (hypertension) and high cholesterol (hyperlipidemia).

✓ High blood pressure affects about 50 million, or one in four, American adults.

(Source: National Heart, Lung, and Blood Institute of the National Institutes of Health, 2002)

Test Results

We tested for results at 12 sites in this gene. Your profile at one site indicates no association with high blood pressure or high cholesterol.

Technical and Reference Information

The analysis at 11 genetic sites found that, for these sites, you have no variants that are associated with significant clinical conditions. You have a variant of note for one site.

At this site, omi03226, you have variant AA. A clinical study describing the impact of this site showed a significant association with essential hypertension for variant BB, but none for your variant AA. This study by Geurts et al. was conducted in the Netherlands and was based on 79 sibling pairs with 40 hypertension patients and 48 familial controls and published in the *Journal Human Molecular Genetics* in 2000.

Familial combined hyperlipidemia (high cholesterol) is the most common inherited lipidemia in man with a frequency of 1-2% in the general population. For one of the most significant sites you are carrying the healthy variant AA.

Actions

Your profile on this site is not associated with high blood pressure. For your information, the American Heart Association suggests that everyone should monitor his or her blood pressure carefully. Please routinely check your numbers and discuss the results with your physician. The American Heart Association also suggests that you work with your doctor to determine the best plan for you. It may include a low-fat diet, a low-salt diet, and changes in your living habits such as losing weight and getting more exercise, quitting smoking, and reducing your alcohol intake may be recommended. Many medicines also can help reduce and control high blood pressure. Your doctor will decide whether you need medicine in addition to dietary and lifestyle changes.

As part of the Active Health Management Service, We will keep you updated as new research is published concerning this site.

Table 5 cont. Example of organizational matrix.

Respiratory

| Category | Gene Name |
|---|---|
| Respiratory Health | Cystic Fibrosis — C |
| Clinical Description | Items of Note |

According to the National Institutes for Health (NIH), cystic fibrosis is a disease of the bodies mucus glands which primarily causes problems with the lungs and pancreas, resulting in malnutrition, poor growth, frequent respiratory infections, breathing difficulties, and eventually permanent lung damage. Lung disease is the usual cause of death in most patients.

The Cystic Fibrosis gene, CFTR, On chromosome 7 is associated with persistent bacterial infections of the airways. Cystic fibrosis is caused by variations at multiple site locations in the CFTR gene. Most of the cases of cystic fibrosis are caused by a small percentage of these variants.

✓ About one in 2,500 Caucasians is affected and 2-5% of Caucasians carry sites associated with cystic fibrosis.

✓ Cystic fibrosis is the most common cause of chronic lung disease in children and young adults, and the most common fatal hereditary disorder affecting Caucasians in the US.

Test Results

We tested for results at 138 sites in this gene. Your genetic profile is associated with a very low risk for developing cystic fibrosis, but you are a *carrier* for the cystic fibrosis variant.

Technical and Reference Information

Of the 138 sites tested, one site is of clinical significance.

Site omi09453 is associated with cystic fibrosis. Because you are a *carrier* for the most prevalent, well-known cystic fibrosis variant AB, you will not develop the disease. A *carrier* is an individual who may transmit a genetic condition but who normally does not show any evidence of the disease. Your children will not develop the disease unless the other parent is a *carrier* also.

Actions

Please discuss these results with your physician.

As part of the Active Health Management Service, We will keep you updated as new research is published concerning this site.

Table 5 cont. Example of organizational matrix.

Immune system

| Category | Gene Name |
|---|---|
| Immunological Health | Allergies and Asthma |

| Clinical Description | Items of Note |
|---|---|

An allergy is an overreaction of the immune system that results in a variety of mild, moderate, or severe symptoms.

Asthma is a disease that causes the lung's airways to narrow making breathing difficult.

The platelet activating factor gene, PLA2G7 on chromosome 16, is associated with asthma and allergies.

✓ 50 million Americans suffer from asthma or upper respiratory symptoms due to allergies.

Test Results

We tested 3 sites in this gene. One site indicates that you are at risk for allergies and asthma.

Technical and Reference Information

Of the three genetic sites tested, two were not associated with significant clinical conditions. You have a variant of note at the third site.

At this site, omi07345, you have variant AB. The study by Kruse et al. published in the *American Journal of Human Genetics* in 2000 found this variant to be highly associated with specific sensitization to allergies and with asthma. It seems to play a key role in both of these conditions in Caucasian populations.

Actions

You should consult with your physician concerning this information.

As part of the Active Health Management Service, We will keep you updated as new research is published concerning this site.

Table 5 cont. Example of organizational matrix.

Hematology/Blood disorders

| Category | Hemochromatosis | Gene Name |
|---|---|---|
| Blood Disorders | | |
| Clinical Description | | Items of Note |
| Hemochromatosis is a disorder in which iron accumulates in organs and body tissues. The results of hemochromatosis can include cirrhosis of the liver, diabetes, darkened skin (hypermelanotic pigmentation), and heart failure. Primary liver cell cancer and complications of cirrhosis are responsible for about one-third of deaths in affected individuals. | | ✓ The condition is estimated to afflict more than a million Americans, or about 1 in every 250 people, far fewer than suffer from an iron deficiency but still more than all those afflicted with cystic fibrosis, Huntington's disease, and muscular dystrophy combined. (Source: DrKoop.com, |
| Test Results | | |

We tested for results at 12 sites in this gene. One site indicates a strong association with hemochromatosis.

Technical and Reference Information

Of the twelve genetic sites tested, eleven were not associated with significant clinical conditions. You have a variant of note for one site.

At this site, omi77551, you have variant BB. This variant is strongly associated with hemochromatosis. Feder *et al.*, in a study published in *Nature Genetics*, in 1996 found this variant in 85% of the patients with this condition. In contrast, only 3.2% of controls carried this variant. The study included 178 patients and 310 controls.

The incidence of variant AB at omi77551 in the white population is approximately 10%. The expected incidence of variant BB is about 2 to 3 per 1,000.

Actions

You should consult with your physician to determine an appropriate course of action. Clinical studies have recommended that regular therapeutic removal of blood (blood donation) can help with the high iron levels associated with this condition. As part of the Active Health Management Service, We will keep you updated as new research is published concerning this site.

Table 5 cont. Example of organizational matrix.

Cancer

Tests Performed

Explanations of the test results are stated in the detail reports following this list.

| Impact area | Gene Name | Sites Tested | Report Page | Clinical Association | Site | Variant OO / O● / ●● | Drug Interactions of Note |
|---|---|---|---|---|---|---|---|
| Breast Cancer | BRCA1 | 72 | | Risk factors for breast cancer | | | |
| | | | | | omi020 72 | | |
| | | | | | omi020 83 | | |
| | | | | | omi020 93 | | |
| | BRCA2 | 143 | | Risk factors for breast cancer | | | |
| | | | | | omi040 76 | | |
| | | | | | omi040 77 | | |
| | | | | | omi040 78 | | |
| | | | | | omi040 89 | | |
| | | | | | omi040 92 | | ⇧ |
| | | | | | omi040 99 | | |
| | | | | | omi041 00 | | |
| | | | | | omi041 21 | | |
| | | | | | omi041 25 | | |
| | | | | | omi041 30 | | |
| | | | | | omi041 32 | | |
| | | | | | omi041 37 | | |
| | | | | | omi041 44 | | |
| | CYP1A1 | 12 | - | Risk factors for breast cancer | | | |

| Impact area | Gene Name | Sites Tested | Report Page | Clinical Association | Site | Variant | Drug Interactions of Note |
|---|---|---|---|---|---|---|---|
| | | | | | omi060 28 | | |
| | | | | | omi060 29 | | |
| | | | | | omi060 30 | | |
| | TGFB1 | 5 | 76 | Risk factors for breast cancer | | | |
| | | | | | omi150 22 | | |
| | | | | | omi150 23 | ◆ | |
| | | | | | omi150 25 | | |
| | XRCC2 | 27 | - | Risk factors for breast cancer | | | |
| | | | | | omi060 48 | | |
| | | | | | omi060 49 | | |
| | XRCC3 | 7 | - | Risk factors for breast cancer | | | |
| | | | | | omi190 59 | | |
| Lung cancer | CRMP1 | 3 | - | Risk factor for lung cancer | | | |
| | | | | | omi023 30 | | |
| Bladder | GSTP1 | 24 | - | Increased risk of bladder cancer | | | |
| | | | | | omi072 30 | | |
| | | | | | omi072 31 | | |
| | | | | | omi072 32 | | |
| Other | ABCB1 | 11 | 78 | Cancer drug resistance | | | |
| | | | | | omi033 44 | | ▼ |
| | | | | | omi033 45 | | |
| | | | | | omi033 47 | | |
| | | | | | omi033 48 | | |
| | | | | | omi033 49 | | |
| | | | | | omi033 50 | | |

| Impact area | Gene Name | Sites Tested | Report Page | Clinical Association | Site | Variant | Drug interactions of Note |
|---|---|---|---|---|---|---|---|
| | | | | | omi033 53 | | |
| | | | | | omi033 54 | | |
| | RNASEL | 2 | - | Risk factors for apoptosis related cancer progression | | | |
| | | | | | omi002 40 | | |
| | | | | | omi002 41 | | |
| | DMP1 | 2 | - | Risk predisposition for lymphoma cancer | | | |
| | | | | | omi112 23 | | |
| | | | | | omi112 24 | | |

Table 5 cont. Example of organizational matrix.

| Category | Gene Name |
|---|---|
| Cancer | Breast Cancer |
| | T |
| Clinical Description | Items of Note |

Breast cancer is the uncontrolled growth of cells in the breast.

The Transforming Growth Factor Beta 1 gene, TGFB1, on chromosome 19, has been shown to be associated with breast cancer in elderly women.

✓ General Population Risk of Getting Breast Cancer:

Test Results

We tested for results at 5 sites in this gene. Your profile at this gene is associated with lower risk of developing breast cancer.

- By age 25   1 in 19,608
- By age 35   1 in 622
- By age 45   1 in 93
- By age 55   1 in 33
- By age 65   1 in 17
- By age 75   1 in 11
- By age 85   1 in 8

(Source: National Cancer Institute)

Technical and Reference Information

Of the five genetic sites tested, four were not associated with significant clinical conditions. You have a variant of note for one site.

At this site, omi15023, you have variant AA. This variant has been extensively analyzed at the San Francisco Veteran Affairs Medical Center, at Epidemiology and Biostatistics, University of California, San Francisco, at the Graduate School of Public Health in Pittsburgh, and at Axys Pharmaceuticals Inc in La Jolla, in their Osteoporotic Fracture Study. This study, involving 3,075 women, found this variant to be associated with breast cancer in elderly white women 65 years or older, after allowing for adjustments made for estrogen usage, bone mineral density, and bone mass index, as well as age, age at menarche and age at menopause.

Ziv *et al.* showed in the *Journal of the American Medical Association* in 2001, that Variant A, when carried in two copies, confers in women a significantly lower risk of developing breast cancer than does carrying one or no copies. Women in these last two categories have a 2.5 to 3 fold higher risk of breast cancer compared with women, such as you, who carry two copies of the variant.

Actions

Your profile at this site indicates a low risk of developing breast cancer. Please discuss the results with your physician.

As part of the Active Health Management Service, We will keep you updated as new research is published concerning this site.

Table 5 cont. Example of organizational matrix.

| Category | Gene Name |
|---|---|
| Cancer | Multi-drug resistance A |
| Clinical Description | Items of Note |

The multi-drug resistance gene, ABCB1, on chromosome 7, has been shown to be associated with the rate at which the body absorbs medication including HIV medications and chemotherapeutic drugs.

✓ Because you are a carrier of variant BB at one of the site, you may respond better to oral chemotherapy.

Test Results

We tested for results at 11 sites in this gene. Because you are a carrier of variant BB at one of the site, you may respond better to oral chemotherapy.

Technical and Reference Information

Of the eleven genetic sites tested, ten were not associated with significant clinical conditions. You have a variant of note for one site.

At this site, omi03344, you have variant BB. In clinical studies reported by Dr. Howard L. McLeod of Washington University School of Medicine in St. Louis, Missouri, at the American Association for Cancer Research's annual meeting in 2001 this variant has been shown to be associated with lower P-glyco-protein (PGP) levels. PGP pumps certain cancer drugs out of cancer cells, rendering them ineffective. Variant BB seems to be more frequent in individuals of European and Asian origins than in individuals of African American orig The PGP protein is correlated with HIV and cancer medication uptake.

Actions

We recommends that you consult with your physician concerning this result, should you currently receive any cancer or HIV related medication.

In addition, We is monitoring for your tested sites that might be directly associated with drug uptake. As part of the Active Health Management Service, We will keep you updated as new research is published concerning drugs that are correlated with your variants in this gene.

Table 5 cont. Example of organizational matrix.

Endocrinology and metabolism

| Category | Pre-eclampsia | Gene Name |
|---|---|---|
| Metabolic Health | | EP |
| Clinical Description | | Items of Note |

Pre-eclampsia is the development of swelling, elevated blood pressure, and protein in the urine during pregnancy.

Epoxide Hydrolase 1, EPHX1, on chromosome 1 is associated pre-eclampsia.

Test Results

✓ Pre-eclampsia occurs in approximately 5% of all pregnancies. Increased risk is associated with first pregnancies, teenage mothers, mothers more than 40 years old, African-American women, multiple pregnancies, and women with a past history of diabetes, hypertension, or kidney disease.

We tested for results at 1 site in this gene. Your profile at this site is associated with a predisposition to develop pre-eclampsia.

Technical and Reference Information

At this site, omi13746, you have variant BB. Zusterzeel *et al.*, 2001, in the *Journal of Medical Genetics*, describe an association between women with this genotype and an enhanced susceptibility to pre-eclampsia.

Actions

We recommends that you consult with your physician concerning this result.

As part of the Active Health Management Service, We will keep you updated as new research is published concerning this site.

| Category | | Gene Name |
|---|---|---|
| Endocrinology and Metabolism | Obesity, insulin resistance, and diabetes | PPARG |
| Clinical Description | | Items of Note |

| Clinical Description | Items of Note |
|---|---|
| Diabetes is a problem with the body's fuel system. It is caused by lack of insulin, a hormone made in the pancreas (an organ that secretes enzymes needed for digestion) that is essential for getting energy from food.<br><br>The Peroxisome Proliferator-activated receptor-gamma gene, PPARG, on chromosome 3 has been associated with obesity, insulin resistance and diabetes. | ✓ There are 17 million people in the United States who have diabetes. Unfortunately, 5.9 million of those don't know it.<br><br>(Source: American Diabetes Association, 2002) |

Test Results

We tested for results at 11 sites in this gene. One of these sites is associated with developing type-2 diabetes.

Technical and Reference Information

Of the eleven genetic sites tested, ten were not associated with significant clinical conditions. You have a variant of note for one site.

You carry variant BB at site omi07101. This variant was described in Lindi *et al.*, 2002, in the journal *Diabetes*. They described clinical studies of patients participating in the Finnish Diabetes Prevention Study. This site was found to be associated with the incidence of diabetes and body weight change.

Variant BB is associated with a 2.11 times higher risk for developing type-2 diabetes over that of individuals who do not carry this variant. However, individuals who carry variant BB and who underwent an intensive diet program and exercised lost more weight than patients with one or no copies of variant B, and none of the these individuals in the study developed type-2 diabetes. Thus, while carrying two copies of variant B may predispose an individual to the development of type-2 diabetes in obese individuals, any impact of the predisposition may be reversed by weight loss, physical activity, and alterations in diet.

Actions

We recommends that you consult with your physician concerning this result. Given your higher risk of developing type-2 diabetes, you should be particularly aware of the symptoms of this condition. In addition, in conjunction with your physician you should assess whether you need to reduce your weight, increase physical activity, or alter your diet to minimize this risk. As part of the Active Health Management Service, we will keep you updated as new research is published concerning this site.

Table 5 cont. Example of organizational matrix.

Neurological and psychiatric disorders

| Category | Alzheimer's Disease | Gene Name |
|---|---|---|
| Neurological and Psychiatric | | AP |
| Clinical Description | | Items of Note |
| According to the National Institutes of Health, dementia is a brain disorder that seriously affects a person's ability to carry out daily activities. Alzheimer's disease is the most common form of dementia among older people. It involves the parts of the brain that control thought, memory, and language.<br><br>The Alzheimer gene, APP, on chromosome 21, has been shown to be associated with Alzheimer's disease, a disorder that manifests in plaque and tangle formation in the brain and with early onset dementia. APP is one of the major Alzheimer's disease genes. | | ✓ Approximately 4 million Americans have Alzheimer's disease. 14 million Americans will have Alzheimer's by 2050 unless a cure or prevention is found.<br><br>(Source, Alzheimer's Association, 2002) |
| Test Results | | |
| We tested for results at 30 sites in this gene. Your genetic profile indicates a low risk for developing Alzheimer's disease. | | |
| Technical and Reference Information | | |

Of the 30 genetic sites tested, including ones for the major classical mutations, you do not carry any of the seven early onset variants described above. The additional 23 tested sites have no variants with clinical association. The well-studied mutations are termed the Swedish, London, Florida, Flemish, Dutch, Arctic and Italian variants, and they are thought to predispose to early onset Alzheimer's symptoms.

Actions

The analysis of these sites indicates you do not have a predisposition for Alzheimer's disease. Please consult your physician to discuss these results.

Table 5 cont. Example of organizational matrix.

| Category | Gene Name |
|---|---|
| Neurological and Psychiatric | Alzheimer's Disease — AP |
| Clinical Description | Items of Note |

According to the National Institutes of Health, dementia is a brain disorder that seriously affects a person's ability to carry out daily activities. Alzheimer's disease is the most common form of dementia among older people. It involves the parts of the brain that control thought, memory, and language.

The APOE gene, on chromosome 19, has been shown to be associated with predispositions to Alzheimer's disease, cardiovascular disease, brain morphology and cognitive decline in aging.

Test Results

We tested for results at 51 sites in this gene. While one of the results is associated with a higher risk for the development of Alzheimer's, most people with this profile do not develop dementia, and about one-half of Alzheimer's cases are not related to this result.

✓ Half of all nursing home residents suffer from Alzheimer's disease.

✓ U.S society spends at least $100 billion a year on Alzheimer's disease.

(Source: Alzheimer's Association, 2002)

Technical and Reference Information

The APOE gene is one of the most intensely studied components of a persons genetic makeup, as it is thought to predispose to a number of common conditions, including cardiovascular disease, levels of high density lipoprotein (HDL) cholesterol, low density lipoprotein (LDL) cholesterol, changes in brain morphology and cognitive decline, and it enhances the extent of brain abnormalities in the presence of various vascular diseases.

An individual's genetic information in this special case consists of six different allelic combinations, E2/E2; E2/E3; E3/E3; E3/E4; E2/E4 and E4/E4. The literature states in general that it is the number of copies of E4 that a person carries that causes the greatest predisposition to a given disease. In general, carrying two copies of E4 is claimed to be potentially more deleterious than carrying a single copy of E4, whereas having no copies of E4 is the best outcome. However, under certain conditions, it is advantageous to carry two copies of E4, which can sometimes be protective of other conditions.

It is believed that the introduction of APOE4 individuals to Western dietary conditions and longer life spans may have been causally related to coronary arterial problems and age related dementias. There is no association between APOE4 genotype and coronary arterial conditions or age related dementias in sub-Saharan Africans, whereas there is an association with these conditions in African Americans. Thus, the APOE4 allele was not associated with dementia in a study of elderly Nigerians over 65 years of age (Osuntokun et al., 1995, Ann Neurol, 38, 463-465), whereas there was an association with E4 and Alzheimer's in African Americans.

At two of these tested sites, omi00005 and omi00009, you carry variants, two copies of variant A at market omi00005 and two copies of variant B at omi00009, which in combination, have been suggested to be a risk factor for Alzheimer's disease. This combination of variants is also known in the literature as E4/E4.

In the Framingham Study involving 1,030 individuals between the ages of 71 and 100, 55% of E4/E4 individuals developed Alzheimer's by age 80, in contrast to only 27% of E3/E4 individuals by age 85, and only 9% of individuals who did not carry any E4 allele. E2/E2, E2/E3 and E2/E4 individuals were Alzheimer's free in this study.

At the third site, omi00011, you carry two copies of variant B. In a large study from the Institute Pasteur in Lille, France, involving 1,732 individuals with Alzheimer's disease and 1,926 control persons, variant B has also been implicated as a risk factor in Alzheimer's disease.

At the fourth site, omi00017, you carry two copies of variant B, which is involved in controlling the level of activity of the APOE gene.

Studies at the departments of Pathology, Biochemistry and Neurology at the Autonomous University Hospital of Barcelona, Spain, and the Genetics and Clinical Medicine group at the laboratory of Clinical Analysis in Barcelona, Spain have revealed that at omi00017 there is an accumulation of variant B in healthy persons over the age of 75, suggesting that this variant plays a protective role against Alzheimer's disease. In fact, the study suggests that having two copies of variant B provides greater protection against Alzheimer's disease than the E2 site (Beyer et al., 2002, *Neuroreport*, 13, 1403-1405), commonly known as being protective against Alzheimers.

However, the major message from this analysis is that "although E4 is a potent risk factor for AD...most E4 carriers do not develop dementia, and about one-half of Alzheimer's disease is not E4 related".

Carrying two copies of E4 has benefits that are not enjoyed by carriers of the E2 and E3. The latest research as of August 2002 indicates that carriage of an E4 site may be protective against liver damage caused by the Hepatitis C virus (Wozriak et al., 2002, *Hepatology*, 36, 456-463).

The combination of variant AA for omi00005 and variant BB for omi00009, also known as allele carrier E4/E4, has been shown to be a risk factor for developing Alzheimer's disease. Nevertheless, most E4 carriers do not develop dementia, and about one-half of Alzheimer's disease is not E4 related.

The additional variant BB at omi00017 has on the contrary been shown to have a protective role.

Actions

Please discuss these results with your physician. There is no generally accepted treatment for Alzheimer's at this time. Inhibition of cholinesterase is the most broadly utilized approach to treating the symptoms of Alzheimer's disease. Tacrine is the drug that has consistently produced mild improvements in memory in some patients, with between 25% and 50% of treated individuals having a significant clinical response. (Farlow et al., *Annals of the NY Acad Sci*, 101-110; Marshall, 1997, *Nature Biotechnology*, 15, 1249-1252; Poirer et al., 1995, *PNAS*, 92, 12260-12264).

However, trials of new experimental drugs that are thought to prevent or slow Alzheimer's, such as S12024, have been found to significantly benefit subsets of individuals with E4 sites, (Richard et al., 1997, *Lancet*, 349, 539).

Table 5 cont. Example of organizational matrix.

| Category | Gene Name |
|---|---|
| Neurological and Psychiatric | Spinal Cord — CO |
| Clinical Description | Items of Note |

| Clinical Description | Items of Note |
|---|---|
| Invertebral disks are made up of cartilage and separate the bones of the back known as vertebrae.<br><br>The Collagen gene, COL9A2, on chromosome 1, has been shown to be associated with intervertebral disk disease, a musculo-skeletal disorder. | ✓ The prevalence for intervertebral disk disease is 4% in the USA. |
| Test Results<br><br>We tested for results at 1 site in this gene. This site is associated with a predisposition for developing invertebral disk disease. | ✓ Site omi24023 has been shown to be linked to intervertebral disk disease in populations of Finnish and German origin. |

Technical and Reference Information

The genetic site tested showed a variant with significant clinical conditions.

At this site, omi024023, you have variant BB. This variant has been associated with dominantly inherited intervertebral or lumbar disk disease. Annunen *et al.* in the Journal *Science* in 1999 found it in 4% of Finnish patients with Intervertebral Disk Disease but in none of a series of 174 individuals without the disease. Wrocklage and colleagues from the University Munster in Germany could also show association of this variant in 1.2% of elderly German population, whereby the carriers were significantly older than the average.

Actions

You should consult with your physician to determine whether there are any specific preventative actions that you should take.

As part of the Active Health Management Service, We will keep you updated as new research is published concerning this site.

| Category | Gene Name |
|---|---|
| Neurological and Psychiatric | CO |
| Clinical Description — Spinal Cord | Items of Note |

The lumbar region of the back goes from the lower part of the ribs down to the hips.

The Collagen gene, COL9A3, on chromosome 20, has been shown to be associated with lumbar disk disease, a neurological disorder of the spinal cord.

✓ The prevalence for lumbar disk disease is 5% in the USA.

Test Performed

We tested for results at 5 sites in this gene. Your genetic profile is associated with an increased risk for developing lumber disk disease.

Test Results

Of the five genetic sites tested, four were not associated with significant clinical conditions. You have a variant of note for one site.

At this site, omi012003, you have variant AB. This variant has been shown by teams at Columbia, Rockefeller and Hahnemann Universities USA, the National Institute of Child Health and Human Development at the NIH, USA, and the Universities of Oulu, Kuopio and Helsinki in Finland to be associated with an increased risk of lumbar disk disease, one of the most common musculo-skeletal conditions in the USA.

Paassilta et al. showed in *the Journal of the American Medical Association* in 2001 that carrying one or two copies of variant B at site omi12003 increases the risk of lumbar disk disease about 3 fold over individuals that carry no copies of this variant.

Actions

You should consult with your physician to determine whether there are any specific preventative actions that you should take.

As part of the Active Health Management Service, We will keep you updated as new research is published concerning this site.

Table 5 cont. Example of organizational matrix.

Others

| Category | Gene Name |
|---|---|
| Others | Blindness — AC |

| Clinical Description | Items of Note |
|---|---|
| The macula is part of the light-sensoring part of the eye called the retina. Macular degeneration is the injury or deterioration of the macula.<br><br>The angiotensin gene, ACE, on chromosome 17, has been shown to be associated with age-related macular degeneration (AMD), which is the leading cause of blindness in the elderly. | ✓ About 25% of people aged 65 and older have some form of macular degeneration. About 11% of people between 65 and 74 are affected, and about 28% of people 75 and older.<br><br>(Source: WebMD, 2002) |

Test Performed

We tested for results at 2 sites in this gene. Your profile is associated with low risk of developing macular degeneration.

Test Results

Of the two genetic sites tested, one was not associated with significant clinical conditions. You have a variant of note for one site.

At this site, omi00223, you have variant AA. In a recent clinical study, this variant has been shown to have a protective effect against blindness inn the elderly. In the study by Hamdi et al., 2002, they reported a 4.5 times higher occurrence of this variant in an unaffected control group versus an AMD patient population.

Actions

Please discuss these results with your physician. As part of the Active Health Management Service, We will keep you updated as new research is published concerning sites in this gene. In addition, CYP3A4 has been associated with various drug uptake reactions. We is monitoring research that may be directly associated with drug uptake as it applies to you.

| Category | Gene Name |
|---|---|
| Others | Addiction to nicotine and alcohol / DR |
| Clinical Description | Items of Note |

The dopamine receptor gene, DRD2, on chromosome 11, has been shown to be associated with cigarette smoking as well as the severity of alcohol dependence.

✓ Tobacco use causes more than 440,000 deaths each year and results in an annual cost of more than $75 billion in direct medical costs.

Test Results

We tested for results at 6 sites in this gene. Your variant has been shown to be associated with addiction to smoking and alcohol abuse.

(Source: Center for Disease Control, 2002)

Technical and Reference Information

Of the six genetic sites tested, five were not associated with significant clinical conditions. You have a variant of note for one site.

At this site, omi10011, you have variant BB. In one large clinical study, Caporaso et al. found that variant BB was approximately twice as common in smokers compared to non-smokers.

In another study at Department of Psychiatry, University of Queensland, Australia, Connor et al. reported that alcohol-dependent patients with variant BB compared to patients without this allele are characterized by greater severity of their disorder across a range of problem drinking indices. This study was conducted in a Caucasian adult population, recruited from an alcohol detoxification unit.

Actions

We recommends that you consult with your physician concerning this result.

In addition, We is monitoring research for results that might be directly associated with drug uptake. As part of the Active Health Management Service, We will keep you updated as new research is published concerning drugs that are correlated with your variants in this gene.

Table 5 cont. Example of organizational matrix.

Rare Genetic Conditions or Carrier Report

Many genetic conditions are very rare. If your genetic profile contained a notable site within one of the genes, it has been reported in the Health Category Reports. However, despite there relative rarity, many people have a particular condition in which they have an interest. The following list summarizes the tests that we performed for these rare conditions for which you have no notable site and therefore you are not even a carrier for one of the disease related variants.

Table 5 cont. Example of organizational matrix

| Disease | Gene |
|---|---|
| Aarskog-Scott syndrome | FGD1 |
| Abetalipoproteinemia | MTP |
| Acatalasemia | CAT |
| Achondroplasia | FGFR3 |
| Achromatopsia-2 | CNGA3 |
| Achromatopsia-3 | CNGB3 |
| Acromesomelic dysplasia | GDF5 |
| ACTH deficiency | POMC |
| Acyl-CoA dehydrogenase | ACADL |
| Acyl-CoA dehydrogenase | ACADM |
| Acyl-CoA dehydrogenase | ACADS |
| Adenylosuccinase deficiency | ADSL |
| Adrenal hyperplasia | CYP11B1 |
| Adrenal hyperplasia | CYP17 |
| Adrenal hyperplasia | CYP21A2 |
| Adrenal hypoplasia | AHC? |
| Adrenoleukodystrophy | PXR1 |
| Adrenoleukodystrophy | ABCD1 |
| AFP deficiency | AFP |
| Agammaglobulinemia | IGHM |
| Agammaglobulinemia | BTK |
| AIDS | SDF1 |
| Alagille syndrome | JAG1 |
| Albinism | TYRP1 |
| Albinism | TYR |
| Albinism | OCA2 |
| Alcohol intolerance | ALDH2 |
| Aldolase A deficiency | ALDOA |
| Alkaptonuria | HGD |
| Alopecia universalis | HR |
| Alpha-1-antichymotrypsin deficiency | AACT |
| Alpha-methylacyl-CoA racemase deficiency | AMACR |
| Alpha-thalassemia/mental retardation syndrome | ATRX |
| Alport syndrome | COL4A5 |
| Alport syndrome | COL4A3 |
| Alport syndrome | COL4A4 |
| Alzheimer disease | BLMH |
| Alzheimer disease-3 | PSEN1 |
| Alzheimer disease-4 | PSEN2 |
| Amelogenesis Imperfecta | |
| AMP deaminase deficiency | AMPD3 |
| Amyloid neuropathy | TTR |
| Amyloidosis | APP |
| Amyloidosis | GSN |
| Amyloidosis | LYZ |

| | |
|---|---|
| Amyotrophic lateral sclerosis | NEFH |
| Amytrophic lateral sclerosis | SOD1 |
| Analbuminemia | ALB |
| Androgen insensitivity | AR |
| Anemia | RPS19 |
| Anemia | PKLR |
| Anemia | RHAG |
| Anemia | ABCB7 |
| Anemia | ALAS2 |
| Angelman syndrome | UBE3A |
| Angioedema | |
| Anhaptoglobinemia] | HP |
| Aniridia | PAX6 |
| Anterior segment mesenchymal dysgenesis and cataract | PITX3 |
| Antithrombin III deficiency | AT3 |
| Anxiety-related personality traits | SLC6A4 |
| Apnea | BCHE |
| ApoA-I and apoC-III deficiency | APOA1 |
| Apolipoprotein A-II deficiency | APOA2 |
| Apolipoprotein H deficiency] | APOH |
| Argininemia | ARG1 |
| Argininosuccinicaciduria | ASL |
| Aspartylglucosaminuria | AGA |
| Asthma | MS4A2 |
| Asthma | ADRB2 |
| Ataxia with isolated vitamin E deficiency | TTPA |
| Ataxia-telangiectasia | ATM |
| Ataxia-telangiectasia-like disorder | MRE11A |
| Atopy | IL4R |
| Atrial septal defect with atrioventricular conduction defects | CSX |
| Autoimmune lymphoproliferativesyndrome | TNFRSF6 |
| Autoimmune polyglandular disease | AIRE |
| Autonomic nervous system dysfunction | DRD4 |
| Azoospermia | USP9Y |
| Bamforth-Lazarus syndrome | FOXE1 |
| Bartter syndrome | SLC12A1 |
| Bartter syndrome | KCNJ1 |
| Bartter syndrome | CLCNKB |
| Basal cell carcinoma | RASA1 |
| Basal cell nevus syndrome | PTCH |
| Beckwith-Wiedemann syndrome | CDKN1C |
| Benzene toxicity | NQO1 |
| Bernard-Soulier syndrome | GP1BB |
| Bernard-Soulier syndrome | GP9 |
| Bernard-Soulier syndrome | GP1BA |
| Beryllium disease | HLA-DPB1 |
| Bethlem myopathy | COL6A1 |
| Bethlem myopathy | COL6A2 |

| | |
|---|---|
| Bethlem myopathy | COL6A3 |
| Bile acid malabsorption | SLC10A2 |
| Biotinidase deficiency | BTD |
| Bladder cancer | HRAS |
| Bleeding disorder due to defective thromboxane A2 receptor | TBXA2R |
| Bloom syndrome | BLM |
| Brachydactyly | ROR2 |
| Branchiootorenal syndrome | EYA1 |
| Breast cancer | SLC22A1L |
| Breast cancer | PHB |
| Breast cancer | ESR1 |
| Breast cancer 2 | BRCA2 |
| Breast cancer-1 | BRCA1 |
| Brody myopathy | ATP2A1 |
| Brunner syndrome | MAOA |
| Burkitt lymphoma | MYC |
| C1q deficiency | C1QA |
| ... | |
| Xanthinuria | XDH |
| Xeroderma pigmentosum | XPA |
| Xeroderma pigmentosum | XPC |
| Xeroderma pigmentosum | ERCC2 |
| Xeroderma pigmentosum | DDB2 |
| Xeroderma pigmentosum | ERCC4 |
| Xeroderma pigmentosum | ERCC5 |
| Xeroderma pigmentosum | POLH |
| Zellweger syndrome | PEX13 |
| Zellweger syndrome | PEX10 |
| Zellweger syndrome-1 | PEX1 |
| Zellweger syndrome-3 | PXMP3 |

The invention claimed is:

1. A method for determining an individual's probability of exhibiting one or more phenotypic attributes, comprising:
   a) evaluating genomic markers from the individual for zygosity at each member of a preselected set of markers; wherein each preselected marker has a degree of linkage with one or more of the one or more phenotypic attributes, wherein zygosity is heterozygosity or homozygosity for each selected marker from the preselected set;
   b) comparing the zygosity of the preselected markers to a multivariate scoring matrix to obtain a marker score, wherein the multivariate scoring matrix correlates patterns of marker zygosity with probabilities of exhibiting the one or more phenotypic attributes, using suitable computer software for use on a computer;
      wherein the scoring matrix prioritizes markers with respect to one or more criteria selected from the group consisting of synteny with respect to other marker sequences, ontological relevance, quality of supporting research, and degree of phenotypic significance; and
   c) determining whether the marker score indicates an enhanced, diminished, or average probability of exhibiting one or more phenotypic attributes.

2. The method according to claim 1, wherein the preselected set of markers comprises a plurality of exon/intron junction sequences.

3. The method according to claim 2, wherein at least about 20% of the markers in the preselected set are exon/intron junction sequences.

4. The method according to claim 1, wherein the preselected set of markers comprises a plurality of promoter sequences.

5. The method according to claim 4, wherein at least about 20% of the markers in the preselected set are promoter sequences.

6. The method according to claim 1, wherein one or more of the markers within the preselected set of markers is selected by prioritizing with respect to one or more criteria selected from the group consisting of nucleotide sequence homology, synteny with respect to other marker sequences, ontological relevance, genomic relevance, quality of supporting research, and degree of phenotypic significance.

7. The method according to claim 1, wherein the preselected set of markers comprises markers that map to at least about 1,000 discrete loci.

8. The method according to claim 1, wherein the scoring matrix prioritizes markers with respect to homology to another marker sequence of interest, synteny with respect to other marker sequences, ontological relevance, genomic relevance, quality of supporting research, and degree of phenotypic significance.

9. The method according to claim 1, wherein the method further comprises determining a genetic profile characteristic of a human population or subpopulation, 10. The method according to claim 9, wherein the method further comprises using the genetic profile characteristic of the human population or subpopulation in a pharmacogenomic analysis.

11. A method for providing genetic information to an individual, comprising:
   a) identifying genotypic characteristics of the individual that correlate with a relative probability of exhibiting one or more phenotypic attributes;
   b) determining for each of the one or more phenotypic attributes the probability of exhibiting the one or more phenotypic attributes by:
      (i) evaluating genomic markers from an individual for zygosity at each member of a preselected set of markers, wherein each preselected marker has a degree of linkage with one or more of the one or more phenotypic attributes, wherein zygosity is heterozygosity or homozygosity for each selected marker from the preselected set;
      (ii) comparing the zygosity of the preselected markers to a multivariate scoring matrix to obtain a marker score, wherein the multivariate scoring matrix correlates patterns of marker zygosity with probabilities of exhibiting the one or more phenotypic attributes, using suitable computer software for use on a computer;
         wherein the scoring matrix prioritizes markers with respect to one or more criteria selected from the group consisting of synteny with respect to other marker sequences, ontological relevance, quality of supporting research, and degree of phenotypic significance; and
      (iii) determining whether the marker score indicates an enhanced, diminished, or average probability of exhibiting the one or more phenotypic attributes;
   c) applying one or more selection criteria for each of the one or more phenotypic attributes to the resulting determinations of probability, wherein each selection criterion imposes total, partial, or no limitation on the information communicated to the individual;
   d) identifying information that is relevant to the individual's probabilities of exhibiting the one or more phenotypic attributes and consistent with the limitations imposed by the selection criteria; and
   e) communicating the information to the individual.

12. The method according to claim 11, further comprising:
   applying the same or different selection criteria one or more additional times to the determined probabilities of exhibiting each of the phenotypic attributes;
   identifying information that is relevant to the individual's probabilities of exhibiting the one or more phenotypic attributes and consistent with the limitations imposed by the selection criteria; and
   communicating the information to the individual.

13. The method according to claim 11, wherein the scoring matrix comprises a combination of one or more scoring matrix vectors selected from the group consisting of a descriptor of family history, a descriptor of general medical physiological values, a descriptor of mRNA expression levels, a descriptor of methylation profiles, a descriptor of protein expression levels, a descriptor of enzyme activity, and a descriptor of antibody load.

14. The method according to claim 11, wherein at least one of the one or more selection criteria is specified in advance by the individual.

15. The method according to claim 14, wherein at least one of the one or more selection criteria is a function of the availability of treatments effective to modify the phenotypic characteristic.

16. The method according to claim 11, wherein at least one of the one or more selection criteria is a function of the scope and quality of known research relating to the phenotypic characteristic.

17. The method according to claim 11, wherein at least one of the one or more selection criteria is a function of the probability determination(s) for one or more other phenotypic attributes.

18. The method according to claim 11, further comprising, prior to communicating the information to the individual:
formatting the information relating to the relevant phenotypic attributes according to an organizational matrix, wherein the organizational matrix determines the grouping, and presentation of information to the individual.

19. The method according to claim 18, wherein the organizational matrix groups phenotypic characteristics for which the individual has an enhanced probability together.

20. The method according to claim 18, wherein the organizational matrix groups phenotypic attributes related to similar physiological systems together.

21. The method according to claim 18, wherein the organization matrix ranks the phenotypic attributes as a function of the potential impact on the individual's lifestyle or quality of life.

22. The method according to claim 18, wherein the organization matrix ranks the phenotypic characteristics as a function of the genomic ethnicity of the individual.

23. The method according to claim 11, wherein prior to communicating the information to the individual, the identity of the individual is not associated with data corresponding to the genotypic characteristics, the relative probabilities of exhibiting the phenotypic attributes, or the identified relevant information.

24. The method according to claim 1 or claim 11, wherein the method comprises prioritizing markers with respect to synteny with respect to other marker sequences.

25. The method according to claim 1 or claim 11, wherein the method further comprises prioritizing markers with respect to ontological relevance.

26. The method according to claim 1 or claim 11, wherein the method comprises prioritizing markers with respect to genomic relevance.

27. The method according to claim 1 or claim 11, wherein the method comprises prioritizing markers with respect to quality of supporting research.

28. The method according to claim 1 or claim 11, wherein the method comprises prioritizing markers with respect to degree of phenotypic significance.

* * * * *